US009029378B2

(12) United States Patent
Frank et al.

(10) Patent No.: US 9,029,378 B2
(45) Date of Patent: May 12, 2015

(54) SUBSTITUTED BICYCLIC AROMATIC CARBOXAMIDE AND UREA COMPOUNDS AS VANILLOID RECEPTOR LIGANDS

(75) Inventors: Robert Frank, Aachen (DE); Thomas Christoph, Aachen (DE); Bernhard Lesch, Aachen (DE); Jeewoo Lee, Shinlim-Dong-Kwanak-Ku (KR)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/557,863

(22) Filed: Jul. 25, 2012

(65) Prior Publication Data

US 2013/0029995 A1 Jan. 31, 2013

Related U.S. Application Data

(60) Provisional application No. 61/511,769, filed on Jul. 26, 2011.

(30) Foreign Application Priority Data

Jul. 26, 2011 (EP) .................................... 11006113

(51) Int. Cl.
C07D 401/12 (2006.01)
C07D 471/04 (2006.01)

(52) U.S. Cl.
CPC ............ *C07D 401/12* (2013.01); *C07D 471/04* (2013.01)

(58) Field of Classification Search
None
See application file for complete search history.

(56) References Cited

U.S. PATENT DOCUMENTS

| 2005/0113576 A1* | 5/2005 | Lee et al. ....................... 544/182 |
| 2006/0052374 A1* | 3/2006 | Carroll et al. ............... 514/227.5 |
| 2008/0058401 A1* | 3/2008 | Lee et al. ....................... 514/403 |
| 2010/0256097 A1 | 10/2010 | Altman et al. |
| 2011/0184020 A1 | 7/2011 | Frank et al. |

FOREIGN PATENT DOCUMENTS

| WO | WO 2006/014290 A2 | 2/2006 |
| WO | WO 2006/081034 A2 | 8/2006 |
| WO | WO 2007/045462 A2 | 4/2007 |
| WO | WO 2007/053394 A1 | 5/2007 |
| WO | WO 2007/113548 A1 | 10/2007 |
| WO | WO 2008/125337 A2 | 10/2008 |
| WO | WO 2008/125342 A2 | 10/2008 |
| WO | WO 2008/125342 A3 | 10/2008 |
| WO | WO 2009/026204 A1 | 2/2009 |
| WO | WO 2010/094956 A1 | 8/2010 |
| WO | WO 2010/115719 A1 | 10/2010 |
| WO | WO 2010/127855 A1 | 11/2010 |
| WO | WO 2010/127856 A1 | 11/2010 |
| WO | WO 2011/024932 A1 | 3/2011 |

OTHER PUBLICATIONS

Dorwald F. A. "Side Reactions in Organic Synthesis", 2005, Wiley: VCH, Weinheim, p. IX of Preface and pp. 1-16.*
Brian S. Brown, et al.: "Discovery of TRPV1 Antagonist ABT-116", Bioorganic & Medicinal Chemistry Letters, vol. 20, No. 11, 2010, pp. 3291-3294, XP-002658502.
European Search Report dated Sep. 22, 2011 (five (5) pages).
Bennett et al., "A peripheral mononeuropathy in rat that produces disorders of pain sensation like those seen in man", Pain, 1988, vol. 33, pp. 87-107 (twenty-one (21) sheets).
Kim et al., "An experimental model for peripheral neuropathy produced by segmental spinal nerve ligation in the rat", Pain, 1992, vol. 50, pp. 355-363 (nine (9) sheets).
Siegel, F. PhD., "Tonicity, Osmoticity, Osmolality and Osmolarity", Remington Chapter 80 (eighteen (18) sheets). 1985.
Carey et al., "Part A: Structure and Mechanisms", Advanced Organic Chemistry, Fifth Edition, 2007 (twenty-two (22) sheets).
Smith et al., "Reactions, Mechanisms, and Structure", March's Advanced Organic Chemistry, 6th edition, 2007 (four (4) sheets).
Giles et al., "Plastic Packaging Materials", Remington Chapter 81 (five (5) sheets), 1985.
Carey et al., "Part B: Reactions and Synthesis", Advanced Organic Chemistry, Fifth Edition, 2007 (twenty-nine (29) sheets).
Ravin, L. PhD., "Preformulation", Remington Chapter 76 (fifteen (15) sheets). 1985.
Lintner, C. PhD., "Stability of Pharmaceutical Products", Remington Chapter 82 (nine (9) sheets). 1985.
Cheng et al., "Relationship between the inhibition constant (KI) and the concentration of inhibitor which causes 50 per cent inhibition (I50) of an enzymatic reaction", Biochemical Pharmacology, 1973, vol. 22, pp. 3099-3108 (ten (10) sheets).
Disanto, A., "Bioavailability and Bioequivalency Testing", Remington Chapter 77 (eight (8) sheets). 1985.
Erskine, C., Jr., "Quality Assurance and Control" Remington Chapter 83 (five (5) sheets). 1985.
D'Amour et al., "A Method for Determining Loss of Pain Sensation", The Journal of Pharmacology and Experimental Therapeutics, 1941 (six (6) sheets).
Knevel, A. PhD., "Separation", Remington Chapter 78 (eleven (11) sheets). 1985.
Dubuisson et al., "The Formalin Test: A quantitative study of the analgesic effects of morphine, meperidine, and brain stem stimulation in rats and cats", Pain, 1977, vol. 4, pp. 161-174 (fourteen (14) sheets).
Phillips, G Briggs, PhD., "Sterilization", Remington Chapter 79 (twelve (12) sheets). 1985.
Nairn, J.G. PhD., "Solutions, Emulsions, Suspensions and Extractives", Remington Chapter 84 (twenty-six (26) sheets). 1985.
Avis, K. DSc., "Parenteral Preparations", Remington Chapter 85 (twenty-four (24) sheets). 1985.

(Continued)

*Primary Examiner* — James C Anderson
(74) *Attorney, Agent, or Firm* — Crowell & Moring LLP

(57) ABSTRACT

Substituted bicyclic aromatic carboxamide and urea compounds as vanilloid receptor ligands, pharmaceutical compositions containing these compounds, and a method of using these compounds in the treatment and/or inhibition of pain and further diseases and/or disorders mediated at least in part via the vanilloid receptor 1 (VR1/TRPV1).

5 Claims, No Drawings

(56) References Cited

OTHER PUBLICATIONS

Turco et al., "Intravenous Admixtures", Remington Chapter 86 (eleven (11) sheets). 1985.
Mullins, J. PhD., "Ophthalmic Preparations", Remington Chapter 87 (fourteen (14) sheets). 1985.
Block, L. PhD., "Medicated Applications", Remington Chapter 88 (eighteen (18) sheets). 1985.
Rippie, E. PhD., "Powders", Remington Chapter 89 (eighteen (18) sheets). 1985.
King et al., "Oral Solid Dosage Forms", Remington Chapter 90 (thirty (30) sheets). 1985.
Porter, S. PhD., "Coating of Pharmaceutical Dosage Forms", Remington Chapter 91 (eleven (11) sheets). 1985.
Longer et al., "Sustained-Release Drug Delivery Systems", Remington Chapter 92 (eighteen (18) sheets). 1985.
Sclarra et al., "Aerosols", Remington Chapter 93 (sixteen (16) sheets). 1985.
Yukio Tominaga et al., "General Model for Estimation of the Inhibition of Protein Kinases Using Monte Carlo Simulations", Journal of Medicinal Chemistry, 2004, pp. 2534-2549, vol. 47, No. 10, XP002658752.
European Search Report dated Sep. 22, 2011 (Seven (7) pages).
Abstract of WO 2008/156726 A1 dated Dec. 24, 2008 which corresponds to Document A2.
Block, L. PhD., "Medicated Applications", Remington Chapter 88 (twenty-two (22) sheets). 1985.
European Search Report dated Sep. 22, 2011 (six (6) pages).
Ahn et al., "Synthesis and Antiproliferative Activity of Pyridinylcarbonylpyrimidines Against Melanoma Cell Line", Bulletin of the Korean Chemical Society, Apr. 20, 2011, vol. 32, No. 4, pp. 1209-1214.

* cited by examiner

SUBSTITUTED BICYCLIC AROMATIC CARBOXAMIDE AND UREA COMPOUNDS AS VANILLOID RECEPTOR LIGANDS

CROSS REFERENCE TO RELATED APPLICATIONS

This application claims priority from co-pending U.S. provisional patent application No. 61/511,769, filed Jul. 26, 2011, the entire disclosure of which is incorporated herein by reference. Priority is also claimed based on European patent application no. EP 11 001 113.2, filed Jul. 26, 2011, the entire disclosure of which is likewise incorporated herein by reference.

BACKGROUND OF THE INVENTION

The invention relates to substituted bicyclic aromatic carboxamide and urea derivatives as vanilloid receptor ligands, to pharmaceutical compositions containing these compounds and also to these compounds for use in the treatment and/or inhibition of pain and further diseases and/or disorders.

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain. This receptor is stimulated inter alia by vanilloids such as capsaicin, heat and protons and plays a central role in the formation of pain. In addition, it is important for a large number of further physiological and pathophysiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and urinary incontinence.

There is a demand for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example.

SUMMARY OF THE INVENTION

It was therefore an object of the invention to provide novel compounds, preferably having advantages over the prior-art compounds.

Another object of the invention was to provide new compounds which are suitable in particular as pharmacological active ingredients in pharmaceutical compositions.

It was also a particular object of the invention to provide new compounds useful for the treatment and/or inhibition of disorders or diseases which are at least partially mediated by vanilloid receptors 1 (VR1/TRPV1 receptors).

These and other objects have been achieved in accordance with the present invention by the compounds, compositions and methods as described and claimed hereinafter.

It has surprisingly been found that the substituted compounds of general formula (I), as given below, display outstanding affinity to the subtype 1 vanilloid receptor (VR1/TRPV1 receptor) and are therefore particularly suitable for the inhibition and/or treatment of disorders or diseases which are at least partially mediated by vanilloid receptors 1 (VR1/TRPV1).

The present invention therefore relates to a substituted compound of general formula (I),

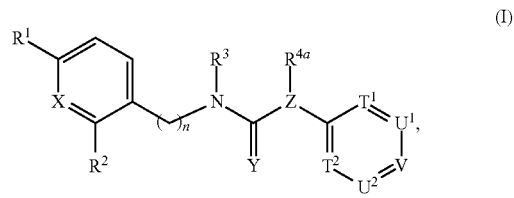

wherein
$R^0$ represents a $C_{1-10}$ aliphatic residue, unsubstituted or mono- or polysubstituted; a $C_{3-10}$ cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;
X represents N or CH;
$R^1$ represents a $C_{1-4}$ aliphatic residue, unsubstituted or mono- or polysubstituted, a $C_{3-6}$ cycloaliphatic residue or a 3 to 6 membered heterocycloaliphatic residue, in each case unsubstituted or mono- or polysubstituted;
$R^2$ represents $R^0$; O—$R^0$; S—$R^0$; $NH_2$; N—H($R^0$ or N($R^0$)$_2$;
n represents 0, 1, 2, 3 or 4, preferably represents 1, 2, 3 or 4, more preferably represents 1, 2 or 3;
$R^3$ represents H or a $C_{1-4}$ aliphatic residue, unsubstituted or mono- or polysubstituted;
$R^{4a}$ represents H or a $C_{1-4}$ aliphatic residue, unsubstituted or mono- or polysubstituted, a $C_{3-6}$ cycloaliphatic residue, unsubstituted or mono- or polysubstituted, or an aryl, unsubstituted or mono- or polysubstituted;
Y represents O, S, or N—CN, preferably represents O;
Z represents N or C—$R^{4b}$,
  with the proviso that Z denotes N, if $T^1$ represents C—$R^5$, $U^1$ represents C—$R^6$, V denotes C—$R^7$, $U^2$ represents $CR^8$ and $T^2$ denotes $CR^9$;
$R^{4b}$ represents H or a $C_{1-4}$ aliphatic residue, unsubstituted or mono- or polysubstituted; or
$R^{4a}$ and $R^{4b}$ together with the carbon atom connecting them form a $C_{3-6}$ cycloaliphatic residue, unsubstituted or mono- or polysubstituted;
$T^1$ represents N or C—$R^5$,
$U^1$ represents N or C—$R^6$,
V represents N or C—$R^7$,
$U^2$ represents N or C—$R^8$,
$T^2$ represents N or C—$R^9$, with the proviso that 0, 1, or 2, preferably 0 or 1, of variables $T^1$, $U^1$, V, $U^2$ and $T^2$ represent a nitrogen atom simultaneously, and $R^5$ and $R^6$ together or
$R^6$ and $R^7$ together or
$R^7$ and $R^8$ together or
$R^8$ and $R^9$ together, in each case independently of one another, together with the carbon atoms connecting them form a $C_{3-10}$-cycloaliphatic residue, preferably a $C_{3-6}$-cycloaliphatic residue, or a 3 to 10 membered heterocycloaliphatic residue, preferably a 3 to 6 membered heterocycloaliphatic residue, in each case unsubstituted or mono- or polysubstituted, or form an aryl or heteroaryl, in each case unsubstituted or mono- or polysubstituted;

and the respective remaining substituents of $R^5$, $R^6$, $R^7$, $R^8$, and $R^9$ each independently of one another represent H; F; Cl; Br; I; CN; $CF_3$; $CF_2H$; $CFH_2$; $CF_2Cl$; $CFCl_2$; $NO_2$; $R^0$; C(=O)—H; C(=O)—$R^0$; C(=O)—OH; C(=O)—$OR^0$; C(=O)—$NH_2$; C(=O)—$NHR^0$; C(=O)—$N(R^0)_2$; OH; $OCF_3$; $OCF_2H$; $OCFH_2$; $OCF_2Cl$; $OCFCl_2$; $OR^0$; O—C(=O)—$R^0$; O—C(=O)—O—$R^0$; O—(C=O)—$NHR^0$; O—C(=O)—$N(R^0)_2$; O—S(=O)$_2$—$R^0$; O—S(=O)$_2$—OH; O—S(=O)$_2$—$OR^0$; O—S(=O)$_2$—$NH_2$; O—S(=O)$_2$—$NHR^0$; O—S(=O)$_2$—$N(R^0)_2$; $NH_2$; $NHR^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—$N(R^0)_2$; $NR^0$—C(=O)—$R^0$; $NR^0$—C(=O)—O—$R^0$; $NR^0$—C(=O)—$NH_2$; $NR^0$—C(=O)—$NHR^0$; $NR^0$—C(=O)—$N(R^0)_2$; NH—S(=O)$_2$—OH; NH—S(=O)$_2$—$R^0$; NH—S(=O)$_2$—$OR^0$; NH—S(=O)$_2$—$NH_2$; NH—S(=O)$_2$—$NHR^0$; NH—S(=O)$_2$—$N(R^0)_2$; $NR^0$—S(=O)$_2$—OH; $NR^0$—S(=O)$_2$—$R^0$; $NR^0$—S(=O)$_2$—$OR^0$; $NR^0$—S(=O)$_2$—$NH_2$; $NR^0$—S(=O)$_2$—$NHR^0$; $NR^0$—S(=O)$_2$—$N(R^0)_2$; SH; $SCF_3$; $SCF_2H$; $SCFH_2$; $SCF_2Cl$; $SCFCl_2$; $SR^0$; S(=O)—$R^0$; S(=O)$_2$—$R^0$; S(=O)$_2$—OH; S(=O)$_2$—$OR^0$; S(=O)$_2$—$NH_2$; S(=O)$_2$—$NHR^0$; or S(=O)$_2$—$N(R^0)_2$;

in which an "aliphatic group" and "aliphatic residue" can in each case, independently of one another, be branched or unbranched, saturated or unsaturated;

in which a "cycloaliphatic residue" and a "heterocycloaliphatic residue" can in each case, independently of one another, be saturated or unsaturated;

in which "mono- or polysubstituted" with respect to an "aliphatic group", an "aliphatic residue", a "cycloaliphatic residue" and a "heterocycloaliphatic residue" relates in each case independently of one another, with respect to the corresponding residues or groups, to the replacement of one or more hydrogen atoms each independently of one another by at least one substituent selected from the group consisting of F; Cl; Br; I; $NO_2$; CN; =O; =NH; =N(OH); =C(NH$_2$)$_2$; $CF_3$; $CF_2H$; $CFH_2$; $CF_2Cl$; $CFCl_2$; $R^0$; C(=O)—H; C(=O)—$R^0$; C(=O)—OH; C(=O)—$OR^0$; CO—$NH_2$; C(=O)—$NHR^0$; C(=O)—$N(R^0)_2$; OH; $OCF_3$; $OCF_2H$; $OCFH_2$; $OCF_2Cl$; $OCFCl_2$; $OR^0$; O—C(=O)—$R^0$; O—C(=O)—O—$R^0$; O—(C=O)—NH—$R^0$; O—C(=O)—$N(R^0)_2$; O—S(=O)$_2$—$R^0$; O—S(=O)$_2$—OH; O—S(=O)$_2$—$OR^0$; O—S(=O)$_2$—$NH_2$; O—S(=O)$_2$—$NHR^0$; O—S(=O)$_2$—$N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—$NHR^0$; NH—C(=O)—N(R)$_2$; $NR^0$—C(=O)—$R^0$; $NR^0$—C(=O)—O—$R^0$; $NR^0$—C(=O)—$NH_2$; $NR^0$—C(=O)—$NHR^0$; $NR^0$—C(=O)—$N(R^0)_2$; NH—S(=O)$_2$—OH; NH—S(=O)$_2$—$R^0$; NH—S(=O)$_2$—$OR^0$; NH—S(=O)$_2$—$NH_2$; NH—S(=O)$_2$—$NHR^0$; NH—S(=O)$_2$—$N(R^0)_2$; $NR^0$—S(=O)$_2$—OH; $NR^0$—S(=O)$_2$—$R^0$; $NR^0$—S(=O)$_2$—$OR^0$; $NR^0$—S(=O)$_2$—$NH_2$; $NR^0$—S(=O)$_2$—$NHR^0$; $NR^0$—S(=O)$_2$—$N(R^0)_2$; SH; $SCF_3$; $SCF_2H$; $SCFH_2$; $SCF_2Cl$; $SCFCl_2$; $SR^0$; S(=O)—$R^0$; S(=O)$_2$—$R^0$; S(=O)$_2$—OH; S(=O)$_2$—$OR^0$; S(=O)$_2$—$NH_2$; S(=O)$_2$—$NHR^0$; and S(=O)$_2$—$N(R^0)_2$;

in which "mono- or polysubstituted" with respect to "aryl" and a "heteroaryl" relates, with respect to the corresponding residues, in each case independently of one another, to the replacement of one or more hydrogen atoms each independently of one another by at least one substituent selected from the group consisting of F; Cl; Br; I; $NO_2$; CN; $CF_3$; $CF_2H$; $CFH_2$; $CF_2Cl$; $CFCl_2$; $R^0$; C(=O)—H; C(=O)—$R^0$; C(=O)—OH; C(=O)—$OR^0$; CO—$NH_2$; C(=O)—$NHR^0$; C(=O)—) $N(R^0)_2$; OH; $OCF_3$; $OCF_2H$; $OCFH_2$; $OCF_2Cl$; $OCFCl_2$; $OR^0$; O—C(=O)—$R^0$; O—C(=O)—O—$R^0$; O—(C=O)—NH—$R^0$; O—C(=O)—$N(R^0)_2$; O—S(=O)$_2$—$R^0$; O—S(=O)$_2$—OH; O—S(=O)$_2$—$OR^0$; O—S(=O)$_2$—$NH_2$; O—S(=O)$_2$—$NHR^0$; O—S(=O)$_2$—$N(R^0)_2$; $NH_2$; $NHR^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—$N(R^0)_2$; $NR^0$—C(=O)—$R^0$; $NR^0$—C(=O)—O—H; $NR^0$—C(=O)—$NH_2$; $NR^0$—C(=O)—NH—$R^0$; $NR^0$—C(=O)—$N(R^0)_2$; NH—S(=O)$_2$—OH; NH—S(=O)$_2$—$R^0$; NH—S(=O)$_2$—$OR^0$; NH—S(=O)$_2$—$NH_2$; NH—S(=O)$_2$—$NHR^0$; NH—S(=O)$_2$—$N(R^0)_2$; $NR^0$—S(=O)$_2$—OH; $NR^0$—S(=O)$_2$$R^0$; $NR^0$—S(=O)$_2$—$OR^0$; $NR^0$—S(=O)$_2$—$NH_2$; $NR^0$—S(=O)$_2$—$NHR^0$; $NR^0$—S(=O)$_2$—$N(R^0)_2$; SH; $SCF_3$; $SCF_2H$; $SCFH_2$; $SCF_2Cl$; $SCFCl_2$; $SR^0$; S(=O)—$R^0$; S(=O)$_2$—$R^0$; S(=O)$_2$—OH; S(=O)$_2$—$OR^0$; S(=O)$_2$—$NH_2$; S(=O)$_2$—$NHR^0$; and S(=O)$_2$—$N(R^0)_2$;

optionally in the form of a single stereoisomer or a mixture of stereoisomers, in the form of the free compound and/or a physiologically acceptable salt or a solvate, in particular hydrate, thereof.

DETAILED DESCRIPTION

The term "single stereoisomer" comprises in the sense of this invention an individual enantiomer or diastereomer. The term "mixture of stereoisomers" comprises in the sense of this invention the racemate and mixtures of enantiomers and/or diastereomers in any mixing ratio.

The term "physiologically acceptable salt" comprises in the sense of this invention a salt of at least one compound according to the present invention and at least one physiologically acceptable acid or base.

The terms "$C_{1-10}$ aliphatic residue", "$C_{1-8}$ aliphatic residue", and "$C_{1-4}$ aliphatic residue" comprise in the sense of this invention acyclic saturated or unsaturated aliphatic hydrocarbon residues, which can be branched or unbranched and also unsubstituted or mono- or polysubstituted, which contain 1 to 10, or 1 to 8, or 1 to 4 carbon atoms, respectively, i.e. $C_{1-10}$ alkanyls ($C_{1-10}$ alkyls), $C_{2-10}$ alkenyls and $C_{2-10}$ alkynyls as well as $C_{1-8}$ alkanyls ($C_{1-8}$ alkyls), $C_{2-8}$ alkenyls and $C_{2-8}$ alkynyls as well as $C_{1-4}$ alkanyls ($C_{1-4}$ alkyls), $C_{2-4}$ alkenyls and $C_{2-4}$ alkynyls, respectively. Alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl (alkyl) residues. Preferred $C_{1-10}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{1-8}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-4}$ alkanyl residues are selected from the group consisting of methyl, ethyl, n-propyl, 2-propyl, n-butyl, isobutyl, sec.-butyl and tert.-butyl. Preferred $C_{2-10}$ alkenyl residues are selected from the group consisting of ethenyl (vinyl), propenyl (—CH$_2$CH=CH$_2$, —CH=CH—CH$_3$, —C(=CH$_2$)—CH$_3$), butenyl, pentenyl, hexenyl heptenyl, octenyl, nonenyl and decenyl. Preferred $C_{2-8}$ alkenyl residues are selected from the group consisting of ethenyl (vinyl), propenyl (—CH$_2$CH=CH$_2$, —CH=CH—CH$_3$, —C(=CH$_2$)—CH$_3$), butenyl, pentenyl, hexenyl heptenyl and octenyl. Preferred $C_{2-4}$ alkenyl residues are selected from the group consisting of ethenyl (vinyl), propenyl (—CH$_2$CH=CH$_2$, —CH=CH—CH$_3$, —C(=CH$_2$)—CH$_3$) and butenyl. Preferred $C_{2-10}$ alkynyl residues are selected from the group consisting of ethynyl, propynyl (—CH$_2$—C≡CH, —C≡C—CH$_3$), butynyl, pentynyl, hexynyl, heptynyl, octynyl, nonynyl and decynyl.

Preferred $C_{2-8}$ alkynyl residues are selected from the group consisting of ethynyl, propynyl (—CH$_2$—C≡CH, —C≡C—CH$_3$), butynyl, pentynyl, hexynyl, heptynyl and octynyl. Preferred $C_{2-4}$ alkynyl residues are selected from the group consisting of ethynyl, propynyl (—CH$_2$—C≡CH, —C≡C—CH$_3$) and butynyl.

The terms "$C_{3-6}$ cycloaliphatic residue" and "$C_{3-10}$ cycloaliphatic residue" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. $C_{3-10}$ cycloaliphatic residue can furthermore be singly or multiply bridged such as, for example, in the case of adamantyl, bicyclo[2.2.1]heptyl or bicyclo[2.2.2]octyl. Preferred $C_{3-10}$ cycloaliphatic residues are selected from the group consisting of cyclopropyl, cyclobutyl, cyclopentyl, cyclohexyl, cycloheptyl, cyclooctyl, cyclononyl, cyclodecyl, adamantyl,

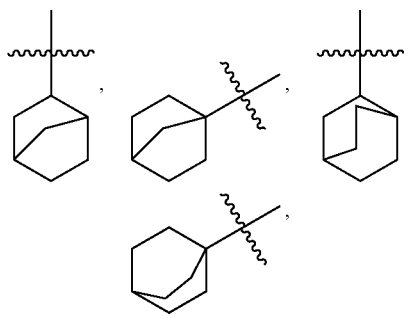

cyclopentenyl, cyclohexenyl, cycloheptenyl and cyclooctenyl. Preferred $C_{3-6}$ cycloaliphatic residues are selected from the group consisting of cyclopropyl, cyclobutyl, cyclopentyl, cyclohexyl, cyclopentenyl and cyclohexenyl. Particularly preferred $C_{3-10}$ cycloaliphatic and $C_{3-6}$ cycloaliphatic residues are $C_{5-6}$ cycloaliphatic residues such as cyclopentyl, cyclohexyl, cyclopentenyl and cyclohexenyl.

The terms "3-6-membered heterocycloaliphatic residue", and "3-10-membered heterocycloaliphatic residue" mean for the purposes of this invention heterocycloaliphatic saturated or unsaturated (but not aromatic) residues having 3-6, i.e. 3, 4, 5 or 6 ring members, and 3-10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O)$_2$, N, NH and N($C_{1-8}$ alkyl) such as N(CH$_3$), preferably are replaced by a heteroatom or a heteroatom group each selected independently of one another from the group consisting of O, S, N, NH and N($C_{1-8}$ alkyl) such as N(CH$_3$), wherein the ring members can be unsubstituted or mono- or polysubstituted. The heterocycloaliphatic residue can be bound to the superordinate general structure via any desired and possible ring member of the heterocycloaliphatic residue if not indicated otherwise. The heterocycloaliphatic residues can also be condensed with further saturated, (partially) unsaturated (hetero)cycloaliphatic or aromatic or heteroaromatic ring systems, i.e. with cycloaliphatic, heterocycloaliphatic, aryl or heteroaryl residues, which can in turn be unsubstituted or mono- or polysubstituted. Preferred heterocycloaliphatic residues are selected from the group consisting of azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, oxazepanyl, pyrrolidinyl, piperazinyl, 4-methylpiperazinyl, piperidinyl, pyrazolidinyl, pyranyl, tetrahydropyrrolyl, tetrahydropyranyl, tetrahydro-2H-pyran-4-yl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazololyl, tetrahydropyridinyl, thiazolidinyl and thiomorpholinyl.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The term "bridged via a $C_{1-4}$ aliphatic group or via a $C_{1-8}$ aliphatic group" with respect to residues as aryl, heteroaryl, a heterocycloaliphatic residue and a cycloaliphatic residue mean for the purpose of the invention that these residues have the above-defined meanings and that each of these residues is bound to the respective superordinate general structure via a $C_{1-4}$ aliphatic group or via a $C_{1-8}$ aliphatic group, respectively. The $C_{1-4}$ aliphatic group and the $C_{1-8}$-aliphatic group can in all cases be branched or unbranched, unsubstituted or mono- or polysubstituted. The $C_{1-4}$ aliphatic group can in all cases be furthermore saturated or unsaturated, i.e. can be a $C_{1-4}$ alkylene group, a $C_{2-4}$ alkenylene group or a $C_{2-4}$ alkynylene group. The same applies to a $C_{1-8}$-aliphatic group, i.e. a $C_{1-8}$-aliphatic group can in all cases be furthermore saturated or unsaturated, i.e. can be a $C_{1-8}$ alkylene group, a $C_{2-8}$ alkenylene group or a $C_{2-8}$ alkynylene group. Preferably, the $C_{1-4}$-aliphatic group is a $C_{1-4}$ alkylene group or a $C_{2-4}$ alkenylene group, more preferably a $C_{1-4}$ alkylene group. Preferably, the $C_{1-8}$-aliphatic group is a $C_{1-8}$ alkylene group or a $C_{2-8}$ alkenylene group, more preferably a $C_{1-8}$ alkylene group. Preferred $C_{1-4}$ alkylene groups are selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$— and —$C(CH_3)(CH_2CH_3)$—. Preferred $C_{2-4}$ alkenylene groups are selected from the group consisting of —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$— and —$C(CH_2CH_3)$=$CH$—. Preferred $C_{2-4}$ alkynylene groups are selected from the group consisting of —$C$≡$C$—, —$C$≡$C$—$CH_2$—, —$C$≡$C$—$CH_2$—$CH_2$—, —$C$≡$C$—$CH(CH_3)$—, —$CH_2$—$C$≡$C$—$CH_2$— and —$C$≡$C$—$C$≡$C$—. Preferred $C_{1-8}$ alkylene groups are selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$CH(CH_2CH_3)$—$CH_2$—$CH_2$—, —$CH_2$—$C(CH_3)_2$—$CH_2$—, —$CH(CH_2CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. Preferred $C_{2-8}$ alkenylene groups are selected from the group consisting of —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$—, —$C(CH_2CH_3)$=$CH$—, —$CH$=$CH$—$CH_2$—$CH_2$—$CH_2$—, —$CH_2$—$CH$=$CH_2$—$CH_2$—$CH_2$—, —$CH$=$CH$=$CH$—$CH_2$—$CH_2$— and —$CH$=$CH_2$—$CH$—$CH$=$CH_2$—. Preferred $C_{2-8}$ alkynylene groups are selected from the group consisting of —$C$≡$C$—, —$C$≡$C$—$CH_2$—, —$C$≡$C$—$CH_2$—$CH_2$—, —$C$≡-$C$—$CH(CH_3)$—, —$CH_2$—$C$≡$C$—$CH_2$—, —$C$≡$C$—$C$≡$C$—, —$C$≡$C$—$C(CH_3)_2$—, —$C$≡$C$—$CH_2$—$CH_2$—$CH_2$—, —$CH_2$—$C$≡$C$—$CH_2$—$CH_2$—, —$C$≡$C$—$C$≡$C$—$CH_2$— and —$C$≡$C$—$CH_2$—$C$≡$C$.

In relation to the terms "aliphatic residue", "aliphatic group", "cycloaliphatic residue" and "heterocycloaliphatic residue", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; $NO_2$; CN; =O; =NH; =N(OH); =$C(NH_2)_2$; $CF_3$; $CF_2H$; $CFH_2$; $CF_2Cl$; $CFCl_2$; C(=O)—H; C(=O)—$R^0$; C(=O)—OH; C(=O)—$OR^0$; CO—$NH_2$; C(=O)—$NHR^0$; C(=O)—$N(R^0)_2$; OH; $OCF_3$; $OCF_2H$; $OCFH_2$; $OCF_2Cl$; $OCFCl_2$; $OR^0$; O—C(=O)—$R^0$; O—C(=O)—O—$R^0$; O—(C=O)—NH—$R^0$; O—C(=O)—$N(R^0)_2$; O—$S(=O)_2$—$R^0$; O—$S(=O)_2$—OH; O—$S(=O)_2$—$OR^0$; O—$S(=O)_2$—$NH_2$; O—$S(=O)_2$—$NHR^0$; O—$S(=O)_2$—$N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—$NHR^0$; NH—C(=O)—$N(R^0)_2$; $NR^0$—C(=O)—$R^0$; $NR^0$—C(=O)—O—$R^0$; $NR^0$—C(=O)—$NH_2$; $NR^0$—C(=O)—$NHR^0$; $NR^0$—C(=O)—$N(R^0)_2$; NH—$S(=O)_2$—OH; NH—$S(=O)_2$—$R^0$; NH—$S(=O)_2$—$OR^0$; NH—$S(=O)_2$—$NH_2$; NH—$S(=O)_2$—$NHR^0$; NH—$S(=O)_2$—$N(R^0)_2$; $NR^0$—$S(=O)_2$—OH; $NR^0$—$S(=O)_2$—$R^0$; $NR^0$—$S(=O)_2$—$OR^0$; $NR^0$—$S(=O)_2$—$NH_2$; $NR^0$—$S(=O)_2$—$NHR^0$; $NR^0$—$S(=O)_2$—$N(R^0)_2$; SH; $SCF_3$; $SCF_2H$; $SCFH_2$; $SCF_2Cl$; $SCFCl_2$; SW; S(=O)—$R^0$; $S(=O)_2$—$R^0$; $S(=O)_2$—OH; $S(=O)_2$—$OR^0$; $S(=O)_2$—$NH_2$; $S(=O)_2$—$NHR^0$; and $S(=O)_2$—$N(R^0)_2$. The term "polysubstituted" with respect to polysubstituted residues and groups includes the polysubstitution of these residues and groups either on different or on the same atoms, for example trisubstituted on the same carbon atom, as in the case of $CF_3$, $CH_2CF_3$ or 1,1-difluorocyclohexyl, or at various points, as in the case of CH(OH)—CH=CH—$CHCl_2$ or 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group" are selected from the group consisting of F; Cl; Br; I;

NO$_2$; CF$_3$; CN; =O; =NH; R$^o$; (C$_{1-8}$ alkylene)-OH; C(=O)(R$^o$ or H); C(=O)O(R$^o$ or H); C(=O)N(R$^o$ or H)$_2$; OH; OR$^o$; O—C(=O)—R$^o$; O—(C$_{1-8}$ alkylene)-OH; O—(C$_{1-8}$ alkylene)-O—C$_{1-8}$ alkyl; OCF$_3$; N(R$^o$ or H)$_2$; N(R$^o$ or H)—C(=O)—R$^o$; N(R$^o$ or H)—S(=O)$_2$—R$^o$; N(R$^o$ or H)—C(=O)—N(R$^o$ or H)$_2$; SH; SCF$_3$; SR$^o$; S(=O)$_2$R$^o$; S(=O)$_2$O(R$^o$ or H) and S(=O)$_2$—N(R$^o$ or H)$_2$.

Particularly preferred substituents of "aliphatic residue" and "aliphatic group" are selected from the group consisting of F; Cl; Br; I; NO$_2$; CF$_3$; CN; =O; C$_{1-8}$ aliphatic residue; aryl; heteroaryl; C$_{3-6}$ cycloaliphatic residue; 3 to 6 membered heterocycloaliphatic residue; aryl, heteroaryl, C$_{3-6}$ cycloaliphatic residue or 3 to 6 membered heterocycloaliphatic bridged via a C$_{1-4}$ aliphatic group; CHO; C(=O)—C$_{1-8}$ aliphatic residue; C(=O)aryl; C(=O)heteroaryl; CO$_2$H; C(=O)O—C$_{1-8}$ aliphatic residue; C(=O)O-aryl; C(=O)O-heteroaryl; C(=O)—NH$_2$; C(=O)NH—C$_{1-8}$ aliphatic residue; C(=O)N(C$_{1-8}$ aliphatic residue)$_2$; C(=O)NH-aryl; C(=O)N(aryl)$_2$; C(=O)NH-heteroaryl; C(=O)N(heteroaryl)$_2$; C(=O)N(C$_{1-8}$ aliphatic residue)(aryl); C(=O)N(C$_{1-8}$ aliphatic residue)(heteroaryl); C(=O)N(heteroaryl)(aryl); OH; O—C$_{1-8}$ aliphatic residue; OCF$_3$; O—(C$_{1-8}$ aliphatic residue)-OH; O—(C$_{1-8}$ aliphatic group)-O—C$_{1-8}$ aliphatic residue; O-benzyl; O-aryl; O-heteroaryl; O—C(=O)—C$_{1-8}$ aliphatic residue; O—C(=O)aryl; O—C(=O)heteroaryl; NH$_2$; NH—C$_{1-8}$ aliphatic residue; NH—(C$_{1-8}$ aliphatic group)-OH; N(C$_{1-8}$ aliphatic residue)[(C$_{1-8}$ aliphatic group)-OH]; N(C$_{1-8}$ aliphatic residue)$_2$; NH—C(=O)—C$_{1-8}$ aliphatic residue; NH—S(=O)$_2$—C$_{1-8}$ aliphatic residue; N(C$_{1-8}$ aliphatic residue)[S(=O)$_2$—C$_{1-8}$ aliphatic residue]; NH—S(=O)$_2$—NH$_2$; NH—C(=O)-aryl; NH—C(=O)-heteroaryl; SH; S—C$_{1-8}$ aliphatic residue; SCF$_3$; S-benzyl; S-aryl; S-heteroaryl; S(=O)$_2$—C$_{1-8}$ aliphatic residue; S(=O)$_2$ aryl; S(=O)$_2$ heteroaryl; S(=O)$_2$OH; S(=O)$_2$O—C$_{1-8}$ aliphatic residue; S(=O)$_2$O-aryl; S(=O)$_2$O-heteroaryl; S(=O)$_2$—NH—C$_{1-8}$ aliphatic residue; S(=O)$_2$—NH-aryl; and S(=O)$_2$—NH-heteroaryl.

Most preferred substituents of "aliphatic residue" and "aliphatic group" are selected from the group consisting of F; Cl; Br; I; CF$_3$; C(=O)—NH$_2$; C(=O)NH—C$_{1-8}$ aliphatic residue; C(=O)N(C$_{1-8}$ aliphatic residue)$_2$; OH; O—C$_{1-8}$ aliphatic residue; O—(C$_{1-8}$ aliphatic residue)-OH; O—(C$_{1-8}$ aliphatic group)-O—C$_{1-8}$ aliphatic residue; NH$_2$; NH—C$_{1-8}$ aliphatic residue; N(C$_{1-8}$ aliphatic residue)$_2$; NH—(C$_{1-8}$ aliphatic group)-OH; N(C$_{1-8}$ aliphatic residue)[(C$_{1-8}$ aliphatic group)-OH]; NH—C(=O)—C$_{1-8}$ aliphatic residue; NH—S(=O)$_2$—C$_{1-8}$ aliphatic residue; N(C$_{1-8}$ aliphatic residue)[S(=O)$_2$—C$_{1-8}$ aliphatic residue]; NH—S(=O)$_2$—NH$_2$; SH; S—C$_{1-8}$ aliphatic residue; S(=O)$_2$—C$_{1-8}$ aliphatic residue; and S(=O)$_2$—NH—C$_{1-8}$ aliphatic residue.

Preferred substituents of "cycloaliphatic residue" and "heterocycloaliphatic residue" are selected from the group consisting of F; Cl; Br; I; NO$_2$; CF$_3$; CN; =O; =NH; R$^o$; C(=O)(R$^o$ or H); C(=O)O(R$^o$ or H); C(=O)N(R$^o$ or H)$_2$; OH; OR$^o$; O—C(=O)—R$^o$; O—(C$_{1-8}$ alkyl)-OH; O—(C$_{1-8}$ alkyl)-O—C$_{1-8}$ alkyl; OCF$_3$; N(R$^o$ or H)$_2$; N(R$^o$ or H)—C(=O)—R$^o$; N(R$^o$ or H)—S(=O)$_2$—R$^o$; N(R$^o$ or H)—C(=O)—N(R$^o$ or H)$_2$; SH; SCF$_3$; SR$^o$; S(=O)$_2$R$^o$; S(=O)$_2$O(R$^o$ or H) and S(=O)$_2$—N(R$^o$ or H)$_2$.

Particularly preferred substituents of "cycloaliphatic residue" and "heterocycloaliphatic residue" are selected from the group consisting of F; Cl; Br; I; NO$_2$; CF$_3$; CN; =O; C$_{1-8}$ aliphatic residue; aryl; heteroaryl; C$_{3-6}$ cycloaliphatic residue; 3 to 6 membered heterocycloaliphatic residue; aryl, heteroaryl, C$_{3-6}$ cycloaliphatic residue or 3 to 6 membered heterocycloaliphatic bridged via a C$_{1-4}$ aliphatic group; CHO; C(=O)—C$_{1-8}$ aliphatic residue; C(=O)aryl; C(=O)heteroaryl; CO$_2$H; C(=O)O—C$_{1-8}$ aliphatic residue; C(=O)O-aryl; C(=O)O-heteroaryl; CONH$_2$; C(=O)NH—C$_{1-8}$ aliphatic residue; C(=O)N(C$_{1-8}$ aliphatic residue)$_2$; C(=O)NH-aryl; C(=O)N(aryl)$_2$; C(=O)NH-heteroaryl; C(=O)N(heteroaryl)$_2$; C(=O)N(C$_{1-8}$ aliphatic residue)(aryl); C(=O)N(C$_{1-8}$ aliphatic residue)(heteroaryl); C(=O)N(heteroaryl)(aryl); OH; O—C$_{1-8}$ aliphatic residue; OCF$_3$; O—(C$_{1-8}$ aliphatic group)-OH; O—(C$_{1-8}$ aliphatic group)-O—C$_{1-8}$ aliphatic residue; O-benzyl; O-aryl; O-heteroaryl; O—C(=O)—C$_{1-8}$ aliphatic residue; O—C(=O)aryl; O—C(=O)heteroaryl; NH$_2$; NH—C$_{1-8}$ aliphatic residue; N(C$_{1-8}$ aliphatic residue)$_2$; NH—C(=O)—C$_{1-8}$ aliphatic residue; NH—C(=O)-aryl; NH—C(=O)-heteroaryl; SH; S—C$_{1-8}$ aliphatic residue; SCF$_3$; S-benzyl; S-aryl; S-heteroaryl; S(=O)$_2$—C$_{1-8}$ aliphatic residue; S(=O)$_2$ aryl; S(=O)$_2$ heteroaryl; S(=O)$_2$OH; S(=O)$_2$O—C$_{1-8}$ aliphatic residue; S(=O)$_2$O-aryl; S(=O)$_2$O-heteroaryl; S(=O)$_2$—NH—C$_{1-8}$ aliphatic residue; S(=O)$_2$—NH-aryl; and S(=O)$_2$—NH-heteroaryl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; CF$_3$; CF$_2$H; CFH$_2$; CF$_2$Cl; CFCl$_2$; R$^o$; C(=O)—H; C(=O)—R$^o$; C(=O)—OH; C(=O)—OR$^o$; CO—NH$_2$; C(=O)—NHR$^o$; C(=O)—N(R$^o$)$_2$; OH; OCF$_3$; OCF$_2$H; OCFH$_2$; OCF$_2$Cl; OCFCl$_2$; OR$^o$; O—C(=O)—R$^o$; O—C(=O)—O—R$^o$; O—(C=O)—NH—R$^o$; O—C(=O)—N(R$^o$)$_2$; O—S(=O)$_2$—R$^o$; O—S(=O)$_2$—OH; O—S(=O)$_2$—OR$^o$; O—S(=O)$_2$—NH$_2$; O—S(=O)$_2$—NHR$^o$; O—S(=O)$_2$—N(R$^o$)$_2$; NH$_2$; NHR$^o$; N(R$^o$)$_2$; NH—C(=O)—R$^o$; NH—C(=O)—O—R$^o$; NH—C(=O)—NH$_2$; NH—C(=O)—NH—R$^o$; NH—C(=O)—N(R$^o$)$_2$; NR$^o$—C(=O)—R$^o$; NR$^o$—C(=O)—O—R$^o$; NR$^o$—C(=O)—NH$_2$; NR$^o$—C(=O)—NH—R$^o$; NR$^o$—C(=O)—N(R$^o$)$_2$; NH—S(=O)$_2$—OH; NH—S(=O)$_2$—R$^o$; NH—S(=O)$_2$—OR$^o$; NH—S(=O)$_2$—NH$_2$; NH—S(=O)$_2$—NHR$^o$; NH—S(=O)$_2$—N(R$^o$)$_2$; NR$^o$—S(=O)$_2$—OH; NR$^o$—S(=O)$_2$R$^o$; NR$^o$—S(=O)$_2$—OR$^o$; NR$^o$—S(=O)$_2$—NH$_2$; NR$^o$—S(=O)$_2$—NHR$^o$; NR$^o$—S(=O)$_2$—N(R$^o$)$_2$; SH; SCF$_3$; SCF$_2$H; SCFH$_2$; SCF$_2$Cl; SCFCl$_2$; SR$^o$; S(=O)—R$^o$; S(=O)$_2$—R$^o$; S(=O)$_2$—OH; S(=O)$_2$—OR$^o$; S(=O)$_2$—NH$_2$; S(=O)$_2$—NHR$^o$; and S(=O)$_2$—N(R$^o$)$_2$;

Preferred substituents of "aryl" and "heteroaryl" are selected from the group consisting of F; Cl; Br; I; NO$_2$; CF$_3$; CN; C(=O)(R$^o$ or H); C(=O)O(R$^o$ or H); C(=O)N(R$^o$ or H)$_2$; OH; OR$^o$; O—C(=O)—R$^o$; O—(C$_{1-8}$ alkyl)-O—C$_{1-8}$ alkyl; OCF$_3$; N(R$^o$ or H)$_2$; N(R$^o$ or H)—C(=O)—R$^o$; N(R$^o$ or H)—S(=O)$_2$—R$^o$; N(R$^o$ or H)—C(=O)—N(R$^o$ or H)$_2$; SH; SCF$_3$; SR$^o$; S(=O)$_2$R$^o$; S(=O)$_2$O(R$^o$ or H) and S(=O)$_2$—N(R$^o$ or H)$_2$.

Particularly preferred substituents of "aryl" and "heteroaryl" are selected from the group consisting of F; Cl; Br; I; NO$_2$; CF$_3$; CN; C$_{1-8}$ aliphatic residue; aryl; heteroaryl; C$_{3-6}$ cycloaliphatic residue; 3 to 6 membered heterocycloaliphatic residue; aryl, heteroaryl, C$_{3-6}$ cycloaliphatic residue or 3 to 6 membered heterocycloaliphatic bridged via a C$_{1-4}$ aliphatic group; CHO; C(=O)—C$_{1-8}$ aliphatic residue; C(=O)aryl; C(=O)heteroaryl; CO$_2$H; C(=O)O—C$_{1-8}$ aliphatic residue; C(=O)O-aryl; C(=O)O-heteroaryl; CONH$_2$; C(=O)NH—C$_{1-8}$ aliphatic residue; C(=O)N(C$_{1-8}$ aliphatic residue)$_2$; C(=O)NH-aryl; C(=O)N(aryl)$_2$; C(=O)NH-heteroaryl; C(=O)N(heteroaryl)$_2$; C(=O)N(C$_{1-8}$ aliphatic residue)

(aryl); C(=O)N($C_{1-8}$ aliphatic residue)(heteroaryl); C(=O) N(heteroaryl)(aryl); OH; O—$C_{1-8}$ aliphatic residue; $OCF_3$; O—($C_{1-8}$ aliphatic group)-OH; O—($C_{1-8}$ aliphatic group)-O—$C_{1-8}$ aliphatic residue; O-benzyl; O-aryl; O-heteroaryl; O—C(=O)—$C_{1-3}$ aliphatic residue; O—C(=O)aryl; O—C(=O)heteroaryl; $NH_2$; NH—$C_{1-8}$ aliphatic residue; N($C_{1-8}$ aliphatic residue)$_2$; NH—C(=O)—$C_{1-8}$ aliphatic residue; NH—C(=O)-aryl; NH—C(=O)-heteroaryl; SH; S—$C_{1-8}$ aliphatic residue; $SCF_3$; S-benzyl; S-aryl; S-heteroaryl; S(=O)$_2$—$C_{1-8}$ aliphatic residue; S(=O)$_2$ aryl; S(=O)$_2$ heteroaryl; S(=O)$_2$OH; S(=O)$_2$O—$C_{1-8}$ aliphatic residue; S(=O)$_2$O-aryl; S(=O)$_2$O-heteroaryl; S(=O)$_2$—NH—$C_{1-8}$ aliphatic residue; S(=O)$_2$—NH-aryl; and S(=O)$_2$—NH-heteroaryl.

The compounds according to the invention are defined by substituents, for example by $R^1$, $R^2$ and $R^3$ ($1^{st}$ generation substituents) which are for their part if appropriate themselves substituted ($2^{nd}$ generation substituents). Depending on the definition, these substituents of the substituents can for their part be resubstituted ($3^{rd}$ generation substituents). If, for example, $R^1$=a $C_{1-4}$ aliphatic residue ($1^{st}$ generation substituent), then the $C_{1-4}$ aliphatic residue can for its part be substituted, for example with a NH—$C_{1-4}$ aliphatic residue ($2^{nd}$ generation substituent). This produces the functional group $R^1$=($C_{1-4}$ aliphatic residue-NH—$C_{1-4}$ aliphatic residue). The NH—$C_{1-4}$ aliphatic residue can then for its part be resubstituted, for example with Cl ($3^{rd}$ generation substituent). Overall, this produces the functional group $R^1$=$C_{1-4}$ aliphatic residue-NH—$C_{1-4}$ aliphatic residue, wherein the $C_{1-4}$ aliphatic residue of the NH—$C_{1-4}$ aliphatic residue is substituted by Cl.

However, in a preferred embodiment, the $3^{rd}$ generation substituents may not be resubstituted, i.e. there are then no $4^{th}$ generation substituents.

In another preferred embodiment, the $2^{nd}$ generation substituents may not be resubstituted, i.e. there are then not even any $3^{rd}$ generation substituents. In other words, in this embodiment, in the case of general formula (I), for example, the functional groups for $R^1$ to $R^9$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, in each case unsubstituted or mono- or polysubstituted. Both these aryl or heteroaryl residues and the (hetero)aromatic ring systems formed in this way can if appropriate be condensed with a cycloaliphatic, preferably a $C_{3-6}$ cycloaliphatic residue, or heterocycloaliphatic residue, preferably a 3 to 6 membered heterocycloaliphatic residue, or with aryl or heteroaryl, e.g. with a $C_{3-6}$ cycloaliphatic residue such as cyclopentyl, or a 3 to 6 membered heterocycloaliphatic residue such as morpholinyl, or an aryl such as phenyl, or a heteroaryl such as pyridyl, wherein the cycloaliphatic or heterocycloaliphatic residues, aryl or heteroaryl residues condensed in this way can for their part be respectively unsubstituted or mono- or polysubstituted.

In some cases, the compounds according to the invention are defined by substituents which are or carry a cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with aryl or heteroaryl, preferably selected from the group consisting of phenyl, pyridyl and thienyl, or with a cycloaliphatic residue, preferably a $C_{3-6}$ cycloaliphatic residue, or a heterocycloaliphatic residue, preferably a 3 to 6 membered heterocycloaliphatic residue, e.g. with an aryl such as phenyl, or a heteroaryl such as pyridyl, or a cycloaliphatic residue such as cyclohexyl, or a heterocycloaliphatic residue such as morpholinyl, wherein the aryl or heteroaryl residues or cycloaliphatic or heterocycloaliphatic residues condensed in this way can for their part be respectively unsubstituted or mono- or polysubstituted.

Within the scope of the present invention, the symbol

used in the formulas denotes a link of a corresponding residue to the respective superordinate general structure.

If a residue occurs multiple times within a molecule, then this residue can have respectively different meanings for various substituents: if, for example, both $R^1$ and $R^2$ denote a 3 to 6 membered heterocycloaliphatic residue, then the 3 to 6 membered heterocycloaliphatic residue can e.g. represent morpholinyl for $R^1$ and can represent piperazinyl for $R^2$.

If a residue occurs multiply within a molecule, such as for example the residue $R^0$, then this residue can have respectively different meanings for various substituents.

The term "($R^0$ or H)" within a residue means that $R^0$ and H can occur within this residue in any possible combination. Thus, for example, the residue "N($R^0$ or H)$_2$" can represent "$NH_2$", "$NHR^0$" and "N($R^0$)$_2$". If, as in the case of "N($R^0$)$_2$", $R^0$ occurs multiply within a residue, then $R^0$ can respectively have the same or different meanings: in the present example of "N($R^0$)$_2$", $R^0$ can for example represent aryl twice, thus producing the functional group "N(aryl)$_2$", or $R^0$ can represent once aryl and once a $C_{1-10}$ aliphatic residue, thus producing the functional group "N(aryl)($C_{1-10}$ aliphatic residue)".

The terms "salt formed with a physiologically compatible acid" or "salt of physiologically acceptable acids" refers in the sense of this invention to salts of the respective active ingredient with inorganic or organic acids which are physiologically compatible—in particular when used in human beings and/or other mammals. Examples of physiologically acceptable acids are: hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

The terms "salt formed with a physiologically compatible base" or "salt of physiologically acceptable bases" refers in the sense of this invention to salts of the respective compound according to the invention—as an anion, e.g. upon deprotonation of a suitable functional group—with at least one cation or base—preferably with at least one inorganic cation—which are physiologically acceptable—in particular when used in human beings and/or other mammals. Particularly preferred are the salts of the alkali and alkaline earth metals, in particular (mono-) or (di)sodium, (mono-) or (di)potassium, magnesium or calcium salts, but also ammonium salts $[NH_xR_{4-x}]^+$, in which x=0, 1, 2, 3 or 4 and R represents a branched or unbranched $C_{1-4}$ aliphatic residue.

The term "inhibition" in the sense of the present invention means to retard or lessen.

In a preferred embodiment of the present invention the compound according to general formula (I) has the general formula (I-a)

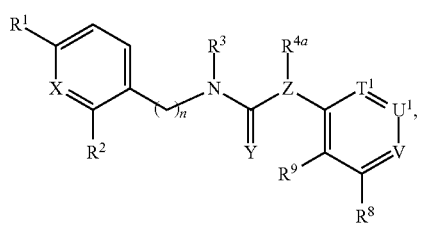
(I-a)

wherein
$R^1$-$R^3$, $R^{4a}$, $R^8$, $R^9$, X, n, Y, V, $T^1$, $U^1$ and Z have the meanings described herein in connection with the compounds according to the invention and preferred embodiments thereof.

In a further preferred embodiment of the present invention the inventive compound has the general formula (I), wherein $R^1$-$R^3$, $R^{4a}$, X, n, Y, $T^1$, $U^1$, V, $U^2$, $T^2$ and Z have the above defined meanings, with the proviso that, if $T^1$ represents C—$R^5$, $U^1$ represents C—$R^6$, V denotes C—$R^7$, $U^2$ represents $CR^8$ and $T^2$ denotes $CR^9$, $R^5$ and $R^6$ together or $R^6$ and $R^7$ together or $R^7$ and $R^8$ together or $R^8$ and $R^9$ together, in each case independently of one another, together with the carbon atoms connecting them form a 3 to 10 membered heterocycloaliphatic residue, preferably a 3 to 6 membered heterocycloaliphatic residue, unsubstituted or mono- or polysubstituted, or form a heteroaryl, unsubstituted or mono- or polysubstituted, and the respective remaining substituents of $R^5$, $R^6$, $R^7$, $R^8$, and $R^9$ each independently of one another have one of the above defined meanings.

In a further preferred embodiment of the present invention the inventive compound has the general formula (I), wherein $R^1$-$R^3$, $R^{4a}$, X, n, Y, $T^1$, $U^1$, V, $U^2$, $T^2$ and Z have the above defined meanings, with the proviso that, if $R^2$ denotes O—$R^0$S—$R^0$, NH($R^0$) or N($R^0$)$_2$ and $R^0$ represents a 3 to 10 membered heterocycloaliphatic residue or a heteroaryl, the 3 to 10 membered heterocycloaliphatic residue or the heteroaryl is bound via a carbon atom as a ring member of each of these residues to the oxygen, sulfur or nitrogen atom of O—$R^0$S—$R^0$, NH($R^0$) and N($R^0$)$_2$, respectively.

Further preferred embodiments of the compound according to the invention of general formula (I) have general formulae (I-b), (I-c), (I-d) and/or (I-e):

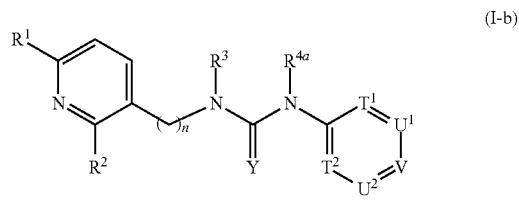
(I-b)

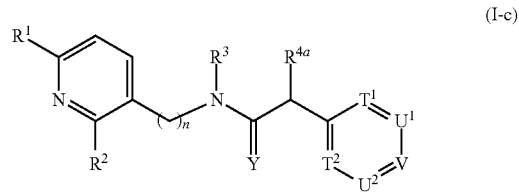
(I-c)

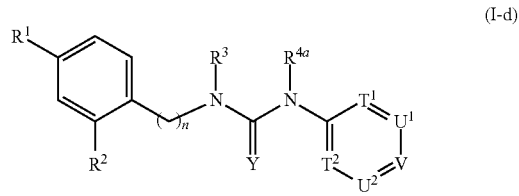
(I-d)

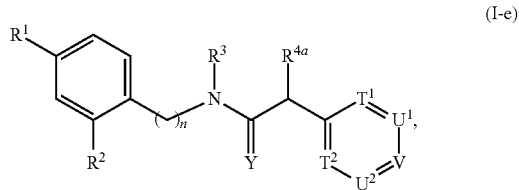
(I-e)

wherein the particular radicals, variables and indices have the meanings described herein in connection with the compounds according to the invention and preferred embodiments thereof.

Compounds of general formula (Ib) are most particularly preferred.

Further preferred embodiments of the compound according to the invention of general formula (I) have general formulae (I-f), (I-g), (I-h) and/or (I-i):

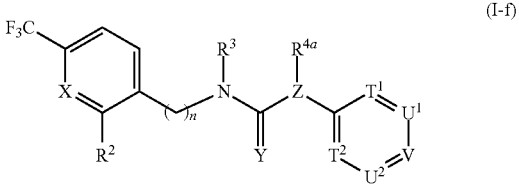
(I-f)

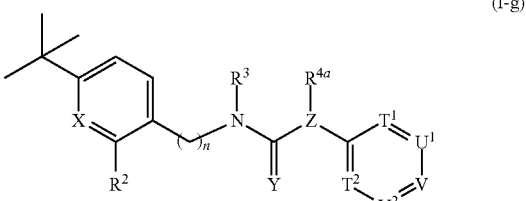
(I-g)

-continued

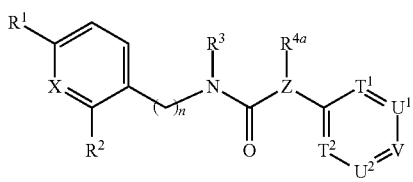

(I-h)

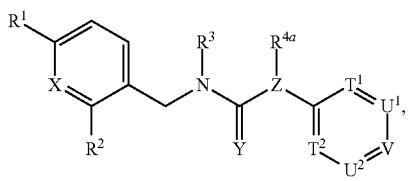

(I-i)

wherein the particular radicals, variables and indices have the meanings described herein in connection with the compounds according to the invention and preferred embodiments thereof.

Moreover, preferred embodiments of the compound according to the invention of general formula (I) have general formulae (I-j), (I-k), (I-l) and/or (I-m):

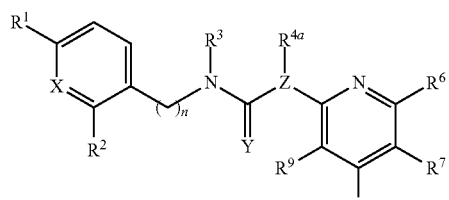

(I-j)

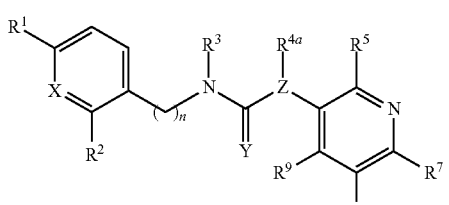

(I-k)

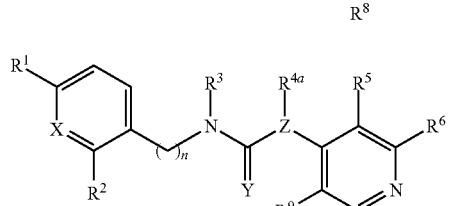

(I-l)

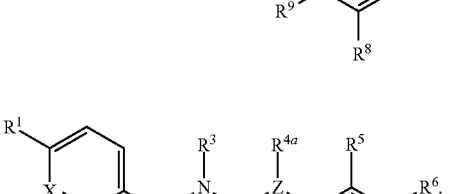

(I-m)

wherein the particular radicals, variables and indices have the meanings described herein in connection with the compounds according to the invention and preferred embodiments thereof.

In a particular preferred embodiment of the present invention
$R^1$-$R^3$, $R^{4a}$, X, n, Y, $T^1$, $U^1$, V, $U^2$, $1^2$ and Z have the meanings described herein in connection ith the compounds according to the invention and preferred embodiments thereof,
with the proviso that 0, 1, or 2, preferably 0 or 1, of variables $T^1$, $U^1$, V, $U^2$ and $T^2$ represent a nitrogen atom simultaneously, and
$R^5$ and $R^6$ together or
$R^6$ and $R^7$ together or
$R^7$ and $R^8$ together or
$R^8$ and $R^9$ together,
in each case independently of one another, together with the carbon atoms connecting them
form a $C_{3-10}$-cycloaliphatic residue, preferably a $C_{3-6}$-cycloaliphatic residue, unsubstituted or mono- or polysubstituted,
or a 3 to 10 membered heterocycloaliphatic residue, preferably a 3 to 6 membered heterocycloaliphatic residue, unsubstituted or mono- or polysubstituted,
or form an aryl, unsubstituted or mono- or polysubstituted;
or form a heteroaryl, unsubstituted or mono- or polysubstituted;
with the exception that
$R^5$ and $R^6$ together or
$R^6$ and $R^7$ together or
$R^7$ and $R^8$ together or
$R^8$ and $R^9$ together,
in each case independently of one another, together with the carbon atoms connecting them cannot form a dihydropyrazolyl and/or a pyrazolyl, i.e. cannot form a dihydropyrazolyl or cannot form a pyrazolyl or cannot form both a dihydropyrazolyl and a pyrazolyl,
and the respective remaining substituents of $R^5$, $R^6$, $R^7$, $R^8$, and $R^9$ each independently of one another represent H; F; Cl; Br; I; CN; $CF_3$; $CF_2H$; $CFH_2$; $CF_2Cl$; $CFCl_2$; $NO_2$; $R^0$; C(=O)—H; C(=O)—$R^0$; C(=O)—OH; C(=O)—$OR^0$; C(=O)—$NH_2$; C(=O)—$NHR^0$; C(=O)—$N(R^0)_2$; OH; $OCF_3$; $OCF_2H$; $OCFH_2$; $OCF_2Cl$; $OCFCl_2$; $OR^0$; O—C(=O)—$R^0$; O—C(=O)—O—$R^0$; O—(C=O)—$NHR^0$; O—C(=O)—$N(R^0)_2$; O—S(=O)_2—$R^0$; O—S(=O)_2—OH; O—S(=O)_2—$OR^0$; O—S(=O)_2—$NH_2$; O—S(=O)_2—$NHR^0$; O—S(=O)_2—$N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—$N(R^0)_2$; $NR^0$—C(=O)—$R^0$; $NR^0$—C(=O)—O—$R^0$; $NR^0$—C(=O)—$NH_2$; $NR^0$—C(=O)—$NHR^0$; $NR^0$—C(=O)—$N(R^0)_2$; NH—S(=O)_2—OH; NH—S(=O)_2—$R^0$; NH—S(=O)_2—$OR^0$; NH—S(=O)_2—$NH_2$; NH—S(=O)_2—$NHR^0$; NH—S(=O)_2—$N(R^0)_2$; $NR^0$—S(=O)_2—OH; $NR^0$—S(=O)_2—$R^0$; $NR^0$—S(=O)_2—$OR^0$; $NR^0$—S(=O)_2—$NH_2$; $NR^0$—S(=O)_2—$NHR^0$; $NR^0$—S(=O)_2—$N(R^0)_2$; SH; $SCF_3$; $SCF_2H$; $SCFH_2$; $SCF_2Cl$; $SCFCl_2$; $SR^0$; S(=O)—$R^0$; S(=O)_2—$R^0$; S(=O)_2—OH; S(=O)_2—$OR^0$; S(=O)_2—$NH_2$; S(=O)_2—$NHR^0$; or S(=O)_2—$N(R^0)_2$ or have the meanings described herein in connection with the compounds according to the invention and preferred embodiments thereof.

In the sense of the present invention, the term "with the exception that $R^5$ and $R^6$ together or $R^6$ and $R^7$ together or $R^7$ and $R^8$ together or $R^8$ and $R^9$ together, in each case independently of one another, together with the carbon atoms connecting them cannot form a dihydropyrazolyl and/or a pyrazolyl" preferably means that none of the pairs of substituents $R^5$ and $R^6$ together or $R^6$ and $R^7$ together or $R^7$ and $R^8$ together or $R^8$ and $R^9$ together, in each case independently of one another, together with the carbon atoms connecting them can form a dihydropyrazolyl and/or a pyrazolyl moiety,
e.g. means that the part structure

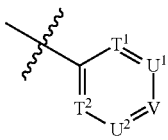

within general formula (I) can in particular not represent the part structure

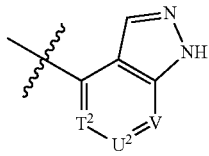

such as part structure

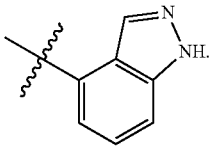 [SMILES: *c1cccc2[nH]ncc12]

In another particular preferred embodiment of the present invention
$R^1$-$R^3$, $R^{4a}$, X, n, Y, $T^1$, $U^1$, V, $U^2$, $T^2$ and Z have the meanings described herein in connection with the compounds according to the invention and preferred embodiments thereof,
with the proviso that 0, 1, or 2, preferably 0 or 1, of variables $T^1$, $U^1$, V, $U^2$ and $T^2$ represent a nitrogen atom simultaneously, and
$R^5$ and $R^6$ together or
$R^6$ and $R^7$ together or
$R^7$ and $R^8$ together or
$R^8$ and $R^9$ together,
in each case independently of one another, together with the carbon atoms connecting them
form a $C_{3-10}$-cycloaliphatic residue, preferably a $C_{3-6}$-cycloaliphatic residue, unsubstituted or mono- or polysubstituted,
or a 3 to 10 membered heterocycloaliphatic residue or a 3 to 6 membered heterocycloaliphatic residue, unsubstituted or mono- or polysubstituted, more preferably selected from the group consisting of azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, oxazepanyl, pyrrolidinyl, piperazinyl, 4-methylpiperazinyl, piperidinyl, pyrazolidinyl, pyranyl, tetrahydropyrrolyl, tetrahydropyranyl, tetrahydro-2H-pyran-4-yl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazololyl, tetrahydropyridinyl, thiazolidinyl and thiomorpholinyl, in each case unsubstituted or mono- or polysubstituted, even more preferably selected from the group consisting of pyrrolidinyl, piperazinyl, 4-methylpiperazinyl, piperidinyl, pyrazolidinyl, pyranyl, tetrahydropyrrolyl, tetrahydropyranyl, morpholinyl, imidazolidinyl, dihydrofuranyl, dioxanyl and dioxolanyl, in each case unsubstituted or mono- or polysubstituted,
or form an aryl, unsubstituted or mono- or polysubstituted;
or form a heteroaryl, unsubstituted or mono- or polysubstituted, preferably selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl, in each case unsubstituted or mono- or polysubstituted, more preferably selected from the group consisting of pyrazinyl, pyrimidinyl, pyridyl, oxazolyl, thiazolyl, pyrrolyl, imidazolyl, isoxazoyl, isothiazolyl, oxadiazolyl, pyrrolyl, pyridazinyl, purinyl, and thiadiazolyl, in each case unsubstituted or mono- or polysubstituted,
and the respective remaining substituents of $R^5$, $R^6$, $R^7$, $R^8$, and $R^9$ each independently of one another represent H; F; Cl; Br; I; CN; $CF_3$; $CF_2H$; $CFH_2$; $CF_2Cl$; $CFCl_2$; $NO_2$; $R^0$; C(=O)—H; C(=O)—$R^0$; C(=O)—OH; C(=O)—$OR^0$; C(=O)—$NH_2$; C(=O)—$NHR^0$; C(=O)—$N(R^0)_2$; OH; $OCF_3$; $OCF_2H$; $OCFH_2$; $OCF_2Cl$; $OCFCl_2$; $OR^0$; O—C(=O)—$R^0$; O—C(=O)—O—$R^0$; O—(C=O)—$NHR^0$; O—C(=O)—$N(R^0)_2$; O—S(=O)$_2$—$R^0$; O—S(=O)$_2$—OH; O—S(=O)$_2$—$OR^0$; O—S(=O)$_2$—$NH_2$; O—S(=O)$_2$—$NHR^0$; O—S(=O)$_2$—$N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—$N(R^0)_2$; $NR^0$—C(=O)—$R^0$; $NR^0$—C(=O)—O—$R^0$; $NR^0$—C(=O)—$NH_2$; $NR^0$—C(=O)—$NHR^0$; $NR^0$—C(=O)—$N(R^0)_2$; NH—S(=O)$_2$—OH; NH—S(=O)$_2$—$R^0$; NH—S(=O)$_2$—$OR^0$; NH—S(=O)$_2$—$NH_2$; NH—S(=O)$_2$—$NHR^0$; NH—S(=O)$_2$—$N(R^0)_2$; $NR^0$—S(=O)$_2$—OH; $NR^0$—S(=O)$_2$—$R^0$; $NR^0$—S(=O)$_2$—$OR^0$; $NR^0$—S(=O)$_2$—$NH_2$; $NR^0$—S(=O)$_2$—$NHR^0$; $NR^0$—S(=O)$_2$—$N(R^0)_2$; SH; $SCF_3$; $SCF_2H$; $SCFH_2$; $SCF_2Cl$; $SCFCl_2$; $SR^0$; S(=O)—$R^0$; S(=O)$_2$—$R^0$; S(=O)$_2$—OH; S(=O)$_2$—$R^0$; S(=O)$_2$—$NH_2$; S(=O)$_2$—$NHR^0$; or S(=O)$_2$—$N(R^0)_2$ or have the meanings described herein in connection with the compounds according to the invention and preferred embodiments thereof.

In a preferred embodiment of the compound of general formula (I) according to the present invention X represents N.

In another preferred embodiment of the compound of general formula (I) according to the present invention X represents CH.

In another preferred embodiment of the compound of general formula (I) according to the present invention
$R^1$ represents a $C_{1-4}$ aliphatic residue, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, NH($C_{1-4}$ alkyl), N($C_{1-4}$ alkyl)$_2$, SH, S—$C_{1-4}$ alkyl, $SCF_3$S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH, or represents a $C_{3-6}$ cycloaliphatic residue or a 3 to 6 membered heterocycloaliphatic residue, in each case unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$, C(=O)—OH and $CF_3$.

Preferably, $R^1$ represents a $C_{1-4}$ aliphatic residue, unsubstituted or mono- or polysubstituted with one or more substituents each selected independently of one another from the group consisting of F, Cl, Br, I, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, or represents a $C_{3-6}$ cycloaliphatic residue or a 3 to 6 membered heterocycloaliphatic residue, in each case unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$ and $CF_3$.

More preferably $R^1$ represents a $C_{1-4}$ aliphatic residue, unsubstituted or mono- or polysubstituted with one or more substituents each selected independently of one another from the group consisting of F, Cl, Br, I, and OH, or represents a $C_{3-6}$ cycloaliphatic residue or a 3 to 6 membered heterocycloaliphatic residue, in each case unsubstituted or mono- or polysubstituted with one or more substituents selected independently of one another from the group consisting of F, Cl, Br, I, and OH.

Even more preferably $R^1$ represents a $C_{1-4}$ aliphatic residue, unsubstituted or mono- or polysubstituted with one or more substituents each selected independently of one another from the group consisting of F, Cl, Br, I, or represents a $C_{3-6}$ cycloaliphatic residue or a 3 to 6 membered heterocycloaliphatic residue, in each case unsubstituted.

Still more preferably $R^1$ is selected from the group consisting of $CF_3$, methyl, ethyl, n-propyl, isopropyl, n-butyl, sec.-butyl, and tert.-butyl, or is selected from the group consisting of cyclopropyl, cyclobutyl, cyclopentyl, and cyclohexyl.

Particularly preferably, $R^1$ is selected from the group consisting of tert-Butyl, $CF_3$, cyclopropyl, cyclobutyl, cyclopentyl, and cyclohexyl, preferably from the group consisting of tert-Butyl, $CF_3$ and cyclopropyl, more preferably from the group consisting of tert-Butyl and $CF_3$.

In yet another preferred embodiment of the compound of general formula (I) according to the present invention $R^2$ represents a $C_{1-10}$ aliphatic residue, a O—$C_{1-10}$ aliphatic residue, a S—$C_{1-10}$ aliphatic residue, a NH—$C_{1-10}$ aliphatic residue, a N($C_{1-10}$ aliphatic residue)$_2$, wherein in each case independently of one another the $C_{1-10}$ aliphatic residue can be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH;

wherein each of the aforementioned residues can in each case be optionally bridged via a $C_{1-8}$ aliphatic group, which in turn may be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, and $SCF_3$, or represents a $C_{3-10}$ cycloaliphatic residue, a O—$C_{3-10}$ cycloaliphatic residue, a O—($C_{1-8}$ aliphatic group)-$C_{3-10}$ cycloaliphatic residue, a S—$C_{3-10}$ cycloaliphatic residue, a S—($C_{1-8}$ aliphatic group)-$C_{3-10}$ cycloaliphatic residue, a NH—$C_{3-10}$ cycloaliphatic residue, a NH—($C_{1-8}$ aliphatic group)-$C_{3-10}$ cycloaliphatic residue, a N($C_{1-10}$ aliphatic residue)($C_{3-10}$ cycloaliphatic residue), a 3 to 10 membered heterocycloaliphatic residue, O-(3 to 10 membered heterocycloaliphatic residue), O—($C_{1-8}$ aliphatic group)-(3 to 10 membered heterocycloaliphatic residue), S-(3 to 10 membered heterocycloaliphatic residue), S—($C_{1-8}$ aliphatic group)-(3 to 10 membered heterocycloaliphatic residue), NH-(3 to 10 membered heterocycloaliphatic residue), NH—($C_{1-8}$ aliphatic group)-(3 to 10 membered heterocycloaliphatic residue), N($C_{1-10}$ aliphatic residue)(3 to 10 membered heterocycloaliphatic residue), wherein in each case independently of one another the $C_{1-10}$ aliphatic residue, the $C_{1-8}$ aliphatic group, the $C_{3-10}$ cycloaliphatic residue and the 3 to 10 membered heterocycloaliphatic residue, respectively, can be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $C_{1-4}$ alkyl, $CF_3$, SH, S—$C_{1-4}$ alkyl, $SCF_3$, $NH_2$, NH($C_{1-4}$ alkyl), N($C_{1-4}$ alkyl)$_2$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH, wherein each of the aforementioned residues can in each case be optionally bridged via a $C_{1-8}$ aliphatic group, which in turn may be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, and $SCF_3$, or represents aryl, O-aryl, a O—($C_{1-8}$ aliphatic group)-aryl, S-aryl, a S—($C_{1-8}$ aliphatic group)-aryl, a NH-aryl, a NH—($C_{1-8}$ aliphatic group)-aryl, a N($C_{1-10}$ aliphatic residue)(aryl), heteroaryl, O-heteroaryl, O—($C_{1-8}$ aliphatic group)-heteroaryl, S-(heteroaryl), S—($C_{1-8}$ aliphatic group)-(heteroaryl), NH-(heteroaryl), NH—($C_{1-8}$ aliphatic group)-(heteroaryl), N($C_{1-10}$ aliphatic residue)(heteroaryl), wherein in each case independently of one another the $C_{1-10}$ aliphatic residue, the $C_{1-5}$ aliphatic group, aryl and heteroaryl, respectively, can be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $C_{1-4}$ alkyl, $CF_3$, SH, S—$C_{1-4}$ alkyl, $SCF_3$, $NH_2$, $NH(C_{1-4}$ alkyl), $N(C_{1-4}$ alkyl$)_2$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$, wherein each of the aforementioned residues can in each case be optionally bridged via a $C_{1-8}$ aliphatic group, which in turn may be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, $NH(C_{1-4}$ alkyl), $N(C_{1-4}$ alkyl$)_2$, SH, S—$C_{1-4}$ alkyl, and $SCF_3$.

In a further preferred embodiment of the compound of general formula (I) according to the present invention $R^2$ represents substructure (T1) in which

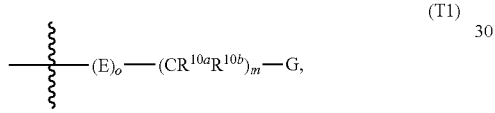

(T1)

E represents O, S, or $NR^{11}$,
  wherein $R^{11}$ represents H or a $C_{1-4}$ aliphatic residue, unsubstituted or mono- or polysubstituted with one or more substituents each selected independently of one another from the group consisting of F, Cl, Br, I, OH, O—$C_{1-4}$ alkyl, $OCF_3$, $NH_2$, NH—$C_{1-4}$ alkyl and $N(C_{1-4}$ alkyl$)_2$;
o represents 0 or 1;
$R^{10a}$ and $R^{10b}$ each independently of one another represent H; F; Cl; Br; I; or a $C_{1-4}$ aliphatic residue, unsubstituted or mono- or polysubstituted with one or more substituents each selected independently of one another from the group consisting of F, Cl, Br, I, OH, O—$C_{1-4}$ alkyl, $OCF_3$, $NH_2$, NH—$C_{1-4}$ alkyl and $N(C_{1-4}$ alkyl$)_2$;
m represents 0, 1, 2, 3 or 4, preferably 0, 1 or 2, more preferably 0 or 1;
G represents a $C_{1-4}$ aliphatic residue, unsubstituted or mono- or polysubstituted with one or more substituents each selected independently of one another from the group consisting of F, Cl, Br, I, $NO_2$, CN, OH, =O, O—$C_{1-4}$ alkyl, O—$C_{1-4}$ alkylene-O—$C_{1-4}$ alkyl, $OCF_3$, $CF_3$, $NH_2$, $NH(C_{1-4}$ alkyl), $N(C_{1-4}$ alkyl$)_2$, SH, S—$C_{1-4}$ alkyl, $SCF_3$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$;
  or represents a $C_{3-10}$ cycloaliphatic residue or a 3 to 10 membered heterocyclo-aliphatic residue, in each case unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $C_{1-4}$ alkyl, $CF_3$, SH, S—$C_{1-4}$ alkyl, $SCF_3$, $NH_2$, $NH(C_{1-4}$ alkyl), $N(C_{1-4}$ alkyl$)_2$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$;
  or represents an aryl or heteroaryl, unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, $CF_3$, SH, S—$C_{1-4}$ alkyl, $SCF_3$, $NH_2$, $NH(C_{1-4}$ alkyl), $N(C_{1-4}$ alkyl$)_2$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$.

In a particularly preferred embodiment of the compound according to the invention of general formula (I), the residue $R^2$ represents substructure (T1), wherein o denotes 0.

Preferably, the residue $R^2$ represents substructure (T1) in which

E represents O, S, or $NR^{11}$,
  wherein $R^{11}$ represents H or an unsubstituted $C_{1-4}$ aliphatic residue, preferably selected from the group consisting of methyl, ethyl, n-propyl, isopropyl, n-butyl, sec.-butyl, tert.-butyl;
o represents 0 or 1;
$R^{10a}$ and $R^{10b}$ each independently of one another represent H, F, Cl, Br, I or an unsubstituted $C_{1-4}$ aliphatic residue, preferably selected from the group consisting of methyl, ethyl, n-propyl, isopropyl, n-butyl, sec.-butyl, tert.-butyl;
m represents 0, 1 or 2, more preferably 0 or 1;
G represents a $C_{1-4}$ aliphatic residue, unsubstituted or mono- or polysubstituted with one or more substituents each selected independently of one another from the group consisting of F, Cl, Br, I, OH, O—$C_{1-4}$ alkyl, O—$C_{1-4}$ alkylene-O—$C_{1-4}$ alkyl, $OCF_3$, $CF_3$, $NH_2$, $NH(C_{1-4}$ alkyl), $N(C_{1-4}$ alkyl$)_2$, SH, S—$C_{1-4}$ alkyl, and $SCF_3$;
  or represents a $C_{3-10}$ cycloaliphatic residue or a 3 to 10 membered heterocyclo-aliphatic residue, in each case unsubstituted or mono- or polysubstituted with one or more substituents each selected independently of one another from the group consisting of F, Cl, Br, I, OH, O—$C_{1-4}$ alkyl, $OCF_3$, $C_{1-4}$ alkyl, $CF_3$, SH, S—$C_{1-4}$ alkyl, $SCF_3$, $NH_2$, $NH(C_{1-4}$ alkyl), $N(C_{1-4}$ alkyl$)_2$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$;
  or represents an aryl or heteroaryl, unsubstituted or mono- or polysubstituted with one or more substituents each selected independently of one another from the group consisting of F, Cl, Br, I, $NO_2$, CN, OH, O—$C_{1-4}$ alkyl, $OCF_3$, $CF_3$, SH, S—$C_{1-4}$ alkyl, $C_{1-4}$ alkyl, $SCF_3$, $NH_2$, $NH(C_{1-4}$ alkyl), $N(C_{1-4}$ alkyl$)_2$, phenyl and pyridyl, wherein phenyl or pyridyl are respectively unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH.

More preferably, the residue
R$^2$ represents substructure (T1) in which
E represents O, S, or NR$^{11}$, preferably represents O or S, wherein R$^{11}$ represents H or is selected from the group consisting of methyl, ethyl, n-propyl, and isopropyl,
o represents 0 or 1;
R$^{10a}$ and R$^{10b}$ are independently of one another selected from the group consisting of H, methyl, ethyl, n-propyl, isopropyl, n-butyl, sec.-butyl, tert.-butyl;
m represents 0, 1 or 2, more preferably 0 or 1;
G represents methyl, ethyl, n-propyl, isopropyl, n-butyl, sec.-butyl, or tert.-butyl, in each case unsubstituted or mono- or polysubstituted with one or more substituents each selected independently of one another from the group consisting of F, Cl, Br, I, OH, O—C$_{1-4}$ alkyl, and O—C$_{1-4}$ alkylene-O—C$_{1-4}$ alkyl;
  or represents a C$_{3-6}$ cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of pyrrolidinyl, piperazinyl, 4-methylpiperazinyl, piperidinyl, morpholinyl, tetrahydropyrrolyl, tetrahydropyranyl, tetrahydroquinolinyl, tetrahydroisoquinolinyl, dihydroquinolinyl, dihydropyrrolyl, dihydropyridinyl, dihydroisoquinolinyl, tetrahydropyridinyl and thiomorpholinyl, in each case unsubstituted or mono- or polysubstituted with one or more substituents each selected independently of one another from the group consisting of F, Cl, Br, I, OH, O—C$_{1-4}$ alkyl, OCF$_3$, C$_{1-4}$ alkyl, CF$_3$, NH$_2$, NH(C$_{1-4}$ alkyl), N(C$_{1-4}$ alkyl)$_2$, and phenyl, wherein phenyl can be unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, CF$_3$, and SCF$_3$;
  or represents an aryl or heteroaryl, preferably phenyl or pyridyl, in each case unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, CF$_3$, SH, S—C$_{1-4}$ alkyl, SCF$_3$, NH$_2$, NH(C$_{1-4}$ alkyl), N(C$_{1-4}$ alkyl)$_2$, and phenyl wherein phenyl can be unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, CF$_3$, and SCF$_3$.

Even more preferably, the residue
R$^2$ represents substructure (T1) in which
E represents O, S, or NR$^{11}$, preferably represents O or S, wherein R$^{11}$ represents H or is selected from the group consisting of methyl and ethyl,
o represents 0 or 1;
R$^{10a}$ and R$^{10b}$ are independently of one another selected from the group consisting of H, methyl and ethyl,
m represents 0, 1 or 2, more preferably 0 or 1;
G represents methyl, ethyl, n-propyl, isopropyl, n-butyl, sec.-butyl, or tert.-butyl, in each case unsubstituted;
  or is selected from the group consisting of cyclopropyl, cyclobutyl, cyclopentyl and cyclohexyl, or is selected from the group consisting of pyrrolidinyl, piperazinyl, 4-methylpiperazinyl, piperidinyl, morpholinyl and thiomorpholinyl, in each case unsubstituted or mono- or polysubstituted with one or more substituents each selected independently of one another from the group consisting of F, Cl, Br, I, OH, C$_{1-4}$ alkyl, O—C$_{1-4}$ alkyl, OCF$_3$, CF$_3$, NH$_2$, NH(C$_{1-4}$ alkyl), N(C$_{1-4}$ alkyl)$_2$, and phenyl, wherein phenyl can be unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, and SCF$_3$;
  or represents an aryl or heteroaryl, preferably phenyl or pyridyl, in each case unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, SCF$_3$, NH$_2$, NH(C$_{1-4}$ alkyl), N(C$_{1-4}$ alkyl)$_2$, and phenyl wherein phenyl can be unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, and SCF$_3$.

Still more preferably, the residue
R$^2$ represents substructure (T1) in which
E represents O or S,
o represents 0 or 1;
R$^{10a}$ and R$^{10b}$ are independently of one another selected from the group consisting of H, methyl and ethyl, preferably each denote H;
m represents 0, 1 or 2, more preferably 0 or 1;
G represents methyl, ethyl, n-propyl, isopropyl, n-butyl, sec.-butyl, or tert.-butyl, in each case unsubstituted;
  or is selected from the group consisting of cyclopropyl, cyclobutyl, cyclopentyl and cyclohexyl, or is selected from the group consisting of pyrrolidinyl, piperazinyl, 4-methylpiperazinyl, and piperidinyl, in each case unsubstituted or mono- or polysubstituted with one or more substituents each selected independently of one another from the group consisting of F, Cl, Br, I, OH, C$_{1-4}$ alkyl, O—C$_{1-4}$ alkyl, NH$_2$, NH(C$_{1-4}$ alkyl), N(C$_{1-4}$ alkyl)$_2$, and phenyl, wherein phenyl can be unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, and SCF$_3$;
  or represents phenyl or pyridyl, in each case unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, SCF$_3$, NH$_2$, NH(C$_{1-4}$ alkyl) and N(C$_{1-4}$ alkyl)$_2$.

Most preferred,
R$^2$ represents phenyl, unsubstituted or mono- or polysubstituted with one or more substituents each selected independently of one another from the group consisting of F, Cl, Br, I, OH, O—CH$_3$, CH$_3$, CH(CH$_3$)$_2$, N(CH$_3$)$_2$, tert.-butyl and CF$_3$, preferably phenyl mono- or disubstituted with one or two substituents each selected independently of one another from the group consisting of F, Cl, Br, I, O—CH$_3$, CH$_3$, CH(CH$_3$)$_2$, N(CH$_3$)$_2$, tert.-butyl and CF$_3$, more preferably phenyl mono-substituted in meta position with one substituent selected from the group consisting of F, Cl, CH$_3$, OCH$_3$, CH(CH$_3$)$_2$ and N(CH$_3$)$_2$.

In a preferred embodiment of the compound of general formula (I) according to the present invention n represents 1, 2, 3 or 4, preferably 1, 2 or 3, particularly preferably 1 or 2, most particularly preferably 1.

In another preferred embodiment of the compound of general formula (I) according to the present invention Y represents O or S, preferably represents O.

In yet another preferred embodiment of the compound of general formula (I) according to the present invention $R^3$ represents H or a $C_{1-4}$ aliphatic residue, unsubstituted or mono- or polysubstituted with one or more substituents each selected independently of one another from the group consisting of F, Cl, Br, I, CN, OH, =O, O—$C_{1-4}$ alkyl, $OCF_3$, $CF_3$, $NH_2$, $NH(C_{1-4}$ alkyl), $N(C_{1-4}$ alkyl)$_2$, SH, S—$C_{1-4}$ alkyl and $SCF_3$.

Preferably, $R^3$ represents H or a $C_{1-4}$ aliphatic residue, unsubstituted or mono- or polysubstituted with one or more substituents each selected independently of one another from the group consisting of F, Cl, Br, I and OH.

More preferably, $R^3$ represents H or an unsubstituted $C_{1-4}$ aliphatic residue, preferably selected from the group consisting of methyl, ethyl, n-propyl, isopropyl, n-butyl, sec.-butyl, and tert.-butyl.

In particular, $R^3$ is selected from the group consisting of H, methyl and ethyl, preferably denotes H or methyl, more preferably represents H.

Preferred is also an embodiment of the compound of general formula (I) according to the present invention, wherein $R^{4a}$ represents H or a $C_{1-4}$ aliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$, or represents a $C_{3-6}$ cycloaliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$, or denotes an aryl, unsubstituted or mono- or polysubstituted with at least one substituent selected from the group consisting of F, Cl, Br, I, $NO_2$, CN, OH, O—$C_{1-4}$ alkyl, $OCF_3$, $C_{1-4}$ alkyl, C(=O)—OH, $CF_3$, $CF_2H$, $CFH_2$, $CF_2Cl$, $CFCl_2$, $NH_2$, $NH(C_{1-4}$ alkyl), $N(C_{1-4}$ alkyl)$_2$, SH, S—$C_{1-4}$ alkyl, $SCF_3$, $S(=O)_2OH$ and NH—$S(=O)_2$—$C_{1-4}$ alkyl, $R^{4b}$ represents H or a $C_{1-4}$ aliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3S$ (=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$ or $R^{4a}$ and $R^{4b}$ together with the carbon atom connecting them form a $C_{3-6}$ cycloaliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$.

Preferably, $R^{4a}$ represents H or a $C_{1-4}$ aliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$, or represents a $C_{3-6}$ cycloaliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$, or denotes an aryl, unsubstituted or mono- or polysubstituted with at least one substituent selected from the group consisting of F, Cl, Br, I, $NO_2$, CN, OH, O—$C_{1-4}$ alkyl, $OCF_3$, $C_{1-4}$ alkyl, C(=O)—OH, $CF_3$, $CF_2H$, $CFH_2$, $CF_2Cl$, $CFCl_2$, $NH_2$, $NH(C_{1-4}$ alkyl), $N(C_{1-4}$ alkyl)$_2$, SH, S—$C_{1-4}$ alkyl, $SCF_3$, $S(=O)_2OH$ and NH—$S(=O)_2$—$C_{1-4}$ alkyl, $R^{4b}$ represents H or a $C_{1-4}$ aliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$, or $R^{4a}$ and $R^{4b}$ together with the carbon atom connecting them form a $C_{3-6}$ cycloaliphatic residue, unsubstituted or mono- or polysubstituted with at least one substituent selected from the group consisting of F, Cl, Br, I, $NO_2$, CN, OH, =O, O—$C_{1-4}$ alkyl, $OCF_3$, C(=O)—OH, $C_{1-4}$ alkyl, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$.

More preferably, $R^{4a}$ represents H or a $C_{1-4}$ aliphatic residue, unsubstituted or mono- or polysubstituted with at least one substituent selected from the group consisting of F, Cl, Br, I, OH, =O, O—$C_{1-4}$ alkyl, $OCF_3$, $CF_3$, and $SCF_3$, or represents a $C_{3-6}$ cycloaliphatic residue, unsubstituted or mono- or polysubstituted with at least one substituent selected from the group consisting of F, Cl, Br, I, OH, =O, O—$C_{1-4}$ alkyl, $OCF_3$, $C_{1-4}$ alkyl, $CF_3$, and $SCF_3$, or denotes an aryl, preferably a phenyl, unsubstituted or mono- or polysubstituted with at least one substituent selected from the group consisting of F, Cl, Br, I, $NO_2$, CN, OH, O—$C_{1-4}$ alkyl, $OCF_3$, $C_{1-4}$ alkyl, C(=O)—OH, $CF_3$, $CF_2H$, $CFH_2$, $CF_2Cl$, $CFCl_2$, $NH_2$, NH($C_{1-4}$ alkyl), N($C_{1-4}$ alkyl)$_2$, SH, S—$C_{1-4}$ alkyl, $SCF_3$, S(=O)$_2$OH and NH—S(=O)$_2$—$C_{1-4}$ alkyl, $R^{4b}$ represents H or a $C_{1-4}$ aliphatic residue, unsubstituted or mono- or polysubstituted with at least one substituent selected from the group consisting of F, Cl, Br, I, OH, =O, O—$C_{1-4}$ alkyl, $OCF_3$, $CF_3$, and $SCF_3$, or $R^{4a}$ and $R^{4b}$ together with the carbon atom connecting them form a $C_{3-6}$ cycloaliphatic residue, unsubstituted or mono- or polysubstituted with at least one substituent selected from the group consisting of F, Cl, Br, I, OH, =O, O—$C_{1-4}$ alkyl, $OCF_3$, $C_{1-4}$ alkyl, $CF_3$, and $SCF_3$.

Even more preferably, $R^{4a}$ represents H or an unsubstituted $C_{1-4}$ aliphatic residue, preferably denotes H or is selected from the group consisting of methyl, ethyl, n-propyl, isopropyl, n-butyl, sec.-butyl, and tert.-butyl, or represents an unsubstituted $C_{3-6}$ cycloaliphatic residue, preferably selected from the group consisting of cyclopropyl, cyclobutyl, cyclopentyl and cyclohexyl, or denotes a phenyl, unsubstituted or mono- or polysubstituted with at least one substituent selected from the group consisting of F, Cl, Br, I, $NO_2$, CN, OH, O—$C_{1-4}$ alkyl, $OCF_3$, $C_{1-4}$ alkyl, C(=O)—OH, $CF_3$, $CF_2H$, $CFH_2$, $CF_2Cl$, $CFCl_2$, $NH_2$, NH($C_{1-4}$ alkyl), N($C_{1-4}$ alkyl)$_2$, SH, S—$C_{1-4}$ alkyl, $SCF_3$, S(=O)$_2$OH and NH—S(=O)$_2$—$C_{1-4}$ alkyl, $R^{4b}$ represents H or a $C_{1-4}$ aliphatic residue, unsubstituted or mono- or polysubstituted with at least one substituent selected from the group consisting of F, Cl, Br, I, OH, =O, O—$C_{1-4}$ alkyl, $OCF_3$, $CF_3$, and $SCF_3$, or $R^{4a}$ and $R^{4b}$ together with the carbon atom connecting them form a $C_{3-6}$ cycloaliphatic residue, preferably selected from the group consisting of cyclopropyl, cyclobutyl, cyclopentyl and cyclohexyl, unsubstituted or mono- or polysubstituted with at least one substituent selected from the group consisting of F, Cl, Br, I, OH, =O, O—$C_{1-4}$ alkyl, $OCF_3$, $C_{1-4}$ alkyl, $CF_3$, and $SCF_3$.

Still more preferably, $R^{4a}$ represents H; methyl, ethyl, cyclopropyl, cyclobutyl, cyclopentyl, cyclohexyl, or phenyl, wherein phenyl is unsubstituted or substituted with 1, 2, 3, 4 or 5 substituents independently selected from the group consisting of F, Cl, Br, I, $NO_2$, CN, $CF_3$, $CF_2H$, $CFH_2$, $CF_2Cl$, $CFCl_2$, OH, $NH_2$, NH($C_{1-4}$ alkyl) and N($C_{1-4}$ alkyl)($C_{1-4}$ alkyl), $C_{1-4}$ alkyl, and O—$C_{1-4}$-alkyl;

$R^{4b}$ represents H, methyl, or ethyl, or $R^{4a}$ and $R^{4b}$ together with the carbon atom connecting them form a cyclopropyl, cyclobutyl, cyclopentyl, or cyclohexyl ring.

Particularly preferred is a compound of general formula (I) according to the present invention, wherein $R^{4a}$ represents H, methyl, ethyl, cyclopropyl, cyclobutyl, cyclopentyl, cyclohexyl, or phenyl, wherein phenyl is unsubstituted or substituted with 1, 2 or 3 substituents independently selected from the group consisting of F, Cl, Br, $CF_3$, methyl and methoxy;

$R^{4b}$ represents H, methyl, or ethyl, or $R^{4a}$ and $R^{4b}$ together with the carbon atom connecting them form cyclopropyl, cyclobutyl, cyclopentyl, or cyclohexyl ring.

Even more particularly preferred is a compound of general formula (I) according to the present invention, wherein $R^{4a}$ represents H, methyl, or ethyl, $R^{4b}$ represents H, methyl, or ethyl, preferably H or methyl, more preferably H, or $R^{4a}$ and $R^{4b}$ together with the carbon atom connecting them form cyclopropyl, cyclobutyl, cyclopentyl, or cyclohexyl ring.

Most preferred is a compound of general formula (I) according to the present invention, wherein $R^{4a}$ represents H, methyl, or ethyl, more preferably H or methyl $R^{4b}$ represents H, methyl, or ethyl, preferably H or methyl, In yet another preferred embodiment of the compound of general formula (I) according to the present invention, Z represents N and $R^{4a}$ represents H; or Z represents $CR^{4b}$ and $R^{4a}$ and $R^{4b}$ each represent H; or Z represents $CR^{4b}$ and $R^{4a}$ represents methyl and $R^{4b}$ represents H.

In a preferred embodiment of the compound of general formula (I) according to the present invention $T^1$ represents N or C—$R^5$, $U^1$ represents N or C—$R^6$, V represents N or C—$R^7$, $U^2$ represents C—$R^8$, $T^2$ represents C—$R^9$, with the proviso that 0, 1, or 2, preferably 0 or 1, of variables $T^1$, $U^1$ and V, represent a nitrogen atom simultaneously.

In another preferred embodiment of the compound according to the invention of general formula (I), the substructure (T2)

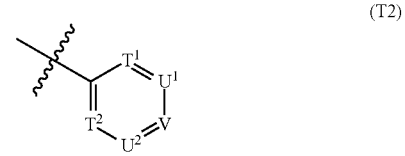

represents one or more of the substructures (T2-a), (T2-b), (T2-c), (T2-d), (T2-e), (T2-f), (T2-g), (T2-h) and (T2-i)

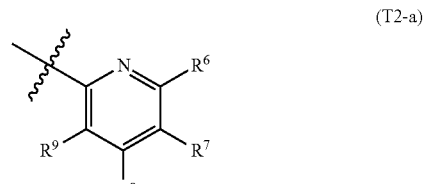

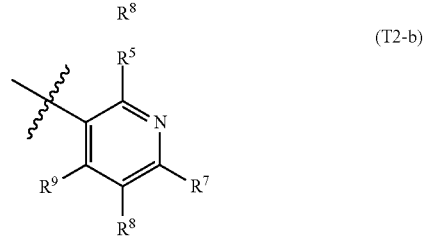

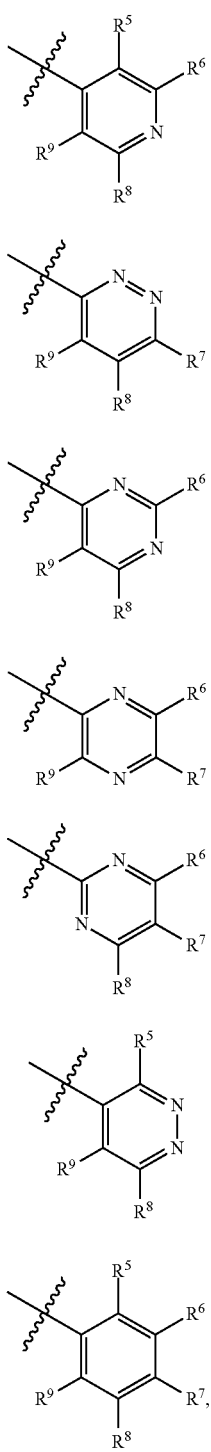

(T2-c)
(T2-d)
(T2-e)
(T2-f)
(T2-g)
(T2-h)
(T2-i)

in which $R^5$, $R^6$, $R^7$, $R^8$ and $R^9$ in each case independently of one another have one of the above defined meanings or have the meaning as described herein in connection with the compounds according to the invention and preferred embodiments thereof.

Particularly preferred substructures of (T2) are (T2-a), (T2-b), (T2-c) and (T2-i).

In a further preferred embodiment of the compound according to the invention of general formula (I),
$R^5$ and $R^6$ together or
$R^6$ and $R^7$ together or
$R^7$ and $R^8$ together or
$R^8$ and $R^9$ together,
in pairs in each case independently of one another, together with the carbon atoms connecting them form a $C_{3-10}$-cycloaliphatic residue, preferably a $C_{3-6}$-cycloaliphatic residue, or a 3 to 10 membered heterocycloaliphatic residue, preferably a 3 to 6 membered heterocycloaliphatic residue, in each case unsubstituted or mono- or polysubstituted with one or more substituents selected independently of one another from the group consisting of F, Cl, Br, I, $C_{1-4}$ alkyl, $C_{1-4}$ alkylene-OH, $CF_3$, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, =O, $OCF_3$, OH, SH, S—$C_{1-4}$ alkyl, $SCF_3$, $SO_2$—$C_{1-4}$ alkyl, $NH_2$, =NH, =N(OH), NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$,
or in pairs in each case independently of one another, together with the carbon atoms connecting them form an aryl, preferably a phenyl, or heteroaryl, in each case unsubstituted or mono- or polysubstituted with one or more substituents selected independently of one another from the group consisting of F, Cl, Br, I, $C_{1-4}$ alkyl, $C_{1-4}$ alkylene-OH, $CF_3$, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, $OCF_3$, OH, SH, S—$C_{1-4}$ alkyl, $SCF_3$, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$,
and the respective remaining substituents of $R^5$, $R^6$, $R^7$, $R^8$, and $R^9$ each independently of one another represent H, F, Cl, Br, I, CN, $CF_3$, $CF_2H$, $CFH_2$, $CF_2Cl$, $CFCl_2$, $NO_2$, OH, $OCF_3$, $OCF_2H$, $OCFH_2$, $OCF_2Cl$, $OCFCl_2$, O—$C_{1-4}$ alkyl, O—$C_{1-4}$ alkylene-OH, O—$C_{1-4}$ alkylene-O—$C_{1-4}$ alkyl, C(=O)—H, C(=O)—OH, C(=O)—$NH_2$, $C_{1-4}$ alkyl, $C_{1-4}$ alkyl-OH, C(=O)—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, SH, $SCF_3$, $SCF_2H$, $SCFH_2$, $SCF_2Cl$, $SCFCl_2$, S(=O)$_2$—OH, S(=O)$_2$—$NH_2$, S—$C_{1-4}$ alkyl, $SO_2$—$C_{1-4}$ alkyl,
or a $C_{3-6}$-cycloaliphatic residue or a 3 to 6 membered heterocycloaliphatic residue, in each case unsubstituted or mono- or polysubstituted with one or more substituents selected independently of one another from the group consisting of F, Cl, Br, I, $C_{1-4}$ alkyl, $C_{1-4}$ alkyl-OH, $CF_3$, C(=O)—$C_{1-4}$ alkyl, O—$C_{1-4}$ alkyl, O—$C_{1-4}$ alkylene-OH, alkylene-O—$C_{1-4}$ alkyl, =O, $OCF_3$, OH, SH, S—$C_{1-4}$ alkyl, $SCF_3$, $SO_2$—$C_{1-4}$ alkyl, $NH_2$, =NH, =N(OH), NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$,
wherein the $C_{3-5}$-cycloaliphatic residue or the 3 to 6 membered heterocycloaliphatic residue can in each case be optionally bridged via a $C_{1-8}$ aliphatic group, which in turn may be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, and $SCF_3$, or an aryl or heteroaryl, in each case unsubstituted or mono- or polysubstituted with one or more substituents selected independently of one another from the group consisting of F, Cl, Br, I, $C_{1-4}$ alkyl, $C_{1-4}$ alkyl-OH, $CF_3$, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, $OCF_3$, OH, SH, S—$C_{1-4}$ alkyl, $SCF_3$, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, wherein aryl or heteroaryl can in each case be optionally bridged via a $C_{1-8}$ aliphatic group, which in turn may be unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, and $SCF_3$.

Preferably, $R^5$ and $R^6$ together or
$R^6$ and $R^7$ together or
$R^7$ and $R^8$ together or
$R^8$ and $R^9$ together, in pairs in each case independently of one another, together with the carbon atoms connecting them form a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of pyrrolidinyl, piperazinyl, 4-methylpiperazinyl, piperidinyl, pyrazolidinyl, pyranyl, tetrahydropyrrolyl, tetrahydropyranyl, morpholinyl, imidazolidinyl, dihydrofuranyl, dioxanyl and dioxolanyl, in each case unsubstituted or mono- or polysubstituted with one or more substituents selected independently of one another from the group consisting of F, Cl, Br, I, $C_{1-4}$ alkyl, $C_{1-4}$ alkyl-OH, $CF_3$, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, SH, S—$C_{1-4}$ alkyl, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, or in pairs in each case independently of one another, together with the carbon atoms connecting them form an aryl, preferably a phenyl, or heteroaryl, preferably selected from the group consisting of pyrazinyl, pyrimidinyl, pyridyl, oxazolyl, thiazolyl, pyrazolyl, pyrrolyl, imidazolyl, isoxazoyl, isothiazolyl, oxadiazolyl, pyrrolyl, pyridazinyl, purinyl, and thiadiazolyl, in each case unsubstituted or mono- or polysubstituted with one or more substituents selected independently of one another from the group consisting of F, Cl, Br, I, $C_{1-4}$ alkyl, $C_{1-4}$ alkyl-OH, $CF_3$, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, $OCF_3$, OH, SH, S—$C_{1-4}$ alkyl, $SCF_3$, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, and the respective remaining substituents of $R^5$, $R^6$, $R^7$, $R^8$, and $R^9$ each independently of one another represent H, F, Cl, Br, I, CN, $CF_3$, $CF_2$H, $CFH_2$, $CF_2$Cl, $CFCl_2$, $NO_2$, OH, $OCF_3$, $OCF_2$H, $OCFH_2$, $OCF_2$Cl, $OCFCl_2$, O—$C_{1-4}$ alkyl, O—$C_{1-4}$ alkyl-OH, O—$C_{1-4}$ alkyl-O—$C_{1-4}$ alkyl, C(=O)—H, C(=O)—OH, C(=O)—$NH_2$, $C_{1-4}$ alkyl, $C_{1-4}$ alkyl-OH, C(=O)—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, SH, $SCF_3$, $SCF_2$H, $SCFH_2$, $SCF_2$Cl, $SCFCl_2$, S(=O)$_2$—OH, S(=O)$_2$—$NH_2$, S—$C_{1-4}$ alkyl, $SO_2$—$C_{1-4}$ alkyl, or a $C_{3-6}$-cycloaliphatic residue or a 3 to 6 membered heterocycloaliphatic residue, in each case unsubstituted or mono- or polysubstituted with one or more substituents selected independently of one another from the group consisting of F, Cl, Br, I, $C_{1-4}$ alkyl, $C_{1-4}$ alkyl-OH, O—$C_{1-4}$ alkyl, O—$C_{1-4}$ alkylene-OH, OH, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, and NH—C(=O)—$C_{1-4}$ alkyl, wherein the $C_{3-6}$-cycloaliphatic residue or the 3 to 6 membered heterocycloaliphatic residue can in each case be optionally bridged via a $C_{1-8}$ aliphatic group, which in turn may be unsubstituted or mono- or polysubstituted with one or more substituents each selected independently of one another from the group consisting of F, Cl, Br, I, OH, and O—$C_{1-4}$ alkyl, or an aryl or heteroaryl, in each case unsubstituted or mono- or polysubstituted with one or more substituents selected independently of one another from the group consisting of F, Cl, Br, I, $C_{1-4}$ alkyl, $C_{1-4}$ alkyl-OH, $CF_3$, O—$C_{1-4}$ alkyl, O—$C_{1-4}$ alkylene-OH, $OCF_3$, OH, $SO_2$—$C_{1-4}$ alkyl, $NH_2$, NH—$C_{1-4}$ alkyl, N($C_{1-4}$ alkyl)$_2$, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, wherein aryl or heteroaryl can in each case be optionally bridged via a $C_{1-8}$ aliphatic group, which in turn may be unsubstituted or mono- or polysubstituted with one or more substituents each selected independently of one another from the group consisting of F, Cl, Br, I, OH, and O—$C_{1-4}$ alkyl.

More preferably, $R^5$ and $R^6$ together or
$R^6$ and $R^7$ together or
$R^7$ and $R^8$ together or
$R^8$ and $R^9$ together, in pairs in each case independently of one another, together with the carbon atoms connecting them form a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of pyrrolidinyl, piperazinyl, 4-methylpiperazinyl, piperidinyl, pyrazolidinyl, pyranyl, tetrahydropyrrolyl, tetrahydropyranyl, morpholinyl, imidazolidinyl, dihydrofuranyl, dioxanyl and dioxolanyl, in each case unsubstituted or mono- or polysubstituted with one or more substituents selected independently of one another from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl and O—$C_{1-4}$ alkyl, or in pairs in each case independently of one another, together with the carbon atoms connecting them form an aryl, preferably a phenyl, or a 5-6 membered heteroaryl, preferably selected from the group consisting of pyrazinyl, pyrimidinyl, pyridyl, oxazolyl, thiazolyl, pyrazolyl, pyrrolyl, imidazolyl, isoxazoyl, isothiazolyl, oxadiazolyl, pyrrolyl, pyridazinyl, purinyl, and thiadiazolyl, in each case unsubstituted or mono- or polysubstituted with one or more substituents selected independently of one another from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, and phenyl, unsubstituted or mono- or polysubstituted with one or more substituents each selected independently of one another from the group consisting of F, Cl, Br, I, $C_{1-4}$ alkyl, and O—$C_{1-4}$ alkyl, and the respective remaining substituents of $R^5$, $R^6$, $R^7$, $R^8$, and $R^9$ each independently of one another represent H, F, Cl, Br, I, $CF_3$, $CF_2H$, $CFH_2$, $CF_2Cl$, $CFCl_2$, $NO_2$, OH, $OCF_3$, $OCF_2H$, $OCFH_2$, $OCF_2Cl$, $OCFCl_2$, O—$C_{1-4}$ alkyl, O—$C_{1-4}$ alkyl-OH, $C_{1-4}$ alkyl, $C_{1-4}$ alkylene-OH, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, SH, $SCF_3$, $SCF_2H$, $SCFH_2$, $SCF_2Cl$, $SCFCl_2$, S—$C_{1-4}$ alkyl, $SO_2$—$C_{1-4}$ alkyl, or a $C_{3-6}$-cycloaliphatic residue, preferably selected from the group consisting of cyclopropyl, cyclobutyl, cyclopentyl and cyclohexyl, or a 3 to 6, preferably a 5 to 6, membered heterocycloaliphatic residue, in each case unsubstituted
 wherein the $C_{3-6}$-cycloaliphatic residue or the 3 to 6 membered heterocycloaliphatic residue can in each case be optionally bridged via an unsubstituted $C_{1-8}$ aliphatic group, or a phenyl or pyridyl, in each case unsubstituted or mono- or polysubstituted with one or more substituents selected independently of one another from the group consisting of F, Cl, Br, I, $C_{1-4}$ alkyl, $C_{1-4}$ alkyl-OH, $CF_3$, O—$C_{1-4}$ alkyl, O—$C_{1-4}$ alkylene-OH, $OCF_3$, OH, $SO_2$—$C_{1-4}$ alkyl, $NH_2$, NH—$C_{1-4}$ alkyl, N($C_{1-4}$ alkyl)$_2$, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, wherein phenyl or pyridyl can in each case be optionally bridged via an unsubstituted $C_{1-8}$ aliphatic group.

Even more preferably, $R^5$ and $R^6$ together or
$R^6$ and $R^7$ together or
$R^7$ and $R^8$ together or
$R^8$ and $R^9$ together, in pairs in each case independently of one another, together with the carbon atoms connecting them form a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of pyrrolidinyl, piperazinyl, 4-methylpiperazinyl, piperidinyl, pyrazolidinyl, pyranyl, tetrahydropyrrolyl, tetrahydropyranyl, morpholinyl, imidazolidinyl, dihydrofuranyl, dioxanyl and dioxolanyl, in each case unsubstituted or mono- or polysubstituted with one or more substituents selected independently of one another from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl and NH—C(=O)—$C_{1-4}$ alkyl, or in pairs in each case independently of one another, together with the carbon atoms connecting them form an aryl, preferably a phenyl, or a 5-6 membered heteroaryl, preferably selected from the group consisting of pyrazinyl, pyrimidinyl, pyridyl, oxazolyl, thiazolyl, pyrazolyl, pyrrolyl, imidazolyl, isoxazoyl, isothiazolyl, oxadiazolyl, pyrrolyl, pyridazinyl, purinyl, and thiadiazolyl, in each case unsubstituted or mono- or polysubstituted with one or more substituents selected independently of one another from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, N($C_{1-4}$ alkyl)$_2$, NH—$SO_2$—$C_{1-4}$ alkyl and NH—C(=O)—$C_{1-4}$ alkyl, the respective remaining substituents of $R^5$, $R^6$, $R^7$, $R^8$, and $R^9$ each independently of one another represent H, F, Cl, Br, I, $CF_3$, OH, $OCF_3$, O—$C_{1-4}$ alkyl, O—$C_{1-4}$ alkylene-OH, $C_{1-4}$ alkyl, $C_{1-4}$ alkyl-OH, $NH_2$, NH—$C_{1-4}$ alkyl, N($C_{1-4}$ alkyl)$_2$, NH—$SO_2$—$C_{1-4}$ alkyl, NH—C(=O)—$C_{1-4}$ alkyl, $SCF_3$, $SO_2$—$C_{1-4}$ alkyl, or an unsubstituted $C_{3-6}$-cycloaliphatic residue selected from the group consisting of cyclopropyl, cyclobutyl, cyclopentyl and cyclohexyl, or an unsubstituted phenyl or pyridyl.

A particularly preferred embodiment of the present invention is the compound according to the general formula (I), wherein X represents N or CH, $R^1$ is selected from the group consisting of tert-Butyl, $CF_3$ and cyclopropyl, more preferably from the group consisting of tert-Butyl and $CF_3$, $R^2$ represents substructure (T1)

in which

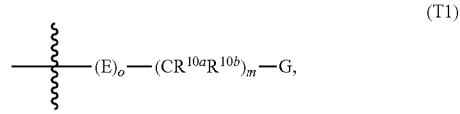

E represents O or S, o represents 0 or 1;

$R^{10a}$ and $R^{10b}$ are independently of one another selected from the group consisting of H, methyl and ethyl, preferably each denote H;

m represents 0, 1 or 2, more preferably 0 or 1;

G represents methyl, ethyl, n-propyl, isopropyl, n-butyl, sec.-butyl, or tert.-butyl, in each case unsubstituted;

or is selected from the group consisting of cyclopropyl, cyclobutyl, cyclopentyl and cyclohexyl, or is selected from the group consisting of pyrrolidinyl, piperazinyl, 4-methylpiperazinyl, and piperidinyl, in each case unsubstituted or mono- or polysubstituted with one or more substituents each selected independently of one another from the group consisting of F, Cl, Br, I, OH, $C_{1-4}$ alkyl, O—$C_{1-4}$ alkyl, $NH_2$, NH($C_{1-4}$ alkyl), N($C_{1-4}$ alkyl)$_2$, and phenyl, wherein phenyl can be unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, and $SCF_3$;

or represents phenyl or pyridyl, in each case unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $SCF_3$, $NH_2$, $NH(C_{1-4}$ alkyl) and $N(C_{1-4}$ alkyl$)_2$, n represents 1, 2 or 3, preferably 1 or 2, more preferably 1, $R^3$ is selected from the group consisting of H, methyl and ethyl, preferably denotes H or methyl, more preferably represents H.

$R^{4a}$ represents H, methyl, or ethyl,

Y denotes O,

Z represents N or $CR^{4b}$, preferably represents N when $R^{4a}$ denotes H or preferably represents $CR^{4b}$ when $R^{4a}$ and $R^{4b}$ each represent H or preferably represents $CR^{4b}$ when $R^{4a}$ represents methyl and $R^{4b}$ represents H, $R^{4b}$ represents H, methyl, or ethyl, preferably H or methyl, more preferably H, or $R^{4a}$ and $R^{4b}$ together with the carbon atom connecting them form a cyclopropyl, cyclobutyl, cyclopentyl, or cyclohexyl ring, $T^1$ represents N or C—$R^5$, $U^1$ represents N or C—$R^6$, V represents N or C—$R^7$, $U^2$ represents C—$R^8$, $T^2$ represents C—$R^9$, with the proviso that 0, 1, or 2, preferably 0 or 1, of variables $T^1$, $U^1$ and V, represent a nitrogen atom simultaneously, $R^5$ and $R^6$ together or $R^6$ and $R^7$ together or $R^7$ and $R^8$ together or $R^8$ and $R^9$ together, in pairs in each case independently of one another, together with the carbon atoms connecting them form a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of pyrrolidinyl, piperazinyl, 4-methylpiperazinyl, piperidinyl, pyrazolidinyl, pyranyl, tetrahydropyrrolyl, tetrahydropyranyl, morpholinyl, imidazolidinyl, dihydrofuranyl, dioxanyl and dioxolanyl, in each case unsubstituted or mono- or polysubstituted with one or more substituents selected independently of one another from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, $N(C_{1-4}$ alkyl$)_2$, NH—$SO_2$—$C_{1-4}$ alkyl and NH—C(=O)—$C_{1-4}$ alkyl, or in pairs in each case independently of one another, together with the carbon atoms connecting them form an aryl, preferably a phenyl, or a 5-6 membered heteroaryl, preferably selected from the group consisting of pyrazinyl, pyrimidinyl, pyridyl, oxazolyl, thiazolyl, pyrazolyl, pyrrolyl, imidazolyl, isoxazoyl, isothiazolyl, oxadiazolyl, pyrrolyl, pyridazinyl, purinyl, and thiadiazolyl, in each case unsubstituted or mono- or polysubstituted with one or more substituents selected independently of one another from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, $N(C_{1-4}$ alkyl$)_2$, NH—$SO_2$—$C_{1-4}$ alkyl and NH—C(=O)—$C_{1-4}$ alkyl, and the respective remaining substituents of $R^5$, $R^6$, $R^7$, $R^8$, and $R^9$ each independently of one another represent H, F, Cl, Br, I, $CF_3$, OH, $OCF_3$, O—$C_{1-4}$ alkyl, O—$C_{1-4}$ alkyl-OH, $C_{1-4}$ alkyl, $C_{1-4}$ alkyl-OH, $NH_2$, NH—$C_{1-4}$ alkyl, $N(C_{1-4}$ alkyl$)_2$, NH—$SO_2$—$C_{1-4}$ alkyl, NH—C(=O)—$C_{1-4}$ alkyl, $SCF_3$, $SO_2$—$C_{1-4}$ alkyl, or an unsubstituted $C_{3-6}$-cycloaliphatic residue selected from the group consisting of cyclopropyl, cyclobutyl, cyclopentyl and cyclohexyl, or an unsubstituted phenyl or pyridyl.

Particularly preferred are compounds according to the invention from the group 1. 1-(6,7-Dihydro-5H-cyclopenta[b]pyridin-3-yl)-3-((2-(4-methylpiperidin-1-yl)-6-(trifluoromethyl)pyridin-3-yl)methyl)urea;
2. 1-((2-(4-Methylpiperidin-1-yl)-6-(trifluoromethyl)pyridin-3-yl)methyl)-3-(5,6,7,8-tetrahydroisoquinolin-4-yl)urea;
3. 1-(2,3-Dihydro-[1,4]dioxino[2,3-b]pyridin-6-yl)-3-((2-(4-methylpiperidin-1-yl)-6-(trifluoromethyl)pyridin-3-yl)methyl)urea;
4. 1-(2,3-Dihydro-1H-pyrrolo[2,3-b]pyridin-5-yl)-3-((2-(4-methylpiperidin-1-yl)-6-(trifluoromethyl)pyridin-3-yl)methyl)urea;
5. 1-((2-(4-methylpiperidin-1-yl)-6-(trifluoromethyl)pyridin-3-yl)methyl)-3-(1H-pyrazolo[3,4-b]pyridin-5-yl)urea;
6. 1-((2-(3-Fluorophenyl)-6-(trifluoromethyl)pyridin-3-yl)methyl)-3-(oxazolo[5,4-b]pyridin-6-yl)urea;
7. 1-((2-(4-Methylpiperidin-1-yl)-6-(trifluoromethyl)pyridin-3-yl)methyl)-3-(2-methylthiazolo[5,4-b]pyridin-6-yl)urea;
8. N-((2-(4-Methylpiperidin-1-yl)-6-(trifluoromethyl)pyridin-3-yl)methyl)-2-(1H-pyrazolo[3,4-b]pyridin-4-yl)propanamide;
9. 1-((2-(4-Methylpiperidin-1-yl)-6-(trifluoromethyl)pyridin-3-yl)methyl)-3-(1H-pyrazolo[3,4-b]pyridin-4-yl)urea;
10. 1-((2-(4-Methylpiperidin-1-yl)-6-(trifluoromethyl)pyridin-3-yl)methyl)-3-(1H-pyrazolo[4,3-c]pyridin-4-yl)urea;
11. 1-((2-(Cyclohexylthio)-6-(trifluoromethyl)pyridin-3-yl)methyl)-3-(quinolin-2-yl)urea;
12. 1-((2-(4-Methylpiperidin-1-yl)-6-(trifluoromethyl)pyridin-3-yl)methyl)-3-(quinolin-3-yl)urea;
13. N-((2-(4-Methylpiperidin-1-yl)-6-(trifluoromethyl)pyridin-3-yl)methyl)-2-(quinolin-3-yl)acetamide;
14. N-((2-(4-Methylpiperidin-1-yl)-6-(trifluoromethyl)pyridin-3-yl)methyl)-2-(quinolin-3-yl)propanamide;
15. N-((2-(Cyclohexylthio)-6-(trifluoromethyl)pyridin-3-yl)methyl)-2-(quinolin-3-yl)propanamide;
16. N-(2-(4-Methylpiperidin-1-yl)-4-(trifluoromethyl)benzyl)-2-(quinolin-3-yl)propanamide;
17. 1-((2-(4-Methylpiperidin-1-yl)-6-(trifluoromethyl)pyridin-3-yl)methyl)-3-(quinolin-4-yl)urea;
18. 1-(Isoquinolin-4-yl)-3-((2-(4-methylpiperidin-1-yl)-6-(trifluoromethyl)pyridin-3-yl)methyl)urea;
19. 1-((2-(Cyclohexylthio)-6-(trifluoromethyl)pyridin-3-yl)methyl)-3-(isoquinolin-4-yl)urea;
20. 1-(Isoquinolin-1-yl)-3-((2-(4-methylpiperidin-1-yl)-6-(trifluoromethyl)pyridin-3-yl)methyl)urea;
21. 1-(Isoquinolin-3-yl)-3-((2-(4-methylpiperidin-1-yl)-6-(trifluoromethyl)pyridin-3-yl)methyl)urea;

22. 1-(1H-Indol-6-yl)-3-((2-(4-methylpiperidin-1-yl)-6-(trifluoromethyl)pyridin-3-yl)methyl)urea;
23. 1-(1H-Indol-5-yl)-3-((2-(4-methylpiperidin-1-yl)-6-(trifluoromethyl)pyridin-3-yl)methyl)urea;
24. 1-(2-Methyl-1H-indol-5-yl)-3-((2-(4-methylpiperidin-1-yl)-6-(trifluoromethyl)pyridin-3-yl)methyl)urea;
25. 1-((2-(4-Methylpiperidin-1-yl)-6-(trifluoromethyl)pyridin-3-yl)methyl)-3-O-(methylsulfonyl)-1H-indazol-5-yl)urea;
26. 1-(1-Methyl-1H-benzo[d]imidazol-6-yl)-3-((2-(4-methylpiperidin-1-yl)-6-(trifluoromethyl)pyridin-3-yl)methyl)urea;
27. 1-(1-Methyl-1H-indazol-6-yl)-3-((2-(4-methylpiperidin-1-yl)-6-(trifluoromethyl)pyridin-3-yl)methyl)urea;
28. 1-(7-Fluorobenzo[d]oxazol-5-yl)-3-((2-(4-methylpiperidin-1-yl)-6-(trifluoromethyl)pyridin-3-yl)methyl)urea;
29. 1-(Benzo[d]thiazol-5-yl)-3-((2-(4-methylpiperidin-1-yl)-6-(trifluoromethyl)pyridin-3-yl)methyl)urea;
30. 1-(2-Methylbenzo[d]thiazol-5-yl)-3-((2-(4-methylpiperidin-1-yl)-6-(trifluoromethyl)pyridin-3-yl)methyl)urea;
31. N-(5-(3-((2-(4-methylpiperidin-1-yl)-6-(trifluoromethyl)pyridin-3-yl)methyl)ureido)benzo[d]thiazol-2-yl)acetamide;
32. 1-(Benzo[d]thiazol-6-yl)-3-((2-(4-methylpiperidin-1-yl)-6-(trifluoromethyl)pyridin-3-yl)methyl)urea;
33. 1-(2-Methylbenzo[d]thiazol-6-yl)-3-((2-(4-methylpiperidin-1-yl)-6-(trifluoromethyl)pyridin-3-yl)methyl)urea;
34. 1-(2-Aminobenzo[d]thiazol-6-yl)-3-((2-(4-methylpiperidin-1-yl)-6-(trifluoromethyl)pyridin-3-yl)methyl)urea;
35. N-(6-(3-((2-(4-Methylpiperidin-1-yl)-6-(trifluoromethyl)pyridin-3-yl)methyl)ureido)benzo[d]thiazol-2-yl)acetamide;
36. 1-(1H-Indol-7-yl)-3-((2-(4-methylpiperidin-1-yl)-6-(trifluoromethyl)pyridin-3-yl)methyl)urea;
37. 1-(2,3-Dimethyl-1H-indol-7-yl)-3-((2-(4-methylpiperidin-1-yl)-6-(trifluoromethyl)pyridin-3-yl)methyl)urea;
38. 1-(1H-Indol-4-yl)-3-((2-(4-methylpiperidin-1-yl)-6-(trifluoromethyl)pyridin-3-yl)methyl)urea;
39. 1-((2-(4-(Dimethylamino)-4-phenylpiperidin-1-yl)-6-(trifluoromethyl)pyridin-3-yl)methyl)-3-(1H-indol-4-yl)urea;
40. 1-(1-Methyl-1H-indol-4-yl)-3-((2-(4-methylpiperidin-1-yl)-6-(trifluoromethyl)pyridin-3-yl)methyl)urea;
41. 1-(1-Acetyl-1H-indol-4-yl)-3-((2-(4-methylpiperidin-1-yl)-6-(trifluoromethyl)pyridin-3-yl)methyl)urea;
42. 1-((2-(4-Methylpiperidin-1-yl)-6-(trifluoromethyl)pyridin-3-yl)methyl)-3-(1-(methylsulfonyl)-1H-indol-4-yl)urea;
43. 1-(2-Tert-butyl-1H-indol-4-yl)-3-((2-(4-methylpiperidin-1-yl)-6-(trifluoromethyl)pyridin-3-yl)methyl)urea;
44. 1-(1H-indazol-4-yl)-3-((2-(4-methylpiperidin-1-yl)-6-(trifluoromethyl)pyridin-3-yl)methyl)urea;
45. 1-((2-(4-(dimethylamino)-4-phenylpiperidin-1-yl)-6-(trifluoromethyl)pyridin-3-yl)methyl)-3-(1H-indazol-4-yl)urea;
46. 1-(1-Methyl-1H-indazol-4-yl)-3-((2-(4-methylpiperidin-1-yl)-6-(trifluoromethyl)pyridin-3-yl)methyl)urea;
47. 1-((2-Butoxy-6-(trifluoromethyl)pyridin-3-yl)methyl)-3-(1-methyl-1H-indazol-4-yl)urea;
48. 1-((2-(Cyclobutylmethoxy)-6-(trifluoromethyl)pyridin-3-yl)methyl)-3-(1-methyl-1H-indazol-4-yl)urea;
49. 1-(1-Acetyl-1H-indazol-4-yl)-3-((2-(4-methylpiperidin-1-yl)-6-(trifluoromethyl)pyridin-3-yl)methyl)urea;
50. 1-(1-(2-Hydroxyethyl)-1H-indazol-4-yl)-3-((2-(4-methylpiperidin-1-yl)-6-(trifluoromethyl)pyridin-3-yl)methyl)urea;
51. 1-(6-Fluoro-1H-indazol-4-yl)-3-((2-(4-methylpiperidin-1-yl)-6-(trifluoromethyl)pyridin-3-yl)methyl)urea;
52. 1-((6-Tert-butyl-2-(4-methylpiperidin-1-yl)pyridin-3-yl)methyl)-3-(6-fluoro-1H-indazol-4-yl)urea;
53. 1-(6-Fluoro-1H-indazol-4-yl)-3-(2-(4-methylpiperidin-1-yl)-4-(trifluoromethyl)benzyl)urea;
54. 1-(2-Cyclopentyl-4-(trifluoromethyl)benzyl)-3-(6-fluoro-1H-indazol-4-yl)urea;
55. 1-(6-Chloro-1H-indazol-4-yl)-3-((2-(4-methylpiperidin-1-yl)-6-(trifluoromethyl)pyridin-3-yl)methyl)urea;
56. 1-(6-Methyl-1H-indazol-4-yl)-3-((2-(4-methylpiperidin-1-yl)-6-(trifluoromethyl)pyridin-3-yl)methyl)urea;
57. 1-(5-Chloro-1H-indazol-4-yl)-3-((2-(4-methylpiperidin-1-yl)-6-(trifluoromethyl)pyridin-3-yl)methyl)urea;
58. 1-(1H-Benzo[d]imidazol-4-yl)-3-((2-(4-methylpiperidin-1-yl)-6-(trifluoromethyl)pyridin-3-yl)methyl)urea;
59. 1-(Benzo[d]thiazol-4-yl)-3-((2-(4-methylpiperidin-1-yl)-6-(trifluoromethyl)pyridin-3-yl)methyl)urea;
60. 1-(Benzo[d]thiazol-7-yl)-3-((2-(4-methylpiperidin-1-yl)-6-(trifluoromethyl)pyridin-3-yl)methyl)urea;
61. 1-((2-(4-Methylpiperidin-1-yl)-6-(trifluoromethyl)pyridin-3-yl)methyl)-3-(quinolin-5-yl)urea;
62. 1-(4-Tert-butyl-2-(4-methylpiperidin-1-yl)benzyl)-3-(quinolin-5-yl)urea;
63. 1-(2-(4-Methylpiperidin-1-yl)-4-(trifluoromethyl)benzyl)-3-(quinolin-5-yl)urea;
64. 1-((6-Tert-butyl-2-(4-methylpiperidin-1-yl)pyridin-3-yl)methyl)-3-(quinolin-5-yl)urea;
65. 1-((2-Isopropoxy-6-(trifluoromethyl)pyridin-3-yl)methyl)-3-(quinolin-5-yl)urea;
66. 1-((2-(Neopentyloxy)-6-(trifluoromethyl)pyridin-3-yl)methyl)-3-(quinolin-5-yl)urea;
67. 1-((2-Butoxy-6-(trifluoromethyl)pyridin-3-yl)methyl)-3-(quinolin-5-yl)urea;
68. 1-((2-Cyclobutoxy-6-(trifluoromethyl)pyridin-3-yl)methyl)-3-(quinolin-5-yl)urea;
69. 1-((2-(4-Methylpiperidin-1-yl)-6-(trifluoromethyl)pyridin-3-yl)methyl)-3-(quinolin-6-yl)urea;
70. 1-((2-(4-Methylpiperidin-1-yl)-6-(trifluoromethyl)pyridin-3-yl)methyl)-3-(2-methylquinolin-6-yl)urea;
71. 1-((2-(Cyclohexylthio)-6-(trifluoromethyl)pyridin-3-yl)methyl)-3-(quinolin-7-yl)urea;
72. 1-((2-(4-Methylpiperidin-1-yl)-6-(trifluoromethyl)pyridin-3-yl)methyl)-3-(quinolin-8-yl)urea;
73. 1-((2-(4-Methylpiperidin-1-yl)-6-(trifluoromethyl)pyridin-3-yl)methyl)-3-(2-methylquinolin-8-yl)urea;
74. 1-(4-Tert-butyl-2-(4-methylpiperidin-1-yl)benzyl)-3-(2-methylquinolin-8-yl)urea;
75. 1-(Isoquinolin-5-yl)-3-((2-(4-methylpiperidin-1-yl)-6-(trifluoromethyl)pyridin-3-yl)methyl)urea;
76. 1-((6-Tert-butyl-2-(4-methylpiperidin-1-yl)pyridin-3-yl)methyl)-3-(isoquinolin-5-yl)urea;
77. 1-((2-(4-(Dimethylamino)-4-phenylpiperidin-1-yl)-6-(trifluoromethyl)pyridin-3-yl)methyl)-3-(isoquinolin-5-yl)urea;
78. 1-(1-Methylisoquinolin-5-yl)-3-((2-(4-methylpiperidin-1-yl)-6-(trifluoromethyl)pyridin-3-yl)methyl)urea;
79. 1-(1-Chloroisoquinolin-5-yl)-3-((2-(4-methylpiperidin-1-yl)-6-(trifluoromethyl)pyridin-3-yl)methyl)urea;
80. 1-(1-Methoxyisoquinolin-5-yl)-3-((2-(4-methylpiperidin-1-yl)-6-(trifluoromethyl)pyridin-3-yl)methyl)urea;
81. 1-(1-(2-Hydroxyethoxy)isoquinolin-5-yl)-3-((2-(4-methylpiperidin-1-yl)-6-(trifluoromethyl)pyridin-3-yl)methyl)urea;
82. 1-(3-Chloro-1-methoxyisoquinolin-5-yl)-3-((2-(4-methylpiperidin-1-yl)-6-(trifluoromethyl)pyridin-3-yl)methyl)urea;

83. 1-(Isoquinolin-6-yl)-3-((2-(4-methylpiperidin-1-yl)-6-(trifluoromethyl)pyridin-3-yl)methyl)urea;
84. 1-(Isoquinolin-7-yl)-3-((2-(4-methylpiperidin-1-yl)-6-(trifluoromethyl)pyridin-3-yl)methyl)urea;
85. 1-((2-(Cyclohexylthio)-6-(trifluoromethyl)pyridin-3-yl)methyl)-3-(isoquinolin-8-yl)urea;
86. 1-(1-Methylisoquinolin-8-yl)-3-((2-(4-methylpiperidin-1-yl)-6-(trifluoromethyl)pyridin-3-yl)methyl)urea;
87. 1-(3-Methylisoquinolin-8-yl)-3-((2-(4-methylpiperidin-1-yl)-6-(trifluoromethyl)pyridin-3-yl)methyl)urea;
88. 1-(5-Methoxyisoquinolin-8-yl)-3-((2-(4-methylpiperidin-1-yl)-6-(trifluoromethyl)pyridin-3-yl)methyl)urea;
89. 1-(4-Hydroxyquinazolin-8-yl)-3-((2-(4-methylpiperidin-1-yl)-6-(trifluoromethyl)pyridin-3-yl)methyl)urea;
90. 1-((2-(4-Methylpiperidin-1-yl)-6-(trifluoromethyl)pyridin-3-yl)methyl)-3-(quinoxalin-5-yl)urea;
91. 1-((2-(4-Methylpiperidin-1-yl)-6-(trifluoromethyl)pyridin-3-yl)methyl)-3-(quinazolin-7-yl)urea;
92. 1-((2-(4-Methylpiperidin-1-yl)-6-(trifluoromethyl)pyridin-3-yl)methyl)-3-(quinolin-2-yl)urea;
93. 1-((2-(4-Methylpiperidin-1-yl)-6-(trifluoromethyl)pyridin-3-yl)methyl)-3-(quinolin-7-yl)urea;
94. 1-((2-(4-Methylpiperidin-1-yl)-6-(trifluoromethyl)pyridin-3-yl)methyl)-3-(phthalazin-6-yl)urea;
95. 1-((2-(4-Methylpiperidin-1-yl)-6-(trifluoromethyl)pyridin-3-yl)methyl)-3-(quinazolin-6-yl)urea;
96. 1-(Isoquinolin-8-yl)-3-((2-(4-methylpiperidin-1-yl)-6-(trifluoromethyl)pyridin-3-yl)methyl)urea;
97. 1-((2-(4-Methylpiperidin-1-yl)-6-(trifluoromethyl)pyridin-3-yl)methyl)-3-(1,7-naphthyridin-8-yl)urea;

optionally in the form of a single stereoisomer or a mixture of stereoisomers, in the form of the free compound and/or a physiologically acceptable salt thereof.

Furthermore, preference may be given to compounds according to the invention that cause a 50 percent displacement of capsaicin, which is present at a concentration of 100 nM, in a FLIPR assay with CHO K1 cells which were transfected with the human VR1 gene at a concentration of less than 2,000 nM, preferably less than 1,000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The substituted compounds according to the invention of the aforementioned general formula (I) and corresponding stereoisomers and also the respective corresponding acids, bases, salts and solvates are toxicologically safe and are therefore suitable as pharmaceutical active ingredients in pharmaceutical compositions.

The present invention therefore further relates to a pharmaceutical composition containing at least one compound according to the invention of the above-indicated formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect.

Likewise, the pharmaceutical compositions according to the invention are preferably suitable for the inhibition and/or treatment of disorders or diseases which are mediated, at least in part, by vanilloid receptors 1.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of the above-indicated formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

The pharmaceutical composition according to the invention is preferably suitable for the treatment and/or inhibition of one or more disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the pharmaceutical composition according to the invention is suitable for the treatment and/or inhibition of one or more disorders and/or diseases selected from the group consisting of pain, preferably of pain selected from the group consisting of acute pain, chronic pain, neuropathic pain, visceral pain and joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, the pharmaceutical composition according to the invention is suitable for the treatment and/or inhibition of pain, preferably of pain selected from the group consisting of acute pain, chronic pain, neuropathic pain and visceral pain.

The present invention further relates to a substituted compound according to general formula (I) and also if appropriate to a substituted compound according to general formula (I) and one or more pharmaceutically acceptable auxiliaries for use in vanilloid receptor 1-(VR1/TRPV1) regulation, preferably for use in vanilloid receptor 1-(VR1/TRPV1) inhibition and/or vanilloid receptor 1-(VR1/TRPV1) stimulation.

The present invention therefore further relates to a substituted compound according to general formula (I) and also if appropriate to a substituted compound according to general formula (I) and one or more pharmaceutically acceptable auxiliaries for use in the inhibition and/or treatment of disorders and/or diseases which are mediated, at least in part, by vanilloid receptors 1.

In particular, the present invention therefore further relates to a substituted compound according to general formula (I) and also if appropriate to a substituted compound according to general formula (I) and one or more pharmaceutically acceptable auxiliaries for use in the inhibition and/or treatment of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particularly preferred is a substituted compound according to general formula (I) and also if appropriate to a substituted compound according to general formula (I) and one or more pharmaceutically acceptable auxiliaries for use in the inhibition and/or treatment of pain, preferably of pain selected from the group consisting of acute pain, chronic pain, neuropathic pain and visceral pain.

The present invention further relates to the use of at least one compound according to general formula (I) and also if appropriate of one or more pharmaceutically acceptable auxiliaries for the preparation of a pharmaceutical composition for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further for the inhibition and/or treatment of disorders and/or diseases which are mediated, at least in part, by vanilloid receptors 1, such as e.g. disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Another aspect of the present invention is a method for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further, a method of treatment and/or inhibition of disorders and/or diseases, which are mediated, at least in part, by vanilloid receptors 1, in a mammal, preferably of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174).

The present invention further relates to processes for preparing inventive compounds of the above-indicated general formula (I).

In particular, the compounds according to the present invention of general formula (I) can be prepared by a process according to which at least one compound of general formula (II),

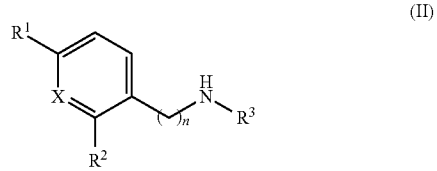

(II)

in which X, $R^1$, $R^2$, $R^3$ and n have one of the foregoing meanings, is reacted in a reaction medium, if appropriate in the presence of at least one suitable coupling reagent, if appropriate in the presence of at least one base, with a compound of general formula (III) with D=OH or Hal,

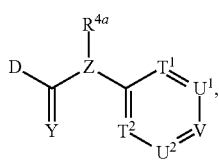

D = OH, Hal in which Hal represents a halogen, preferably Br or Cl, and $R^{4a}$, Y, $T^1$, $U^1$, V, $T^2$ and $U^2$ each have one of the foregoing meanings and Z denotes C—$R^{4b}$, wherein $R^{4b}$ has one of the foregoing meanings, in a reaction medium, if appropriate in the presence of at least one suitable coupling reagent, if appropriate in the presence of at least one base, to form a compound of general formula (I),

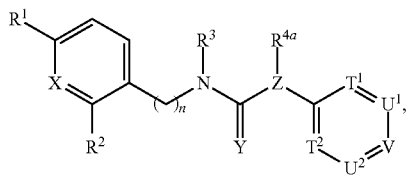

in which Z represents $CR^{4b}$ and X, $R^1$, $R^2$, $R^3$, $R^{4a}$, $R^{4b}$, Y, $U^1$, V, $T^2$ and $U^2$ and n have one of the foregoing meanings;

or in that at least one compound of general formula (II),

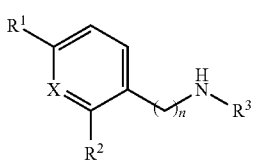

in which X, $R^1$, $R^2$, $R^3$ and n have one of the foregoing meanings, is reacted to form a compound of general formula (IV)

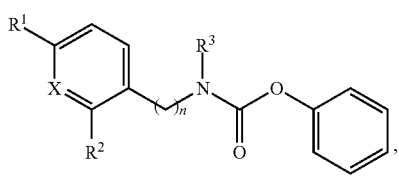

in which X, $R^2$, $R^3$ and n have one of the foregoing meanings, in a reaction medium, in the presence of phenyl chloroformate, if appropriate in the presence of at least one base and/or at least one coupling reagent, and said compound is if appropriate purified and/or isolated, and a compound of general formula (IV) is reacted with a compound of general formula (V),

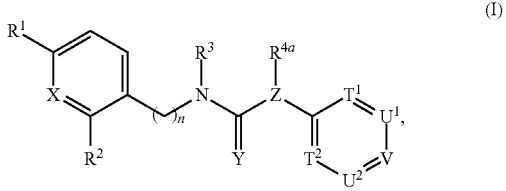

in which $R^{4a}$, $T^1$, $U^1$, V, $T^2$ and $U^2$ have one of the foregoing meanings, and Z denotes N, in a reaction medium, if appropriate in the presence of at least one suitable coupling reagent, if appropriate in the presence of at least one base, to form a compound of general formula (I),

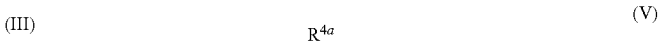

in which Z represents N and X, $R^1$, $R^2$, $R^3$, $R^{4a}$, Y, $T^1$, $U^1$, V, $T^2$ and $U^2$ and n have one of the foregoing meanings.

The reaction of compounds of the above-indicated general formulae (II) and (V) with carboxylic acids of the above-indicated general formula (III), particularly with D=OH, to form compounds of the above-indicated general formula (I) is carried out preferably in a reaction medium selected from the group consisting of diethyl ether, tetrahydrofuran, acetonitrile, methanol, ethanol, (1,2)-dichloroethane, dimethylformamide, dichloromethane and corresponding mixtures, if appropriate in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyldiimidazole (CDI), N—[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), if appropriate in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the above-indicated general formulae (II) and (V) with carboxylic acid halides of the above-indicated general formula (III) with D=Hal, in which Hal represents a halogen as the leaving group, preferably a chlorine or bromine atom, to form compounds of the above-indicated general formula (I) is carried out in a reaction medium preferably selected from the group consisting of diethyl ether, tetrahydrofuran, acetonitrile, methanol, ethanol, dimethylformamide, dichloromethane and corresponding mixtures, if appropriate in the presence of an organic or inorganic base, preferably selected from the group consisting of triethylamine, dimethylaminopyridine, pyridine and diisopropylamine, at temperatures of from −70° C. to 100° C.

The compounds of the above-indicated formulae (II), (III), (IV), and (V) are each commercially available and/or can be prepared using conventional processes known to the person skilled in the art. In particular, processes to prepare these compounds are e.g. disclosed in WO 2007/045462-A2, WO 2008/125342-A2 and WO 2008/125337-A2. The corresponding parts of these references are hereby deemed to be part of the disclosure.

All reactions which can be applied for synthesizing the compounds according to the present invention can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps of the reaction sequences which can be applied for synthesizing the compounds according to the present invention as well as the respective purification and/or isolation of intermediate or end products, can be carried out partly or completely under an inert gas atmosphere, preferably under a nitrogen atmosphere.

The substituted compounds according to the invention can be isolated both in the form of their free bases, their free acids and also in the form of corresponding salts, in particular physiologically compatible salts, i.e. physiologically acceptable salts.

The free bases of the respective substituted compounds according to the invention can be converted into the corresponding salts, preferably physiologically compatible salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of the aforementioned general formula (I) and of corresponding stereoisomers can likewise be converted into the corresponding physiologically compatible salts using the free acid or a salt of a sugar additive, such as for example saccharin, cyclamate or acesulfame.

Accordingly, the free acids of the substituted compounds according to the invention can be converted into the corresponding physiologically compatible salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ aliphatic residue.

The substituted compounds according to the invention and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds according to the invention are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulfonic acid, to be separated from one another.

The chemicals and reaction components used in the reactions and schemes described below are available commercially or in each case can be prepared by conventional methods known to the person skilled in the art.

General Reaction Scheme (Scheme 1):

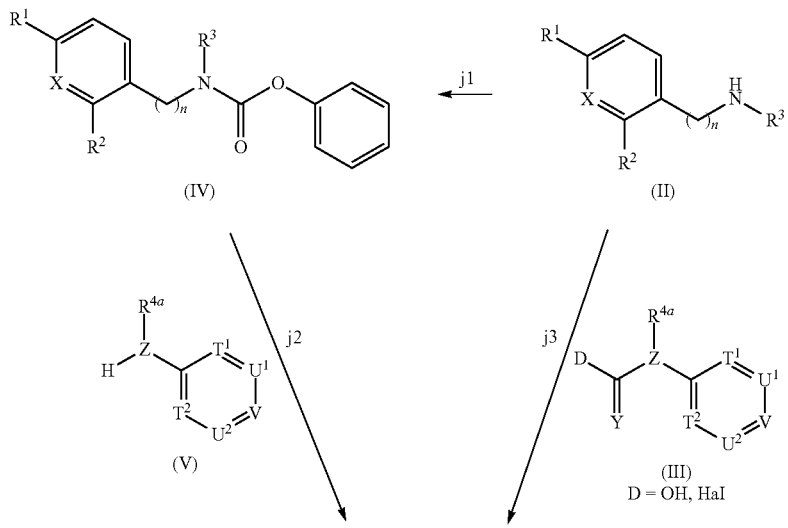

-continued

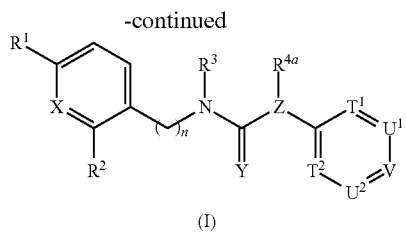

(I)

In step j1 the compound (II) can be converted into the compound (IV) by means of methods known to the person skilled in the art, such as using phenyl chloroformate, if appropriate in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j2 the amine (V) can be converted into the urea compound (I) (wherein Z=N). This can be achieved by reaction with (IV) by means of methods with which the person skilled in the art is familiar, if appropriate in the presence of a base.

In step j3 the amine (II) can be converted into the amide (I) (wherein A=C—$R^{4b}$). This can for example be achieved by reaction with an acid halide, preferably a chloride, of formula (III) with D=Hal, by means of methods with which the person skilled in the art is familiar, if appropriate in the presence of a base or by reaction with an acid of formula (III) with D=OH, if appropriate in the presence of a suitable coupling reagent, for example HATU or CDI, if appropriate with the addition of a base. Further, the amine (II) may be converted into the amide (I) (wherein Z=C—$R^{4b}$) by reaction of a compound (IIIa)

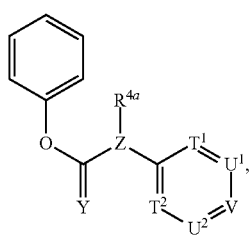

(IIIa)

by means of methods with which the person skilled in the art is familiar, if appropriate in the presence of a base.

General Reaction Scheme (Scheme 2):

The compounds according to general formula (I), wherein Z=N, may be further prepared by a reaction sequence according to general reaction scheme 2:

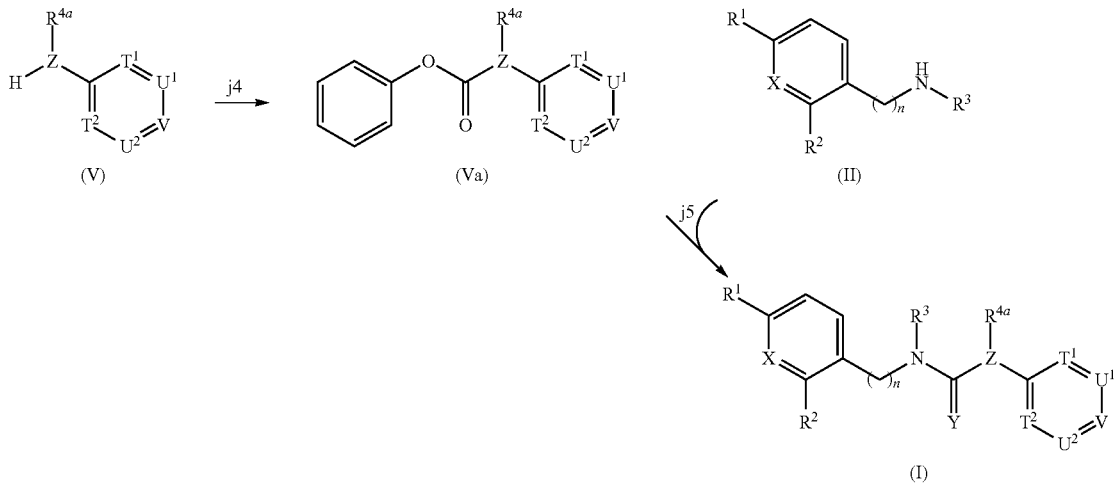

In step j4 the compound (V) can be converted into the compound (Va), wherein Z=N, by means of methods known to the person skilled in the art, such as using phenyl chloroformate, if appropriate in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j5 the amine (II) can be converted into the urea compound (I) (wherein Z=N). This can be achieved by reaction with (Va) by means of methods with which the person skilled in the art is familiar, if appropriate in the presence of a base.

The methods with which the person skilled in the art is familiar for carrying out the reaction steps j1 to j5 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

The invention will be described hereinafter with the aid of a number of examples. This description is intended merely by way of example and does not limit the general idea of the invention.

EXAMPLES

The indication "equivalents" ("eq.") means molar equivalents, "RT" means room temperature (23±7° C.), "M" are indications of concentration in mol/l, "aq." means aqueous, "sat." means saturated, "sol." means solution, "conc." means concentrated.

Further Abbreviations:
d days
BINAP 2,2'-bis(diphenylphosphino)-1,1'-binaphthyl
brine saturated aqueous sodium chloride solution
CC column chromatography on silica gel
DCM dichloromethane
DMAP 4-dimethylaminopyridine
DMF N,N-dimethylformamide
DPPF 1,1'-bis(diphenylphosphino)ferrocene
ether diethyl ether
EtOAc ethyl acetate
EtOH ethanol
h hour(s)
H₂O water
m/z mass-to-charge ratio
MeOH methanol
MeCN acetonitrile
min minutes
MS mass spectrometry
NEt₃ triethylamine
TLC thin layer chromatography
THF tetrahydrofuran
v/v volume to volume
w/w weight in weight The yields of the compounds prepared were not optimized. All temperatures are uncorrected. All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The stationary phase used for the column chromatography was silica gel 60 (0.04-0.063 mm) from E. Merck, Darmstadt. The mixing ratios of solvents or eluents for chromatography are specified in v/v.

All the intermediate products and example compounds were analytically characterized by means of ¹H-NMR spectroscopy. In addition, mass spectrometry tests (MS, m/z for [M+H]⁺) were carried out for all the example compounds and selected intermediate products.

Synthesis of the Example Compounds:

The example compounds 1, 5, 8-9, 11-12, 14-15, 17-24, 26-27, 29-49, 51-80 and 82-97 were obtained by one of the methods disclosed above. The example compounds 2-4, 6-7, 10, 13, 16, 25, 28, 50 and 81 can be obtained by one of the methods disclosed above. The person skilled in the art is aware which method has to be employed to obtain a particular example compound.

Detailed Synthesis of Selected Example Compounds

Synthesis of example 1: 1-(6,7-dihydro-5H-cyclopenta[b]pyridin-3-yl)-3-((2-(4-methyl-piperidin-1-yl)-6-(trifluoromethyl)pyridin-3-yl)methyl)urea

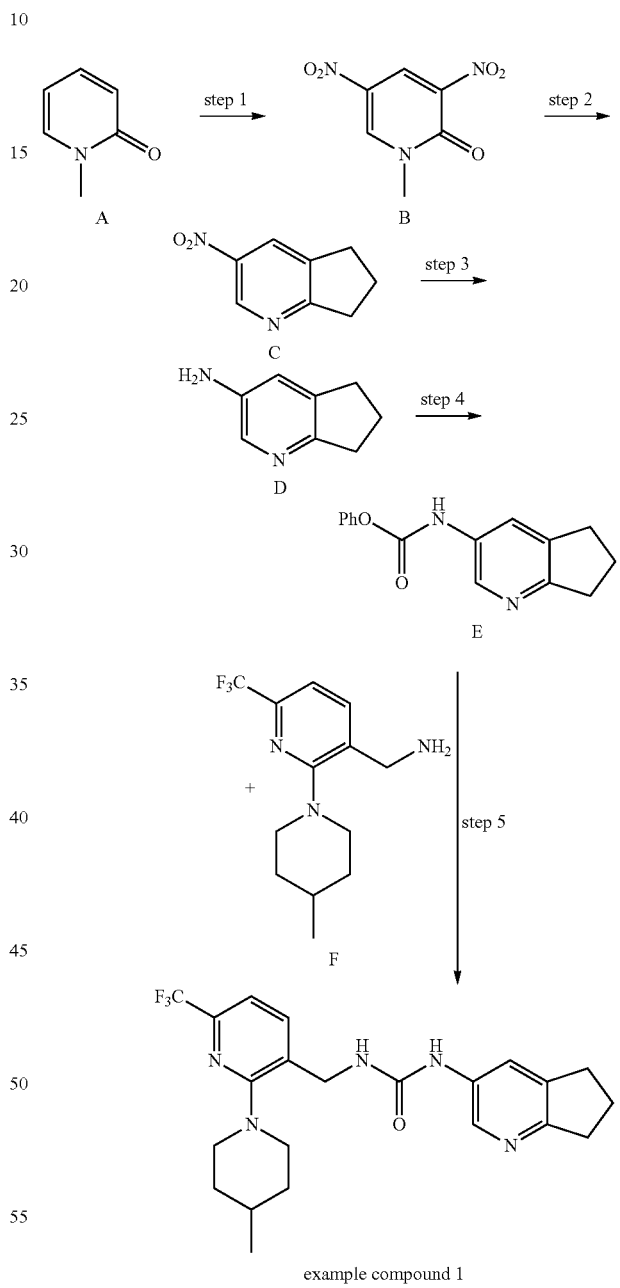

example compound 1

Step 1: To a solution of N-methylpyridinone (A) (3 g, 27.49 mmol) in H₂SO₄ (100 mL) was slowly added HNO₃ (60%) (0.3 mL, 137.45 mmol) at room temperature. The reaction mixture was heated to 100° C. for 4 h. TLC showed complete consumption of starting material. The reaction mixture was cooled to room temperature and neutralized with NaHCO₃. The mixture was extracted with ethyl acetate and washed with water and brine. The extract was dried over MgSO₄ and concentrated under reduced pressure to give 1-methyl-3,5-dinitropyridin-2(1H)-one (B) (1.19 g, 22%)

Step 2: A mixture of 1-methyl-3,5-dinitropyridin-2(1H)-one (B) (947 mg, 4.76 mmol), cyclohexanone (0.5 mL, 5.70 mmol) and ammonia solution (1 M) in methanol (50 mL) was heated to 70° C. for 3 h under N₂. TLC showed complete consumption of starting material. The reaction mixture was removed in vacuo and extracted with ethyl acetate. The organic part was washed with water and brine. The organic layer was dried over MgSO₄ and concentrated under reduced pressure to afford crude which was purified by column chromatography to afford 3-nitro-6,7-dihydro-5H-cyclopenta[b]pyridine (C). (340 mg, 44%)

Step 3: 3-Nitro-6,7-dihydro-5H-cyclopenta[b]pyridine (C) (340 mg, 2.07 mmol) was dissolved in methanol. Pd/C (40 mg) was added to it. The resulting mixture was stirred at room temperature for 2 h under H₂. TLC showed complete consumption of starting material. The mixture was filtered through celite bed and the filtrate was concentrated under reduced pressure to afford desired 6,7-dihydro-5H-cyclopenta[b]pyridin-3-amine (D). (250 mg, 90%)

Step 4: 6,7-Dihydro-5H-cyclopenta[b]pyridin-3-amine (D) (250 mg, 1.86 mmol) was dissolved in acetonitrile. The reaction mixture was added pyridine (0.18 mL, 2.23 mmol) and phenyl chloroformate (0.26 mL, 2.05 mmol) and stirred at room temperature for 3 h under N₂. TLC showed complete consumption of starting material. The reaction mixture was diluted with water and extracted with ethyl acetate. The organic part was washed with water and brine. The organic layer was dried over MgSO₄ and concentrated under reduced pressure. The crude was purified by column chromatography to give phenyl 6,7-dihydro-5H-cyclopenta[b]pyridin-3-yl-carbamate (E). (372 mg, 78%)

Step 5: To a solution of phenyl 6,7-dihydro-5H-cyclopenta[b]pyridin-3-ylcarbamate (E) (80 mg, 0.31 mmol) in DMF was added DMAP (38 mg, 0.31 mmol) and (2-(4-methylpiperidin-1-yl)-6-(trifluoromethyl)pyridin-3-yl)methanamine (F) (90 mg, 0.33 mmol) at room temperature. The reaction mixture was heated to 50° C. for 14 h. TLC showed complete consumption of starting material. The reaction mixture was diluted with water and extracted with EtOAc. The organic part was washed with water and brine. The organic layer was dried over MgSO₄ and concentrated under reduced pressure. The crude was purified by column chromatography to give pure 1-(6,7-dihydro-5H-cyclopenta[b]pyridin-3-yl)-3-((2-(4-methylpiperidin-1-yl)-6-(trifluoromethyl)pyridin-3-yl)methyl)urea (example compound I) (104 mg, 76%).

¹H NMR (300 MHz, CDCl₃): δ 8.10 (s, 1H, Ar—H), 7.72 (br. s, 1H, Ar—H), 7.70 (d, 1H, J=7.68 Hz, Ar—H), 7.23 (d, 1H, J=7.71 Hz, Ar—H), 6.89 (br. s, 1H, Ar—NH) 5.69 (br. s, 1H, RCO—NH), 4.49 (s, 2H, Ar—CH₂), 3.35 (d, 2H, J=12.63 Hz, piperidine-H), 2.91 (m, 6H, indan and piperidine-H), 2.13 (m, 2H, indan-H), 1.72 (d, 2H, J=10.98 Hz, piperidine-H), 1.54 (m, 1H, piperidine-H), 1.19 (m, 2H, piperidine-H), 0.96 (d, 3H, J=6.42 Hz, piperidine-CH₃).

Synthesis of example 5: 1-((2-(4-methylpiperidin-1-yl)-6-(trifluoromethyl)pyridin-3-yl)methyl)-3-(1H-pyrazolo[3,4-b]pyridin-5-yl)urea

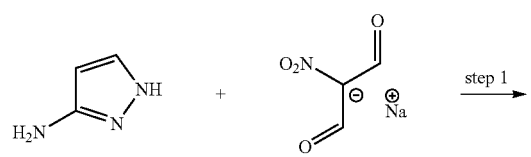

example compound 5

Step 1: 1H-pyrazol-3-amine (427 mg, 5.139 mmol) was dissolved in ethanol (10 mL) and 12M HCl (0.5 mL) was added to the stirred solution, followed by granulated zinc chloride (300 mg). The mixture was heated to reflux, and to the mixture was added a solution of 5.139 mmol of the source of the appropriate 1,3-dicarbonyl compound (sodium 2-nitro-1,3-dioxopropan-2-ide) in ethanol (5 mL). After 1 h the reaction mixture was poured into ice-cold water (15 mL), the resultant solution was made alkaline with concentrated aqueous ammonia, and the product was isolated by trichloromethane extraction. The product 5-nitro-1H-pyrazolo[3,4-b]pyridine (279 mg, 33%) (A) was isolated and purified by column chromatography.

Step 2: 10% Palladium on carbon (40 mg) was added to a solution of 5-nitro-1H-pyrazolo[3,4-b]pyridine (A) (308 mg, 1.876 mmol) in ethanol and tetrahydrofuran and the mixture was charged with H₂ (gas). After stirring the reaction mixture for 15 h, the mixture was filtered using celite and purified by column chromatography. The desired product 1H-pyrazolo[3,4-b]pyridin-5-amine (B) (73 mg) was obtained as 89% yield.

Step 3: 1H-Pyrazolo[3,4-b]pyridin-5-amine (B) (212 mg, 1.58 mmol) was dissolved in acetonitrile. To the reaction mixture was added pyridine (0.15 mL, 1.896 mmol) and phenyl chloroformate (0.2 mL, 1.659 mmol) and stirred at room temperature for 30 min under N₂. TLC showed complete consumption of starting material. The reaction mixture was diluted with water and extracted with ethyl acetate. The organic part was washed with water and brine. The organic layer was dried over MgSO₄ and concentrated under reduced pressure. The crude was purified by column chromatography to give phenyl 1H-pyrazolo[3,4-b]pyridin-5-ylcarbamate (C). (285 mg, 71%)

Step 4: To a solution of phenyl 1H-pyrazolo[3,4-b]pyridin-5-ylcarbamate (C) (84 mg, 0.329 mmol) in acetonitrile was added DMAP (40 mg, 0.329 mmol) and (2-(4-methylpiperidin-1-yl)-6-(trifluoromethyl)pyridin-3-yl)methanamine (D) (90 mg, 0.329 mmol) at room temperature. The reaction mixture was heated to 50° C. for 15 h. TLC showed complete consumption of starting material. The reaction mixture was diluted with water and extracted with ethyl acetate. The organic part was washed with water and brine. The organic layer was dried over MgSO₄ and concentrated under reduced pressure. The crude was purified by column chromatography to give pure 1-((2-(4-methylpiperidin-1-yl)-6-(trifluoromethyl)pyridin-3-yl)methyl)-3-(1H-pyrazolo[3,4-b]pyridin-5-yl)urea (example compound 5) (102 mg, 71%).

¹H NMR (300 MHz, DMSO) 9.23 (s, 1H, Ar—H), 9.10 (bs, 1H, Ar—NH), 8.48 (d, 1H, J=2.37 Hz, Ar—H), 8.08 (d, 1H, J=2.4 Hz, Ar—H), 7.83 (d, 1H, J=7.71 Hz, Ar—H) 7.44 (d, 1H, J=7.68 Hz, Ar—H), 7.12 (bt, 1H, RCO—NH), 6.65 (s, 1H, Ar—H), 4.37 (d, 2H, Ar—CH₂), 3.41 (d, 2H, J=12.63 Hz, Piperidine-Hs), 2.80 (t, 2H, Piperidine-Hs), 1.73 (d, 2H, J=10.98 Hz, Piperidine-Hs), 1.56 (bs, 1H, Piperidine-Hs), 1.30 (t, 2H, Piperidine-Hs), 0.97 (d, 3H, J=6.39 Hz, Piperidine-CH₃).

Synthesis of example 11: 1-((2-(cyclohexylthio)-6-(trifluoromethyl)pyridin-3-yl)methyl)-3-(quinolin-2-yl)urea

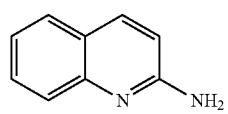

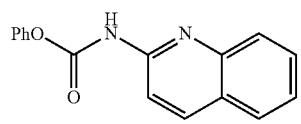

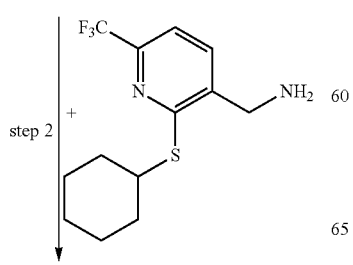

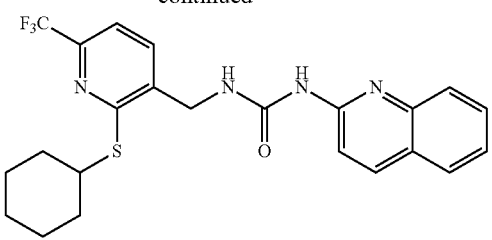

example compound 11

Step 1: 2-Aminoquinoline (300 mg, 2.08 mmol) was dissolved in acetonitrile. To the reaction mixture was added pyridine (0.2 mL, 2.5 mmol) and phenyl chloroformate (0.27 mL, 2.18 mmol), respectively and stirred at room temperature for 1 h. The reaction mixture was diluted with water and extracted with ethyl acetate. The organic layer was concentrated under reduced pressure. The crude was purified by column chromatography to give phenyl quinolin-2-ylcarbamate (296 mg, 54%).

Step 2: Phenyl quinolin-2-ylcarbamate (A) (60 mg, 0.23 mmol) and (2-(cyclohexylthio)-6-(trifluoromethyl)pyridin-3-yl)methanamine (69 mg, 0.24 mmol) was dissolved in dimethyl sulfoxide. Then triethylamine (0.06 mL, 0.45 mmol) was added. The mixture was stirred at room temperature for 12 h. The reaction mixture was diluted with water and extracted with ethyl acetate. The organic layer was concentrated under reduced pressure. The crude was purified by column chromatography to give 1-((2-(cyclohexylthio)-6-(trifluoromethyl)pyridin-3-yl)methyl)-3-(quinolin-2-yl)urea (example compound II) (55 mg, 53%).

¹H NMR (300 MHz, CD₃OD): δ 8.17 (d, 1H, J=9.18 Hz, Ar—H), 7.86 (m, 3H, Ar—H), 7.67 (t, 1H, J=6.78 Hz, Ar—H), 7.46 (m, 2H, Ar—H), 7.10 (d, 1H, J=10.32 Hz, Ar—H), 4.58 (s, 2H, Ar—CH₂), 4.05 (m, 1H), 2.15 (m, 2H, cyclohexane-CH₂), 1.81 (m, 2H, cyclohexane-CH₂), 1.62 (m, overlapped, 6H, cyclohexane-CH₂).

Synthesis of example 12: 1-((2-(4-methylpiperidin-1-yl)-6-(trifluoromethyl)pyridin-3-yl)methyl)-3-(quinolin-3-yl)urea

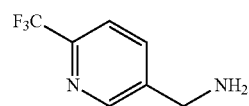

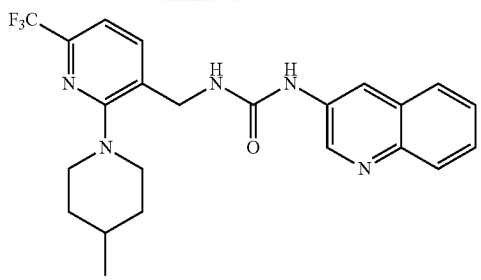

example compound 12

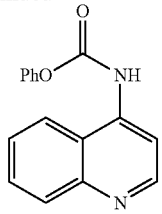

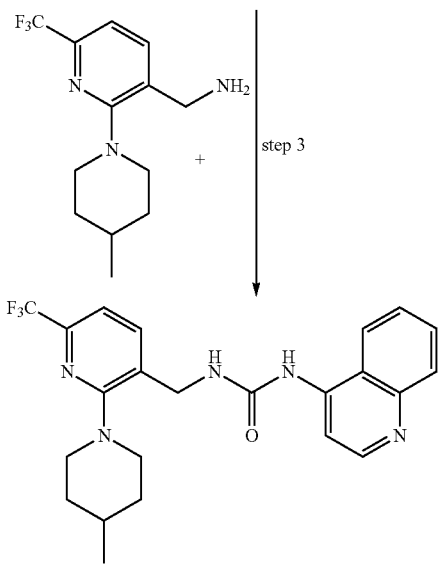

example compound 17

Step 1: 1,1'-Carbonyldiimidazole (CU) (1.1 eq.) was added to 3-aminoquinoline (1 eq.) dissolved in methylene chloride. The mixture was stirred during 12 h at room temperature. After that (2-(4-methylpiperidin-1-yl)-6-(trifluoromethyl)pyridin-3-yl)methanamine (0.98 eq.) was added to the mixture. After 12 h the solvent was evaporated and the mixture was purified by column chromatography (silica gel: 100-200; eluent: 50% ethyl acetate in n-hexane) and give the desired 1-((2-(4-methylpiperidin-1-yl)-6-(trifluoromethyl)pyridin-3-yl)methyl)-3-(quinolin-3-yl)urea (example compound 12) (100 mg, 42%).

$^1$H NMR (300 MHz, CDCl$_3$) δ 8.57 (d, 1H, J=2.55 Hz Ar—H), 8.54 (s, 1H, Ar—H), 8.45 (d, 1H, J=2.76 Hz, Ar—H), 7.85 (d, 1H, J=8.07 Hz, Ar—H), 7.57-7.65 (m, 2H, Ar—H) 7.38-7.52 (m, 2H, Ar—H), 7.10 (d, 1H, J=7.66 Hz, Ar—H), 6.23 (bt, 1H, J=12.63 Hz, ArCH$_2$—NH), 4.40-4.50 (m, 2H, Ar—CH$_2$), 3.20-3.33 (m, 2H, piperidine-H), 2.70-2.82 (m, 2H, piperidine-H), 1.55-1.68 (m, 2H, piperidine-H), 1.47 (m, 1H, piperidine-H), 1.09-1.30 (m, 2H, piperidine-H), 0.88 (d, 3H, J=6.39 Hz, piperidine-CH$_3$).

Synthesis of example 17: 1-((2-(4-Methylpiperidin-1-yl)-6-(trifluoromethyl)pyridin-3-yl)methyl)-3-(quinolin-4-yl)urea

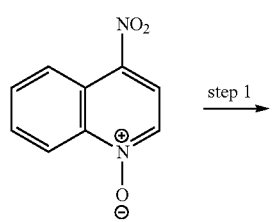

step 1

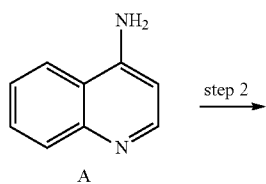

A step 2

Step 1: 4-Nitroquinoline-N-oxide (100 mg, 0.53 mmol) and Fe (264 mg, 4.24 mmol) was dissolved in 2 mL acetic acid and refluxed for 3 h. The reaction mixture was cooled to room temperature and basified by using Na$_2$CO$_3$ to pH ≥7. The solution was filtered through celite bed and the filtrate was diluted with water and extracted with ethyl acetate. The organic layer was concentrated under reduced pressure to afford the desired quinolin-4-amine (A) (76 mg, 99%).

Step 2: Quinolin-4-amine (A) (76 mg, 0.53 mmol) was dissolved in dichloromethane. To the reaction mixture was added triethylamine (0.09 mL, 0.63 mmol) and phenyl chloroformate (0.07 mL, 0.55 mmol) and stirred at room temperature for 1 h. The reaction mixture was concentrated under reduced pressure to afford the crude phenyl quinolin-4-ylcarbamate which was directly used for next step without purification.

Step 3: Phenyl quinolin-4-ylcarbamate (crude 139 mg, 0.53 mmol) and (2-(4-methylpiperidin-1-yl)-6-(trifluoromethyl)pyridin-3-yl)methanamine (144 mg, 0.53 mmol) were dissolved in dimethyl sulfoxide. Then triethylamine (0.15 mL, 1.06 mmol) was added to it. The mixture was stirred at room temperature for 12 h. The reaction mixture was diluted with water and extracted with ethyl acetate. The organic layer was concentrated under reduced pressure.

The crude was purified by column chromatography to give 1-((2-(4-methylpiperidin-1-yl)-6-(trifluoromethyl)pyridin-3-yl)methyl)-3-(quinolin-4-yl)urea (example compound 17) (67 mg, 29%).

$^1$H NMR (300 MHz, CD$_3$OD): δ 8.65 (d, 1H, J=5.31 Hz, Ar—H), 8.25 (d, 1H, J=5.31 Hz, Ar—H), 8.15 (d, 1H, J=8.22 Hz, Ar—H), 7.99 (d, 1H, J=8.4 Hz, Ar—H), 7.89 (d, 1H, J=7.89 Hz, Ar—H), 7.78 (t, 1H, J=5.49 Hz, Ar—H), 7.64 (t, 1H, J=8.25 Hz, Ar—H), 7.35 (d, 1H, J=7.68 Hz, Ar—H), 4.55 (s, 2H, Ar—CH$_2$), 3.50 (m, 2H, piperidine-CH$_2$), 2.92 (m, 2H, piperidine-CH$_2$), 1.79 (m, 2H, piperidine-CH$_2$), 1.59 (m, 1H, piperidine-CH), 1.48 (m, 2H, piperidine-CH$_2$), 1.02 (d, 3H, J=6.42 Hz, piperidine-CH$_3$).

Synthesis of example 18: 1-(isoquinolin-4-yl)-3-((2-(4-methylpiperidin-1-yl)-6-(trifluoromethyl)pyridin-3-yl)methyl)urea

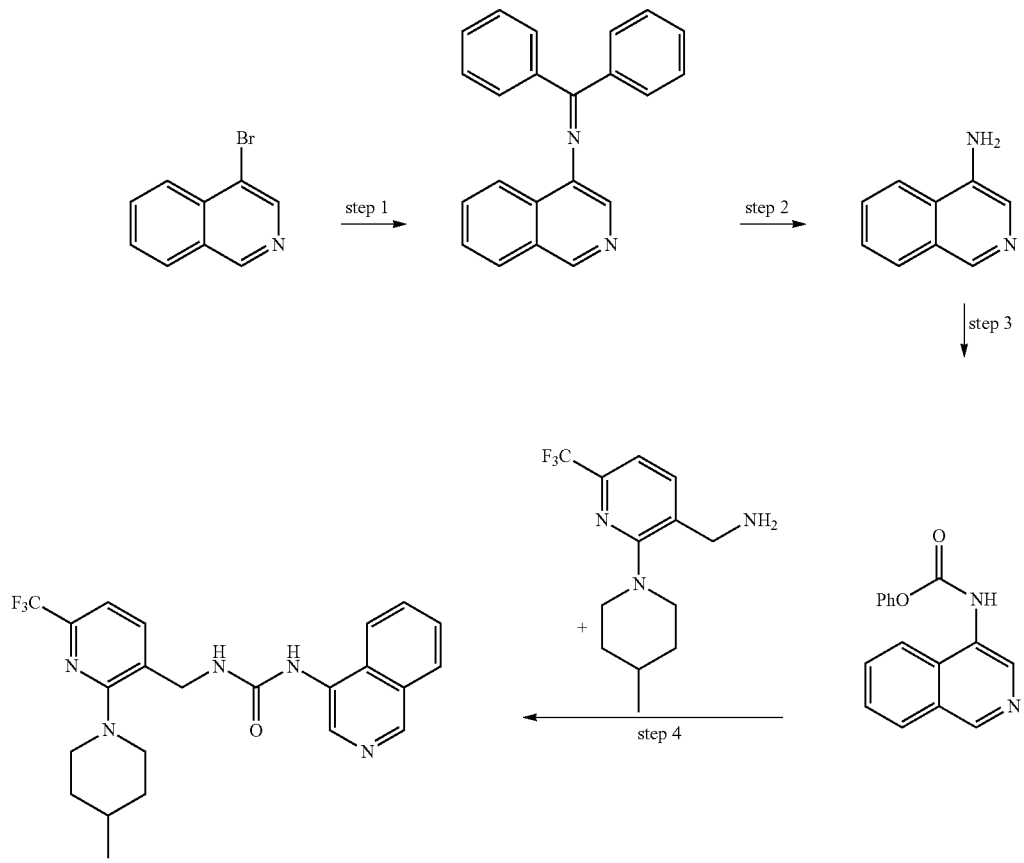

example compound 18

Step 1: In a 250 mL round flask 4-bromoisoquinoline (1 g, 4.81 mmol), benzophenone imine (2.41 mL, 14.42 mL), Pd(OAc)$_2$ (33 mg, 0.14 mmol), BINAP (299 mg, 0.05 mmol), DPPF (266 g, 0.05 mmol) and triethylamine (0.17 mL, 1.20 mmol) were concentrated in vacuum for 15 min and then dissolved in 50 mL anhydrous toluene at room temperature for 20 min. Cs$_2$CO$_3$ (2.35 g, 7.21 mmol) was added to the reaction mixture. The reaction mixture was heated at 110° C. for 18 h. The reaction mixture was cooled to room temperature and filtered. The filtrate was concentrated under reduced pressure to afford the crude which was purified by column chromatography to give N-(diphenylmethylene)-isoquinolin-4-amine (853 mg, 58%).

Step 2: N-(Diphenylmethylene)isoquinolin-4-amine (650 mg, 2.14 mmol) was dissolved in 25 mL tetrahydrofuran and 25 mL ethanol and cooled to 0° C. by using an ice bath. 2M HCl (4.5 mL) was added dropwise at 0° C. The reaction mixture was stirred for another 3 h at room temperature. The reaction mixture was basified by using Na$_2$CO$_3$ to pH 7. The reaction mixture was diluted with water and extracted with ethyl acetate. The organic layer was concentrated under reduced pressure to afford the crude which was purified by column chromatography to isoquinolin-4-amine (296 mg, 97%).

Step 3: Isoquinolin-4-amine (296 mg, 2.05 mmol) was dissolved in acetonitrile. To the reaction mixture was added pyridine (0.20 mL, 2.46 mmol) and phenyl chloroformate (0.27 mL, 2.15 mmol), respectively and stirred at room temperature for 1 h. The reaction mixture was diluted with water and extracted with ethyl acetate. The organic layer was concentrated under reduced pressure. The crude was purified by column chromatography to give phenyl isoquinolin-4-ylcarbamate (318 mg, 59%).

Step 4: Phenyl isoquinolin-4-ylcarbamate (72 mg, 0.27 mmol) and (2-(4-methylpiperidin-1-yl)-6-(trifluoromethyl)pyridin-3-yl)methanamine (78 mg, 0.29 mmol) was dissolved in dimethyl sulfoxide. Then triethylamine (0.08 mL, 0.54 mmol) was added to it. The mixture was stirred at room temperature for 15 h. The reaction mixture was diluted with water and extracted with ethyl acetate. The organic layer was concentrated under reduced pressure. The crude was purified by column chromatography to give the desired 1-(isoquinolin-4-yl)-3-((2-(4-methylpiperidin-1-yl)-6-(trifluoromethyl)pyridin-3-yl)methyl)urea (example compound 18) (60 mg, 50%).

$^1$H NMR (300 MHz, CD$_3$OD): δ 9.02 (s, 1H, Ar—H), 8.80 (s, 1H, Ar—H), 8.15 (d, 1H, J=8.04 Hz, Ar—H), 8.09 (d, 1H, J=8.25 Hz, Ar—H), 7.89 (m, overlapped, 2H, Ar—H), 7.75 (t, 1H, J=7.53 Hz, Ar—H), 7.37 (d, 1H, J=7.68 Hz, Ar—H), 4.52 (s, 2H, Ar—CH$_2$), 3.48 (m, 2H, piperidine-CH$_2$), 2.90 (m, 2H, piperidine-CH$_2$), 1.78 (m, 2H, piperidine-CH$_2$), 1.58 (m, 1H, piperidine-CH), 1.44 (m, 2H, piperidine-CH$_2$), 1.01 (d, 3H, J=6.39 Hz, piperidine-CH$_3$).

Synthesis of example 19: 1-((2-(cyclohexylthio)-6-(trifluoromethyl)pyridin-3-yl)methyl)-3-(isoquinolin-4-yl)urea

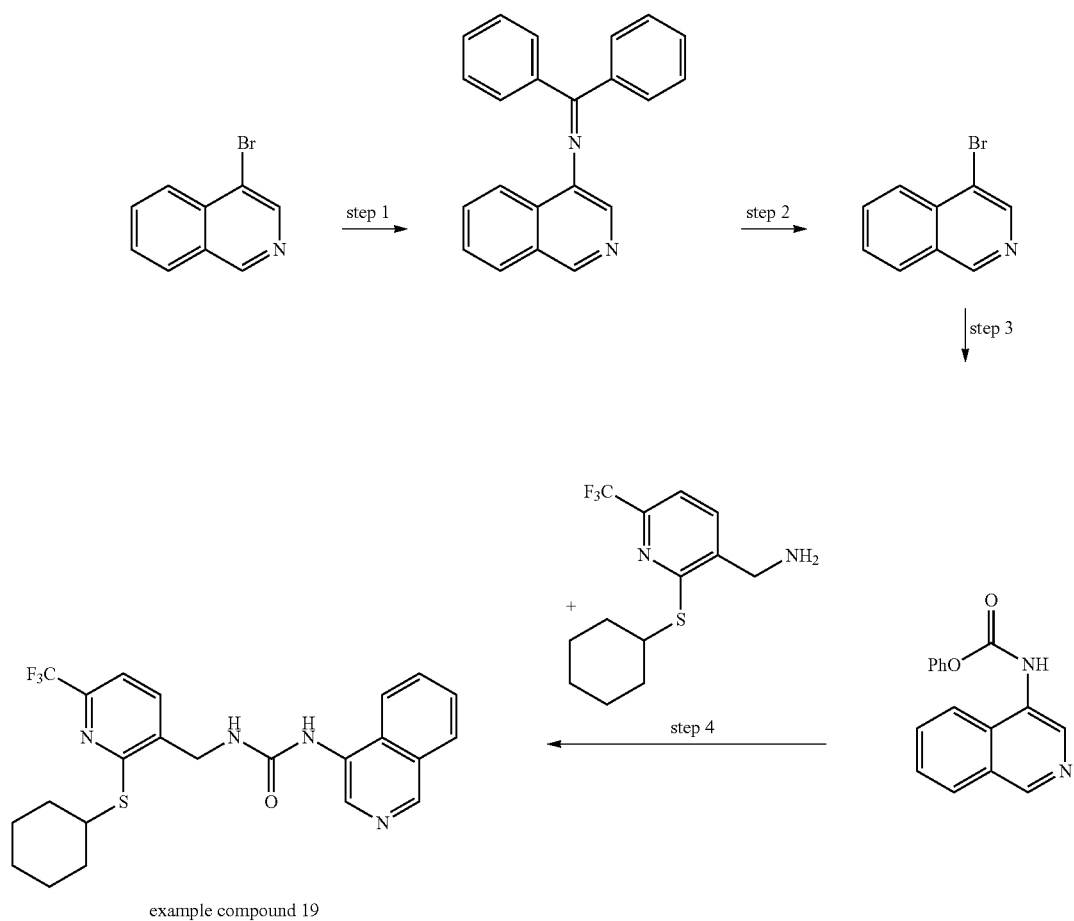

example compound 19

Step 1-3: as described for example 18

Step 4: Phenyl isoquinolin-4-ylcarbamate (68 mg, 0.26 mmol) and (2-(cyclohexylthio)-6-(trifluoromethyl)pyridin-3-yl)methanamine (78 mg, 0.27 mmol) were dissolved in dimethyl sulfoxide. Then triethylamine (0.08 mL, 0.52 mmol) was added to it. The mixture was stirred at room temperature for 12 h. The reaction mixture was diluted with water and extracted with ethyl acetate. The organic layer was concentrated under reduced pressure. The crude was purified by column chromatography to give 1-((2-(cyclohexylthio)-6-(trifluoromethyl)pyridin-3-yl)methyl)-3-(isoquinolin-4-yl)urea (example compound 19) (16 mg, 14%).

$^1$H NMR (300 MHz, CD$_3$OD): δ 9.01 (s, 1H, Ar—H), 8.79 (s, 1H, Ar—H), 8.14 (t, 2H, J=9.15 Hz, Ar—H), 7.87 (m, overlapped, 2H, Ar—H), 7.75 (t, 1H, J=8.25 Hz, Ar—H), 7.48 (d, 1H, J=7.68 Hz, Ar—H), 4.42 (s, 2H, Ar—CH$_2$), 4.03 (m, 1H, cyclohexane-CH), 2.15 (m, 2H, cyclohexane-CH$_2$), 1.82 (m, 2H, cyclohexane-CH$_2$), 1.66 (m, overlapped, 6H, cyclohexane-CH$_2$).

Synthesis of example 20: 1-(isoquinolin-1-yl)-3-((2-(4-methylpiperidin-1-yl)-6-(trifluoro-methyl)-pyridin-3-yl)methyl)urea

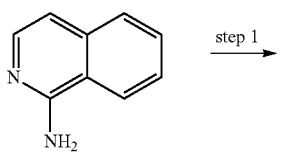

step 1

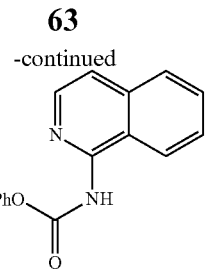

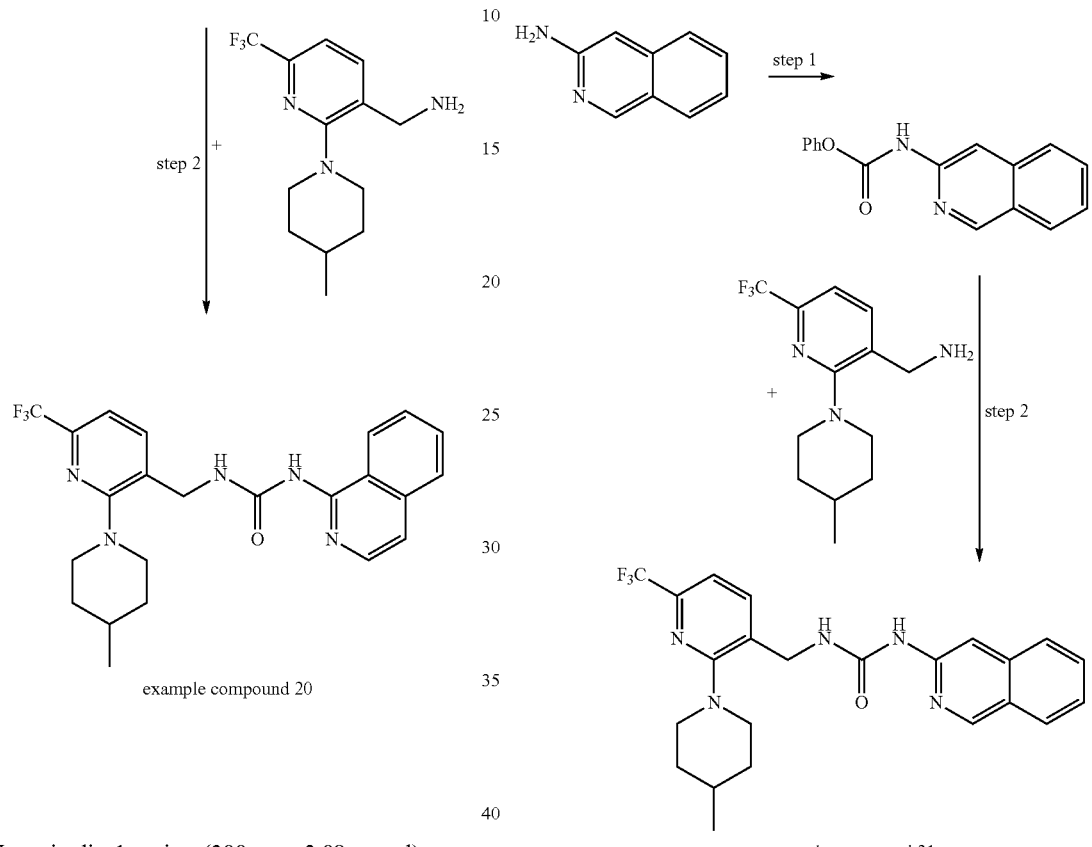

example compound 20

Step 1: Isoquinolin-1-amine (300 mg, 2.08 mmol) was dissolved in acetonitrile. The reaction mixture was added pyridine (0.02 mL, 2.50 mmol) and phenyl chloroformate (0.27 mL, 2.18 mmol) and stirred at room temperature for 1 h. The reaction mixture was diluted with water and extracted with ethyl acetate. The organic layer was concentrated under reduced pressure. The crude was purified by column chromatography to give phenyl isoquinolin-1-ylcarbamate (285 mg, 52%).

Step 2: Phenyl isoquinolin-1-ylcarbamate (80 mg, 0.30 mmol) and (2-(4-methylpiperidin-1-yl)-6-(trifluoromethyl) pyridin-3-yl)methanamine (87 mg, 0.32 mmol) was dissolved in dimethyl sulfoxide. Then triethylamine (0.08 mL, 0.61 mmol) was added to it. The mixture was stirred at room temperature for 12 h. The reaction mixture was diluted with water and extracted with ethyl acetate. The organic layer was concentrated under reduced pressure. The crude was purified by column chromatography to give 1-(isoquinolin-1-yl)-3-((2-(4-methylpiperidin-1-yl)-6-(trifluoromethyl)pyridin-3-yl)methyl)urea (example compound 20) (46 mg, 34%).

$^1$H NMR (300 MHz, DMSO): δ 10.58 (t, 1H, Ar—CH$_2$—NH), 9.82 (s, 1H, Ar—H), 8.67 (s, 1H, J=8.43 Hz, Ar—H), 8.08 (d, 1H, J=5.85 Hz, Ar—H), 7.92 (d, 1H, J=7.86 Hz, Ar—H), 7.85 (m, 2H, Ar—H), 7.66 (t, 1H, J=7.14 Hz, Ar—H), 7.45 (m, 2H, Ar—H), 4.58 (d, 2H, J=5.67 Hz, Ar—CH$_2$), 3.50 (m, 2H, piperidine-CH$_2$), 2.85 (m, 2H, piperidine-CH$_2$), 1.76 (m, 2H, piperidine-CH$_2$), 1.57 (m, 1H, piperidine-CH), 1.38 (m, 2H, piperidine-CH$_2$), 0.98 (d, 3H, J=6.42 Hz, piperidine-CH$_3$).

Synthesis of example 21: 1-(isoquinolin-3-yl)-3-((2-(4-methylpiperidin-1-yl)-6-(trifluoromethyl)pyridin-3-yl)methyl)urea example compound 21

Step 1: Isoquinolin-3-amine (300 mg, 2.08 mmol) was dissolved in acetonitrile. To the reaction mixture was added pyridine (0.20 mL, 2.50 mmol) and phenyl chloroformate (0.27 mL, 2.18 mmol), respectively and stirred at room temperature for 1 h. The reaction mixture was diluted with water and extracted with ethyl acetate. The organic layer was concentrated under reduced pressure. The crude was purified by column chromatography to give phenyl isoquinolin-3-ylcarbamate (456 mg, 83%).

Step 2: Phenyl isoquinolin-3-ylcarbamate (100 mg, 0.38 mmol) and (2-(4-methylpiperidin-1-yl)-6-(trifluoromethyl) pyridin-3-yl)methanamine (109 mg, 0.40 mmol) was dissolved in dimethyl sulfoxide. Then triethylamine (0.11 mL, 0.76 mmol) was added to it. The mixture was stirred at room temperature for 12 h. The reaction mixture was diluted with water and extracted with ethyl acetate. The organic layer was concentrated under reduced pressure. The crude was purified by column chromatography to give 1-(isoquinolin-3-yl)-3-((2-(4-methylpiperidin-1-yl)-6-(trifluoromethyl)pyridin-3-yl)methyl)urea (example compound 21) (130 mg, 77%).

$^1$H NMR (300 MHz, CD$_3$OD): δ 8.99 (s, 1H, Ar—H), 7.97 (d, 1H, J=8.22 Hz, Ar—H), 7.87 (d, 1H, J=7.53 Hz, Ar—H), 7.76 (d, 1H, J=8.43 Hz, Ar—H), 7.67 (d, 1H, J=6.96 Hz, Ar—H), 7.63 (s, 1H, Ar—H), 7.47 (t, 1H, J=6.96 Hz, Ar—H), 7.33 (d, 1H, J=7.68 Hz), 4.58 (s, 2H, Ar—CH$_2$), 3.51 (m, 2H, piperidine-CH$_2$), 2.92 (m, 2H, piperidine-CH$_2$), 1.79 (m, 2H, piperidine-CH$_2$), 1.59 (m, 1H, piperidine-CH), 1.48 (m, 2H, piperidine-CH$_2$), 1.02 (d, 3H, J=6.24 Hz, piperidine-CH$_3$).

Mass spectrometric data are cited hereinafter by way of example for the following example compounds in Tables 1a and 1b:

TABLE 1a

| Example compound | [M + H] |
|---|---|
| 1 | 432.5 |
| 5 | 434.0 |
| 8 | 447.2 |
| 9 | 434.2 |
| 11 | 460.5 |
| 12 | 443.5 |
| 14 | 457.3 |
| 15 | 474.3 |
| 17 | 444.1 |
| 18 | 444.1 |
| 19 | 461.0 |
| 20 | 444.1 |
| 21 | 444.1 |
| 51 | 451.3 |
| 52 | 439.1 |
| 53 | 450.0 |
| 54 | 422.0 |
| 56 | 447.1 |

TABLE 1b

| Example compound | [M + H] |
|---|---|
| 16 | 458.9 |
| 22 | 432.1 |
| 23 | 432.1 |
| 24 | 446.2 |
| 26 | 447.2 |
| 27 | 447.2 |
| 29 | 449.9 |
| 30 | 464.2 |
| 31 | 507.1 |
| 32 | 450.3 |
| 33 | 464.1 |
| 34 | 465.2 |
| 35 | 506.9 |
| 36 | 432.3 |
| 37 | 460.1 |
| 38 | 432.2 |
| 39 | 536.3 |
| 40 | 446.4 |
| 41 | 474.2 |
| 42 | 510.2 |
| 43 | 488.4 |
| 44 | 433.2 |
| 45 | 538.1 |
| 46 | 447.2 |
| 47 | 422.1 |
| 48 | 434.4 |
| 49 | 475.3 |
| 55 | 467.7 |
| 57 | 467.8 |
| 58 | 433.2 |
| 59 | 450.1 |
| 60 | 450.1 |
| 61 | 444.1 |
| 62 | 431.3 |
| 63 | 443.1 |
| 64 | 432.4 |
| 65 | 405.2 |
| 66 | 433.2 |
| 67 | 419.2 |
| 68 | 417.3 |
| 69 | 444.1 |
| 70 | 458.4 |
| 71 | 461.3 |
| 72 | 444.1 |
| 73 | 458.3 |
| 74 | 445.3 |
| 75 | 444.1 |
| 76 | 432.3 |
| 77 | 549.3 |
| 78 | 458.2 |
| 79 | 478.8 |
| 80 | 474.2 |
| 82 | 508.8 |
| 83 | 444.1 |
| 84 | 444.1 |
| 85 | 461.3 |
| 86 | 458.3 |
| 87 | 458.3 |
| 88 | 474.1 |
| 89 | 461.2 |
| 90 | 445.3 |
| 91 | 445.3 |

Pharmacological Methods

I. Functional Testing Carried Out on the Vanilloid Receptor 1 (VR1/TRPV1 Receptor)

The agonistic or antagonistic effect of the substances to be tested on the rat-species vanilloid receptor 1 (VR1/TRPV1) can be determined using the following assay. In this assay, the influx of Ca$^{2+}$ through the receptor channel is quantified with the aid of a Ca$^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:

Complete medium: 50 mL HAMS F12 nutrient mixture (Gibco Invitrogen GmbH, Karlsruhe, Germany) with 10% by volume of FCS (foetal calf serum, Gibco Invitrogen GmbH, Karlsruhe, Germany, heat-inactivated); 2 mM L-glutamine (Sigma, Munich, Germany); 1% by weight of AA solution (antibiotic/antimyotic solution, PAA, Pasching, Austria) and 25 ng/mL NGF medium (2.5 S, Gibco Invitrogen GmbH, Karlsruhe, Germany)

Cell culture plate: Poly-D-lysine-coated, black 96-well plates having a clear base (96-well black/clear plate, BD Biosciences, Heidelberg, Germany) are additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 µg/mL. Aliquots having a laminin concentration of 100 µg/mL are removed and stored at −20° C. The aliquots are diluted with PBS in a ratio of 1:10 to 10 µg/mL of laminin and respectively 50 µL of the solution are pipetted into a recess in the cell culture plate. The cell culture plates are incubated for at least two hours at 37° C., the excess solution is removed by suction and the recesses are each washed twice with PBS. The coated cell culture plates are stored with excess PBS which is not removed until just before the feeding of the cells.

Preparation of the Cells:

The vertebral column is removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column is cut longitudinally and removed together with fasciae from the vertebral canal. Subsequently, the dorsal root ganglia (DRG) are removed and again stored in cold HBSS buffer mixed with 1% by volume of an AA solution. The DRG, from which all blood remnants and spinal nerves have been removed, are transferred in each case to 500 µL of cold type 2 collagenase (PAA, Pasching, Austria) and incubated for 35 minutes at 37° C. After the addition of 2.5% by volume of trypsin (PAA, Pasching, Austria), incubation is continued for 10 minutes at 37° C. After complete incubation, the enzyme solution is carefully pipetted off and 500 µL of complete medium are added to each of the remaining DRG. The DRG are respectively suspended several times, drawn through cannulae No. 1, No. 12 and No. 16 using a syringe and transferred to a 50 mL Falcon tube which is filled up to 15 mL with complete medium. The contents of each Falcon tube are respectively filtered through a 70 µm Falcon filter element and centrifuged for 10 minutes at 1,200 rpm and room temperature. The resulting pellet is respectively taken up in 250 µL of complete medium and the cell count is determined.

The number of cells in the suspension is set to $3 \times 10^5$ per mL and 150 µL of this suspension are in each case introduced into a recess in the cell culture plates coated as described hereinbefore. In the incubator the plates are left for two to three days at 37° C., 5% by volume of $CO_2$ and 95% relative humidity. Subsequently, the cells are loaded with 2 µM of Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at room temperature used for $Ca^{2+}$ measurement in a FLIPR assay. The $Ca^{2+}$-dependent fluorescence is in this case measured before and after the addition of substances ($\lambda ex=488$ nm, $\lambda em=540$ nm). Quantification is carried out by measuring the highest fluorescence intensity (FC, fluorescence counts) over time.

FLIPR Assay:

The FLIPR protocol consists of 2 substance additions. First the compounds to be tested (10 µM) are pipetted onto the cells and the $Ca^{2+}$ influx is compared with the control (capsaicin 10 µM). This provides the result in % activation based on the $Ca^{2+}$ signal after the addition of 10 µM of capsaicin (CP). After 5 minutes' incubation, 100 nM of capsaicin are applied and the $Ca^{2+}$ influx is also determined.

Desensitising agonists and antagonists lead to suppression of the $Ca^{2+}$ influx. The % inhibition is calculated compared to the maximum achievable inhibition with 10 µM of capsazepine. Triple analyses (n=3) are carried out and repeated in at least 3 independent experiments (N=4). Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

Pharmacological Data

The affinity of the compounds of to the invention for the vanilloid receptor 1 (VR1/TRPV1 receptor) was determined as described hereinbefore (pharmacological method I). The compounds of the invention display outstanding affinity to the VR1/TRPV1 receptor (Table 2). In Table 2 the abbreviations below have the following meanings:
Cap=capsaicin
AG=agonist
NE=no effect The value after the "@" symbol indicates the concentration at which the inhibition (as a percentage) was respectively determined.

TABLE 2

| Compound according to Example | (f) Ki (human being) [nM] Cap |
|---|---|
| 1 | 9 |
| 5 | 21 |
| 8 | 2 |
| 9 | 22% @5 µM |
| 11 | 19% @5 µM |
| 12 | 9 |
| 14 | 44 |
| 15 | 50 |
| 17 | AG |
| 18 | 2 |
| 19 | 4 |
| 21 | 39% @5 µM |
| 22 | 24 |
| 23 | 13 |
| 24 | 26 |
| 26 | AG |
| 27 | 7 |
| 29 | 5 |
| 30 | 22 |
| 31 | AG |
| 32 | 4 |
| 33 | 4 |
| 34 | 50 |
| 35 | 47% @5 µM |
| 36 | 37% @0.1 µM |
| 37 | 4 |
| 38 | 1 |
| 39 | 8 |
| 40 | 5 |
| 41 | 8 |
| 42 | 2 |
| 43 | 8 |
| 44 | 0.4 |
| 45 | 7 |
| 46 | 0.5 |
| 47 | 3 |
| 48 | 2 |
| 49 | 13 |
| 51 | 3 |
| 52 | 2 |
| 53 | 1 |
| 54 | 7 |
| 55 | 4 |
| 56 | 45% @5 µM |
| 57 | 3 |
| 58 | 3 |
| 59 | 18 |
| 60 | 1 |
| 61 | 0.7 |
| 62 | 1 |
| 63 | 0.7 |
| 64 | 1 |
| 65 | 4 |
| 66 | 2 |
| 67 | 2 |
| 68 | 2 |
| 69 | 40% @1 µM |
| 70 | 68 |
| 71 | 5 |
| 72 | 92 |
| 73 | 24 |
| 74 | 24% @5 µM |
| 75 | 0.2 |
| 76 | 0.1 |
| 77 | 4 |
| 78 | 1 |
| 79 | 0.8 |
| 80 | 8 |
| 82 | 1 |
| 83 | 7 |
| 84 | 8 |

TABLE 2-continued

| Compound according to Example | (f) Ki (human being) [nM] Cap |
|---|---|
| 85 | 1 |
| 86 | 52 |
| 87 | 15 |
| 88 | 62 |
| 89 | 17 |
| 90 | 48 |
| 91 | 8 |
| 16 | 10 |
| 20 | NE |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound of formula (I):

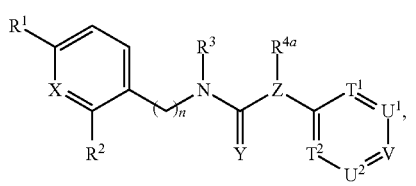

wherein
X represents N or CH;
$R^1$ is selected from the group consisting of tert-butyl, $CF_3$ and cyclopropyl;
$R^2$ represents substructure (T1):

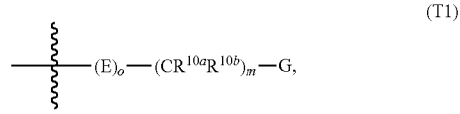

wherein
E represents O or S;
o represents 0 or 1;
$R^{10a}$ and $R^{10b}$ are each independently selected from the group consisting of H, methyl and ethyl;
m represents 0 or 1; and
G is selected from the group consisting of a cycloaliphatic group, a heterocycloaliphatic group, and an aryl group, wherein the cycloaliphatic group or the heterocycloaliphatic group is selected from the group consisting of cyclohexyl and piperidinyl, in each case unsubstituted or mono- or polysubstituted with one or more substituents each independently selected from the group consisting of F, Cl, Br, I, OH, $C_{1-4}$ alkyl, O—$C_{1-4}$ alkyl, $NH_2$, $NH(C_{1-4}$ alkyl), $N(C_{1-4}$ alkyl)$_2$, and phenyl, wherein phenyl can be unsubstituted or mono- or polysubstituted with one or more substituents each independently selected from the group consisting of F, Cl, Br, I, CN, OH, O—$C_{1-4}$ alkyl, $OCF_3$, $C_{1-4}$ alkyl, $CF_3$, and $SCF_3$; and wherein the an aryl group is phenyl, unsubstituted or mono- or polysubstituted with one or more substituents independently selected from the group consisting of F, Cl, Br, I, CN, OH, O—$C_{1-4}$ alkyl, $OCF_3$, $C_{1-4}$ alkyl, $CF_3$, $SCF_3$, $NH_2$, $NH(C_{1-4}$ alkyl) and $N(C_{1-4}$ alkyl)$_2$;
n represents 1;
$R^3$ is H;
$R^{4a}$ represents H or methyl;
Y represents O;
Z represents N or C—$R^{4b}$;
$R^{4b}$ represents H;
$T^1$ represents N or C—$R^5$;
$U^1$ represents N or C—$R^6$;
V represents N or C—$R^7$;
$U^2$ represents C—$R^8$;
$T^2$ represents C—$R^9$;
with the proviso that 1 or 2 of variables $T^1$, $U^1$, and V represent a nitrogen atom; and
$R^5$ and $R^6$ together, or
$R^6$ and $R^7$ together, or
$R^7$ and $R^8$ together, or
$R^8$ and $R^9$ together,
in pairs in each case independently of one another, together with the carbon atoms connecting them form a $C_5$—$C_6$-cycloaliphatic residue or a 5 to 6 membered heterocycloaliphatic residue, in each case unsubstituted or mono- or polysubstituted with one or more substituents independently selected from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, $N(C_{1-4}$ alkyl)$_2$, NH—$SO_2$—$C_{1-4}$ alkyl and NH—C(=O)—$C_{1-4}$ alkyl, wherein the heterocycloaliphatic residue comprises 1 or 2 atoms selected from the group consisting of N and O, or
in pairs in each case independently of one another, together with the carbon atoms connecting them form an aryl, or a 5-6 membered heteroaryl, in each case unsubstituted or mono- or polysubstituted with one or more substituents independently selected from the group consisting of F, Cl, Br, I, $C_{1-4}$ alkyl, $C_{1-4}$ alkyl-OH, C(=O)—$C_{1-4}$ alkyl, O—$C_{1-4}$ alkyl, O—$C_{1-4}$ alkylene-OH, O—$C_{1-4}$ alkylene-O—$C_{1-4}$ alkyl, OH, $SO_2$—$C_{1-4}$ alkyl, $NH_2$, NH—$C_{1-4}$ alkyl, $N(C_{1-4}$ alkyl)$_2$, NH—$SO_2$—$C_{1-4}$ alkyl and NH—C(=O)—$C_{1-4}$ alkyl, wherein the heteroaryl comprises 1 or 2 atoms selected from the group consisting of N, O, and S, and
the respective remaining substituents of $R^5$, $R^6$, $R^7$, $R^8$, and $R^9$ each independently represent H; F; Cl; Br; I; $CF_3$; OH; $OCF_3$; O—$C_{1-4}$ alkyl, O—$C_{1-4}$ alkylene-OH, $C_{1-4}$ alkyl, $C_{1-4}$ alkyl-OH, $NH_2$; NH—$C_{1-4}$ alkyl, $N(C_{1-4}$ alkyl)$_2$, NH—$SO_2$—$C_{1-4}$ alkyl, NH—C(=O)—$C_{1-4}$ alkyl, $SCF_3$; or $SO_2$—$C_{1-4}$ alkyl;
optionally in the form of a single stereoisomer or a mixture of stereoisomers, in the form of the free compound and/or a physiologically acceptable salt thereof.

2. A compound according to claim 1, wherein:
Z represents N, and $R^{4a}$ represents H; or
Z represents $CR^{4b}$, and $R^{4a}$ and $R^{4b}$ each represent H; or
Z represents $CR^{4b}$; $R^{4a}$ represents methyl, and $R^{4b}$ represents H.

3. A compound according to claim 1, wherein in formula (I) the substructure (T2):

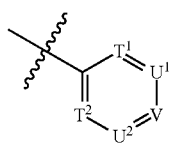

represents a substructure selected from the group consisting of:

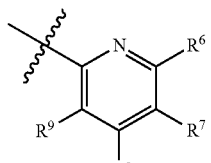
(T2-a)

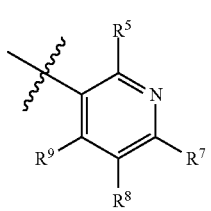
(T2-b)

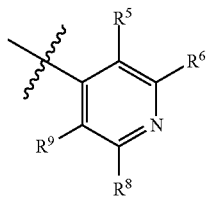
(T2-c)

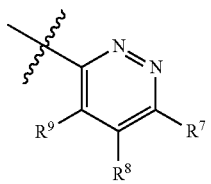
(T2-d)

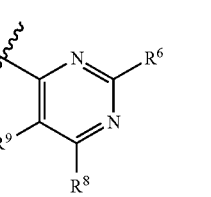
(T2-e)

and

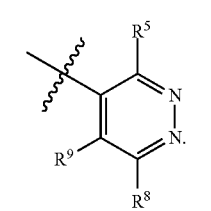
(T2-h)

4. A compound according to claim 1, selected from the group consisting of:
1. 1-(6,7-Dihydro-5H-cyclopenta[b]pyridin-3-yl)-3-((2-(4-methylpiperidin-1-yl)-6-(trifluoromethyl)pyridin-3-yl)methyl)urea;
2. 1-((2-(4-Methylpiperidin-1-yl)-6-(trifluoromethyl)pyridin-3-yl)methyl)-3-(5,6,7,8-tetrahydroisoquinolin-4-yl)urea;
3. 1-(2,3-Dihydro-[1,4]dioxino[2,3-b]pyridin-6-yl)-3-((2-(4-methylpiperidin-1-yl)-6-(trifluoromethyl)pyridin-3-yl)methyl)urea;
4. 1-(2,3-Dihydro-1H-pyrrolo[2,3-b]pyridin-5-yl)-3-((2-(4-methylpiperidin-1-yl)-6-(trifluoromethyl)pyridin-3-yl)methyl)urea;
5. 1-((2-(4-methylpiperidin-1-yl)-6-(trifluoromethyl)pyridin-3-yl)methyl)-3-(1H-pyrazolo[3,4-b]pyridin-5-y) urea;
6. 1-((2-(3-Fluorophenyl)-6-(trifluoromethyl)pyridin-3-yl)methyl)-3 -(oxazolo [5 ,4-b]pyridin-6-yl)urea;
7. 1-((2-(4-Methylpiperidin-1-yl)-6-(trifluoromethyl)pyridin-3-yl)methyl)-3-(2-methylthiazolo [5 ,4-b]pyridin-6-yl)urea;
8. N-((2-(4-Methylpiperidin-1-yl)-6-(trifluoromethyl)pyridin-3-yl)methyl)-2-(1H-pyrazolo [3 ,4-b]pyridin-4-yl)propanamide;
9. 1-((2-(4-Methylpiperidin-1-yl)-6-(trifluoromethyl)pyridin-3-yl)methyl)-3-(1H-pyrazolo [3 ,4-b]pyridin-4-yl)urea;
10. 1-((2-(4-Methylpiperidin-1-yl)-6-(trifluoromethyl)pyridin-3-yl)methyl)-3-(1H-pyrazolo [4,3-c]pyridin-4-yl) urea;
11. 1-((2-(Cyclohexylthio)-6-(trifluoromethyl)pyridin-3-yl)methyl)-3-(quinolin-2-yl)urea;
12. 1-((2-(4-Methylpiperidin-1-yl)-6-(trifluoromethyl)pyridin-3-yl)methyl)-3-(quinolin-3-yl)urea;
13. N-((2-(4-Methylpiperidin-1-yl)-6-(trifluoromethyl) pyridin-3-yl)methyl)-2-(quinolin-3-yl)acetamide;
14. N-((2-(4-Methylpiperidin-1-yl)-6-(trifluoromethyl) pyridin-3-yl)methyl)-2-(quinolin-3-yl)propanamide;
15. N-((2-(Cyclohexylthio)-6-(trifluoromethyl)pyridin-3-yl)methyl)-2-(quinolin-3-y1)propanamide;
16. N-(2-(4-Methylpiperidin-1-yl)-4-(trifluoromethyl) benzyl)-2-(quinolin-3-yl)propanamide;
17. 1-((2-(4-Methylpiperidin-1-yl)-6-(trifluoromethyl)pyridin-3-yl)methyl)-3-(quinolin-4-yl)urea;
18. 1-(Isoquinolin-4-yl)-3-((2-(4-methylpiperidin-1-yl)-6-(trifluoromethyl)pyridin-3-yl)methyl)urea;
19. 1-((2-(Cyclohexylthio)-6-(trifluoromethyl)pyridin-3-yl)methyl)-3-(isoquinolin-4-yl)urea;
20. 1-(Isoquinolin-1-yl)-3-((2-(4-methylpiperidin-1-yl)-6-(trifluoromethyl)pyridin-3-yl)methyl)urea;
21. 1-(Isoquinolin-3-yl)-3-((2-(4-methylpiperidin-1-yl)-6-(trifluoromethyl)pyridin-3-yl)methyl)urea;
92. 1-((2-(4-Methylpiperidin-1-yl)-6-(trifluoromethyl)pyridin-3-yl)methyl)-3-(quinolin-2-yl)urea; and
97. 1-((2-(4-Methylpiperidin-1-yl)-6-(trifluoromethyl)pyridin-3-yl)methyl)-3-(1,7-naphthyridin-8-yl)urea;
optionally in the form of a single stereoisomer or a mixture of stereoisomers, in the form of the free compound and/or a physiologically acceptable salt thereof 5. A pharmaceutical composition comprising a compound according to claim 1 and at least one pharmaceutically acceptable carrier or auxiliary substance.

* * * * *